United States Patent [19]
Goldberg

[11] Patent Number: 5,864,013
[45] Date of Patent: Jan. 26, 1999

[54] MATERIALS FOR THE PRODUCTION OF NANOMETER STRUCTURES AND USE THEREOF

[75] Inventor: Edward B. Goldberg, Newton, Mass.

[73] Assignee: NanoFrames, LLC, Brookline, Mass.

[21] Appl. No.: 542,003

[22] Filed: Oct. 12, 1995

Related U.S. Application Data

[63] Continuation-in-part of Ser. No. 322,760, Oct. 13, 1994.

[51] Int. Cl.$^6$ .............................. C07K 14/00; C12P 21/06
[52] U.S. Cl. ......................... 530/350; 530/300; 530/324; 435/69.1; 435/69.7
[58] Field of Search ..................................... 530/350, 300, 530/324; 435/69.1, 69.7

[56] References Cited

PUBLICATIONS

Bella et al., 1994, "Crystal and molecular structure of a collagen–like peptide at 1.9Å resolution", Science 226:75–81.
Earnshaw et al., 1979, "The distal half of the tail fibre of the bacteriophage T4 rigidly linked domains and cross–β structure", J Mol Biol 132:101–131.
Edgar and Lielausis, 1965, "Serological studies with mutants of phage T4D defective in genes determining tail fiber structure", Genetics 52:1187–1200.
Freedman, 1991, "Exploiting the nanotechnology of life", Science 254(29):1308–1310.
Harbury et al., 1993, "A switch between two–, three–and four–standard coiled coils in GCN4 leucine zipper mutants", Science 262:1401–1407.
Henning et al., 1994, "Receptor recognition by T–even–type coliphages", in *Molecular Biology of Bacteriophage T4*, Karam (ed.), American Society of Microbiology, Washington, D.C. pp. 291–298.
Levy et al., 1980, "Region–specific recombination in phage T4. II. Structure of the recombinants", Genetics 94:531–547.
O'Shea et al., 1989, "Evidence that the leucine zipper is a coiled coil", Science 243:538–542.
Oliver and Crowther, 1981, "DNA Sequence of the tail fibre genes 36 and 37 of bacteriophage T4", J Mol Biol 153:545–568.
Seed, 1980, "Studies of the bacteriophage T4 proximal half tail fiber", Ph.D. Thesis (C.I.T.).
Steven et al., 1988, "Molecular substructure of a viral receptor–recognition proten: The gp17 tail fiber of bacteriophage T7", J Mol Biol 200:351–365.
Ward et al., 1970, "Assembly of bacteriophage T4 tail fibers II. Isolation and characterization of tail fiber precursors", J Mol Biol 54:15–31.
Whitesides et al., 1991, "Molecular self–assembly and nanochemistry: A chemical strategy for the synthesis of nanostructures"Science 254(29):1312–1318.
Wood et al., 1994, "Long tail fibers: Genes, proteins, structure and assembly", in *Molecular Biology of Bacteriophage T4*, Karam (ed.), American Society of Microbiology, Washington, D.C. pp. 282–290.

*Primary Examiner*—Karen Cochrane Carlson
*Attorney, Agent, or Firm*—Pennie & Edmonds LLP

[57] ABSTRACT

The present invention pertains to nanostructures, i.e., nanometer sized structures useful in the construction of microscopic and macroscopic structures. In particular, the present invention pertains to nanostructures based on bacteriophage T4 tail fiber proteins and variants thereof.

22 Claims, 26 Drawing Sheets

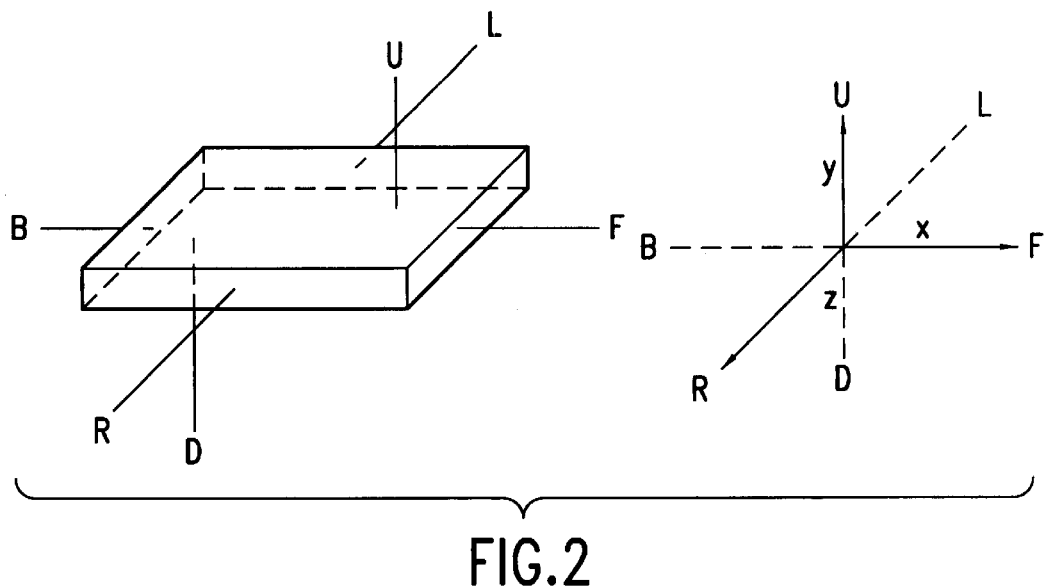

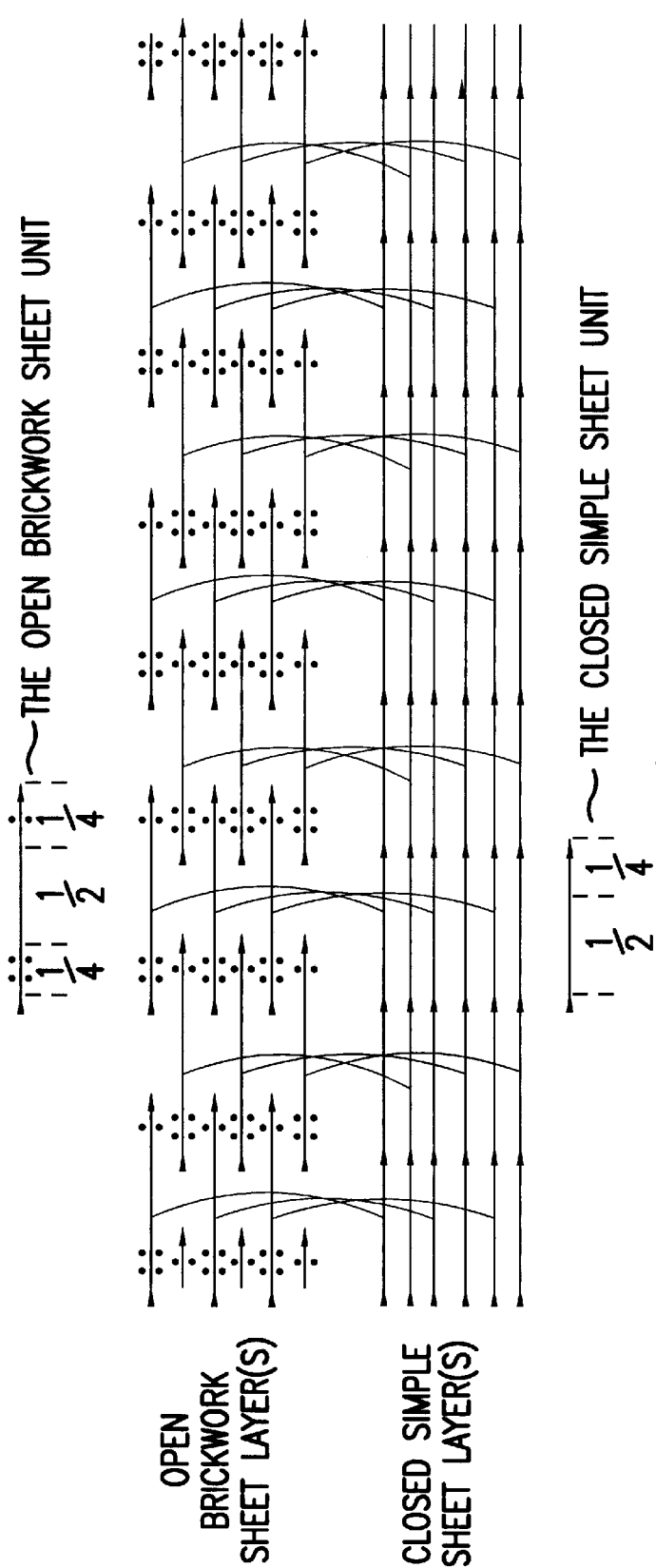
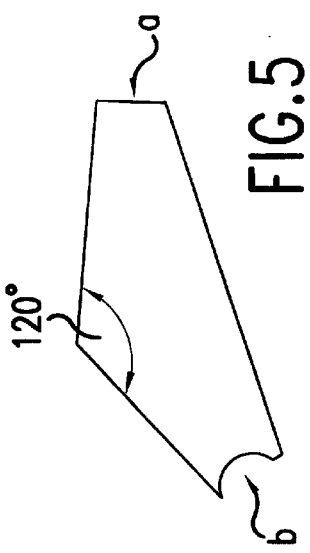
FIG. 4
FIG. 5

```
        |   10       |   20       |   30       |   40       |   50       |   60
   1  TAGGAGCCCG GGAGAATGGC CGAGATTAAA AGAGAATTCA GAGCAGAAGA TGGTCTGGAC   60
  61  GCAGGTGGTG ATAAAATAAT CAACGTAGCT TTAGCTGATC GTACCGTAGG AACTGACGGT  120
 121  GTTAACGTTG ATTACTTAAT TCAAGAAAAC ACAGTTCAAC AGTATGATCC AACTCGTGGA  180
 181  TATTTAAAAG ATTTTGTAAT CATTTATGAT AACCGCTTTT GGGCTGCTAT AAATGATATT  240
 241  CCAAAACCAG CAGGAGCTTT TAATAGCGGA CGCTGGAGAG CATTACGTAC CGATGCTAAC  300
 301  TGGATTACGG TTTCATCTGG TTCATATCAA TTAAAATCTG GTGAAGCAAT TTCGGTTAAC  360
 361  ACCGCAGCTG GAAATGACAT CACGTTTACT TTACCATCTT CTCCAATTGA TGGTGATACT  420
 421  ATCGTTCTCC AAGATATTGG AGGAAAACCT GGAGTTAACC AAGTTTTAAT TGTAGCTCCA  480
 481  GTACAAAGTA TTGTAAACTT TAGAGGTGAA CAGGTACGTT CAGTACTAAT GACTCATCCA  540
 541  AAGTCACAGC TAGTTTTAAT TTTTAGTAAT CGTCTGTGGC AAATGTATGT TGCTGATTAT  600
 601  AGTAGAGAAG CTATAGTTGT AACACCAGCG AATACTTATC AAGCGCAATC CAACGATTTT  660
 661  ATCGTACCTA GATTTACTTC TGCTGCACCA ATTAATGTCA AACTTCCAAG ATTTGCTAAT  720
 721  CATGGCGATA TTATTAATTT CGTCGATTTA GATAAACTAA ATCCGCTTTA TCATACAATT  780
 781  GTTACTACAT ACGATGAAAC GACTTCAGTA CAAGAAGTTG GAACTCATTC CATTGAAGGC  840
 841  CGTACATCGA TTGACGGTTT CTTGATGTTT GATGATAATG AGAAATTATG GAGACTGTTT  900
 901  GACGGGGATA GTAAAGCGCG TTTACGTATC ATAACGACTA ATTCAAACAT TCGTCCAAAT  960
 961  GAAGAAGTTA TGGTATTTGG TGCGAATAAC GGAACAACTC AAACAATTGA GCTTAAGCTT 1020
1021  CCAACTAATA TTTCTGTTGG TGATACTGTT AAAATTTCCA TGAATTACAT GAGAAAAGGA 1080
1081  CAAACAGTTA AAATCAAAGC TGCTGATGAA GATAAAATTG CTTCTTCAGT TCAATTGCTG 1140
1141  CAATTCCCAA AACGCTCAGA ATATCCACCT GAAGCTGAAT GGGTTACAGT TCAAGAATTA 1200
1201  GTTTTTAACG ATGAAACTAA TTATGTTCCA GTTTTGGAGC TTGCTTACAT AGAAGATTCT 1260
1261  GATGGAAAAT ATTGGGTTGT ACAGCAAAAC GTTCCAACTG TAGAAAGAGT AGATTCTTTA 1320
1321  AATGATTCTA CTAGAGCAAG ATTAGGCGTA ATTGCTTTAG CTACACAAGC TCAAGCTAAT 1380
1381  GTCGATTTAG AAAATTCTCC ACAAAAAGAA TTAGCAATTA CTCCAGAAAC GTTAGCTAAT 1440
1441  CGTACTGCTA CAGAAACTCG CAGAGGTATT GCAAGAATAG CAACTACTGC TCAAGTGAAT 1500
1501  CAGAACACCA CATTCTCTTT TGCTGATGAT ATTATCATCA CTCCTAAAAA GCTGAATGAA 1560
1561  AGAACTGCTA CAGAAACTCG TAGAGGTGTC GCAGAAATTG CTACGCAGCA AGAAACTAAT 1620
1621  GCAGGAACCG ATGATACTAC AATCATCACT CCTAAAAAGC TTCAAGCTCG TCAAGGTTCT 1680
1681  GAATCATTAT CTGGTATTGT AACCTTTGTA TCTACTGCAG GTGCTACTCC AGCTTCTAGC 1740
1741  CGTGAATTAA ATGGTACGAA TGTTTATAAT AAAAACACTG ATAATTTAGT TGTTTCACCT 1800
1801  AAAGCTTTGG ATCAGTATAA AGCTACTCCA ACACAGCAAG GTGCAGTAAT TTTAGCAGTT 1860
1861  GAAAGTGAAG TAATTGCTGG ACAAAGTCAG CAAGGATGGG CAAATGCTGT TGTAACGCCA 1920
1921  GAAACGTTAC ATAAAAAGAC ATCAACTGAT GGAAGAATTG GTTAATTGA AATTGCTACG 1980
1981  CAAAGTGAAG TTAATACAGG AACTGATTAT ACTCGTGCAG TCACTCCTAA AACTTTAAAT 2040
2041  GACCGTAGAG CAACTGAAAG TTTAAGTGGT ATAGCTGAAA TTGCTACACA AGTTGAATTC 2100
2101  GACGCAGGCC TCGACGATAC TCGTATCTCT ACACCATTAA AAATTAAAAC CAGATTTAAT 2160
2161  AGTACTGATC GTACTTCTGT TGTTGCTCTA TCTGGATTAG TTGAATCAGG AACTCTCTGG 2220
2221  GACCATTATA CACTTAATAT TCTTGAAGCA AATGAGACAC AACCGTGGTAC ACTTCGTGTA 2280
2281  GCTACGCAGG TCGAAGCTGC TGCGGGAACA TTAGATAATG TTTTAATAAC TCCTAAAAAG 2340
```

FIG.6A

```
2341 CTTTTAGGTA CTAAATCTAC TGAAGCGCAA GAGGGTGTTA TTAAAGTTGC AACTCAGTCT 2400
2401 GAAACTGTGA CTGGAACGTC AGCAAATACT GCTGTATCTC CAAAAAATTT AAAATGGATT 2460
2461 GCGCAGAGTG AACCTACTTG GGCAGCTACT ACTGCAATAA GAGGTTTTGT TAAAACTTCA 2520
2521 TCTGGTTCAA TTACATTCGT TGGTAATGAT ACAGTCGGTT CTACCCAAGA TTTAGAACTG 2580
2581 TATGAGAAAA ATAGCTATGC GGTATCACCA TATGAATTAA ACCGTGTATT AGCAAATTAT 2640
2641 TTGCCACTAA AAGCAAAAGC TGCTGATACA AATTTATTGG ATGGTCTAGA TTCATCTCAG 2700
2701 TTCATTCGTA GGGATATTGC ACAGACGGTT AATGGTTCAC TAACCTTAAC CCAACAAACG 2760
2761 AATCTGAGTG CCCCTCTTGT ATCATCTAGT ACTGGTGAAT TGGTGGTTC ATTGGCCGCT 2820
2821 AATAGAACAT TTACCATCCG TAATACAGGA GCCCCGACTA GTATCGTTTT CGAAAAAGGT 2880
2881 CCTGCATCCG GGGCAAATCC TGCACAGTCA ATGAGTATTC GTCTATGGGG TAACCAATTT 2940
2941 GGCGGCGGTA GTGATACGAC CCGTTCGACA GTGTTTGAAG TTGGCGATGA CACATCTCAT 3000
3001 CACTTTTATT CTCAACGTAA TAAAGACGGT AATATAGCGT TTAACATTAA TGGTACTGTA 3060
3061 ATGCCAATAA ACATTAATGC TTCCGGTTTG ATGAATGTGA ATGGCACTGC AACATTCGGT 3120
3121 CGTTCAGTTA CAGCCAATGG TGAATTCATC AGCAAGTCTG CAAATGCTTT TAGAGCAATA 3180
3181 AACGGTGATT ACGGATTCTT TATTCGTAAT GATGCCTCTA ATACCTATTT TTTGCTCACT 3240
3241 GCAGCCGGTG ATCAGACTGG TGGTTTTAAT GGATTACGCC CATTATTAAT TAATAATCAA 3300
3301 TCCGGTCAGA TTACAATTGG TGAAGGCTTA ATCATTGCCA AAGGTGTTAC TATAAATTCA 3360
3361 GGCGGTTTAA CTGTTAACTC GAGAATTCGT TCTCAGGGTA CTAAAACATC TGATTTATAT 3420
3421 ACCCGTGCGC CAACATCTGA TACTGTAGGA TTCTGGTCAA TCGATATTAA TGATTCAGCC 3480
3481 ACTTATAACC AGTTCCCGGG TTATTTTAAA ATGGTTGAAA AAACTAATGA AGTGACTGGG 3540
3541 CTTCCATACT TAGAACGTGG CGAAGAAGTT AAATCTCCTG GTACACTGAC TCAGTTTGGT 3600
3601 AACACACTTG ATTCGCTTTA CCAAGATTCG ATTACTTATC CAACGACGCC AGAAGCGCGT 3660
3661 ACCACTCGCT GGACACGTAC ATGGCAGAAA ACCAAAAACT CTTGGTCAAG TTTTGTTCAG 3720
3721 GTATTTGACG GAGGTAACCC TCCTCAACCA TCTGATATCG GTGCTTTACC ATCTGATAAT 3780
3781 GCTACAATGG GGAATCTTAC TATTCGTGAT TTCTTGCGAA TTGGTAATGT TCGCATTGTT 3840
3841 CCTGACCCAG TGAATAAAAC GGTTAAATTT GAATGGGTTG AATAAGAGGT ATTATGGAAA 3900
3901 AATTTATGGC CGAGATTTGG ACAAGGATAT GTCCAAACGC CATTTTATCG GAAAGTAATT 3960
3961 CAGTAAGATA TAAAATAAGT ATAGCGGGTT CTTGCCCGCT TTCTACAGCA GGACCATCAT 4020
4021 ATGTTAAATT TCAGGATAAT CCTGTAGGAA GTCAAACATT TAGGCGCAGG CCTTCATTTA 4080
4081 AGAGTTTTTG ACCCTTCCAC CGGAGCATTA GTTGATAGTA AGTCATATGC TTTTTCGACT 4140
4141 TCAAATGATA CTACATCAGC TGCTTTTGTT AGTTTTCATG AATTCTTTGA CGAATAATCG 4200
4201 AATTGTTGCT ATATTAACTA GTGGAAAGGT TAATTTTCCT CCTGAAGTAG TATCTTGGTT 4260
4261 AAGAACCGCC GGAACGTCTG CCTTTCCATC TGATTCTATA TTGTCAAGAT TTGACGTATC 4320
4321 ATATGCTGCT TTTTATACTT CTTCTAAAAG AGCTATCGCA TTAGAGCATG TTAAACTGAG 4380
4381 TAATAGAAAA AGCACAGATG ATTATCAAAC TATTTTAGAT GTTGTATTTG ACAGTTTAGA 4440
4441 AGATGTAGGA GCTACCGGGT TTCCAAGAAG AACGTATGAA AGTGTTGAGC AATTCATGTC 4500
4501 GGCAGTTGGT GGAACTAATA ACGAAATTGC GAGATTGCCA ACTTCAGCTG CTATAAGTAA 4560
4561 ATTATCTGAT TATAATTTAA TTCCTGGAGA TGTTCTTTAT CTTAAAGCTC AGTTATATGC 4620
4621 TGATGCTGAT TTACTTGCTC TTGGAACTAC AAATATATCT ATCCGTTTTT ATAATGCATC 4680
4681 TAACGGATAT ATTTCTTCAA CACAAGCTGA ATTTACTGGG CAAGCTGGGT CATGGGAATT 4740
```

FIG.6B

```
4741 AAAGGAACAT TATGTAGTTG TTCCAGAAAA CGCAGTAGGA TTTACGATAT ACGCACAGAG 4800
4801 AACTGCACAA GCTGGCCAAG GTGGCATGAG AAATTTAAGC TTTTCTGAAG TATCAAGAAA 4860
4861 TGGCGGCATT TCGAAACCTG CTGAATTTGG CGTCAATGGT ATTCGTGTTA ATTATATCTG 4920
4921 CGAATCCGCT TCACCTCCGG ATATAATGGT ACTTCCTACG CAAGCATCGT CTAAAACTGG 4980
4981 TAAAGTGTTT GGGCAAGAAT TTAGAGAAGT TTAAATTGAC GGACCCTTCG GGTTCCCTTT 5040
5041 TTCTTTATAA ATACTATTCA AATAAAGGGG CATACAATGG CTGATTTAAA AGTAGGTTCA 5100
5101 ACAACTGGAG GCTCTGTCAT TTGGCATCAA GGAAATTTTC CATTGAATCC AGCCGGTGAC 5160
5161 GATGTACTCT ATAAATCATT TAAAATATAT TCAGAATATA ACAAACCACA AGCTGCTGAT 5220
5221 AACGATTTCG TTTCTAAAGC TAATGGTGGT ACTTATGCAT CAAAGGTAAC ATTTAACGCT 5280
5281 GGCATTCAAG TCCCATATGC TCCAAACATC ATGAGCCCAT GCGGGATTTA TGGGGGTAAC 5340
5341 GGTGATGGTG CTACTTTTGA TAAAGCAAAT ATCGATATTG TTTCATGGTA TGGCGTAGGA 5400
5401 TTTAAATCGT CATTTGGTTC AACAGGCCGA ACTGTTGTAA TTAATACACG CAATGGTGAT 5460
5461 ATTAACACAA AAGGTGTTGT GTCGGCAGCT GGTCAAGTAA GAAGTGGTGC GGCTGCTCCT 5520
5521 ATAGCAGCCA ATGACCTTAC TAGAAAGGAC TATGTTGATG GAGCAATAAA TACTGTTACT 5580
5581 GCAAATGCAA ACTCTAGGGT GCTACGGTCT GGTGACACCA TGACAGGTAA TTTAACAGCG 5640
5641 CCAAACTTTT TCTCGCAGAA TCCTGCATCT CAACCCTCAC ACGTTCCACG ATTTGACCAA 5700
5701 ATCGTAATTA AGGATTCTGT TCAAGATTTC GGCTATTATT AAGAGGACTT ATGGCTACTT 5760
5761 TAAAACAAAT ACAATTTAAA AGAAGCAAAA TCGCAGGAAC ACGTCCTGCT GCTTCAGTAT 5820
5821 TAGCCCGAAGG TGAATTGGCT ATAAACTTAA AAGATAGAAC AATTTTTACT AAAGATGATT 5880
5881 CAGGAAAATAT CATCGATCTA GGTTTTGCTA AAGGCGGGCA AGTTGATGGC AACGTTACTA 5940
5941 TTAACGGACT TTTGAGATTA AATGGCGATT ATGTACAAAC AGGTGGAATG ACTGTAAACG 6000
6001 GACCCATTGG TTCTACTGAT GGCGTCACTG GAAAAATTTT CAGATCTACA CAGGGTTCAT 6060
6061 TTTATGCAAG AGCAACAAAC GATACTTCAA ATGCCCATTT ATGGTTTGAA AATGCCGATG 6120
6121 GCACTGAACG TGGCGTTATA TATGCTCGCC CTCAAACTAC AACTGACGGT GAAATACGCC 6180
6181 TTAGGGTTAG ACAAGGAACA GGAAGCACTG CCAACAGTGA ATTCTATTTC CGCTCTATAA 6240
6241 ATGGAGGCGA ATTTCAGGCT AACCGTATTT TAGCATCAGA TTCGTTAGTA ACAAAACGCA 6300
6301 TTGCGGTTGA TACCGTTATT CATGATGCCA AAGCATTTGG ACAATATGAT TCTCACTCTT 6360
6361 TGGTTAATTA TGTTTATCCT GGAACCGGTG AAACAAATGG TGTAAACTAT CTTCGTAAAG 6420
6421 TTCGCGCTAA GTCCGGTGGT ACAATTTATC ATGAAATTGT TACTGCACAA ACAGGCCTGG 6480
6481 CTGATGAAGT TTCTTGGTGG TCTGGTGATA CACCAGTATT TAAACTATAC GGTATTCGTG 6540
6541 ACGATGGCAG AATGATTATC CGTAATAGCC TTGCATTAGG TACATTCACT ACAAATTTCC 6600
6601 CGTCTAGTGA TTATGGCAAC GTCGGTGTAA TGGGCCGATAA GTATCTTGTT CTCGGCGACA 6660
6661 CTGTAACTGG CTTGTCATAC AAAAAAACTG GTGTATTTGA TCTAGTTGGC GGTGGATATT 6720
6721 CTGTTGCTTC TATTACTCCT GACAGTTTCC GTAGTACTCG TAAAGGTATA TTTGGTCGTT 6780
6781 CTGAGGACCA AGGCGCAACT TGGATAATGC CTGGTACAAA TGCTGCTCTC TTGTCTGTTC 6840
6841 AAACACAAGC TGATAATAAC AATGCTGGAG ACGGACAAAC CCATATCGGG TACAATGCTG 6900
6901 GCGGTAAAAT GAACCACTAT TTCCGTGGTA CAGGTCAGAT GAATATCAAT ACCCAACAAG 6960
6961 GTATGGAAAT TAACCCGGGT ATTTTGAAAT TGGTAACTGG CTCTAATAAT GTACAATTTT 7020
7021 ACGCTGACGG AACTATTTCT TCCATTCAAC CTATTAAATT AGATAACGAG ATATTTTTAA 7080
7081 CTAAATCTAA TAATACTGCG GGTCTTAAAT TTGGAGCTCC TAGCCAAGTT GATGGCACAA 7140
```

FIG.6C

```
7141  GGACTATCCA ATGGAACGGT GGTACTCGCG AAGGACAGAA TAAAAACTAT GTGATTATTA  7200
7201  AAGCATGGGG TAACTCATTT AATGCCACTG GTGATAGATC TCGCGAAACG GTTTTCCAAG  7260
7261  TATCAGATAG TCAAGGATAT TATTTTTATG CTCATCGTAA AGCTCCAACC GGCGACGAAA  7320
7321  CTATTGGACG TATTGAAGCT CAATTTGCTG GGGATGTTTA TGCTAAAGGT ATTATTGCCA  7380
7381  ACGGAAATTT TAGAGTTGTT GGGTCAAGCG CTTTAGCCGG CAATGTTACT ATGTCTAACG  7440
7441  GTTTGTTTGT CCAAGGTGGT TCTTCTATTA CTGGACAAGT TAAAATTGGC GGAACAGCAA  7500
7501  ACGCACTGAG AATTTGGAAC GCTGAATATG GTGCTATTTT CCGTCGTTCG GAAAGTAACT  7560
7561  TTTATATTAT TCCAACCAAT CAAAATGAAG GAGAAAGTGG AGACATTCAC AGCTCTTTGA  7620
7621  GACCTGTGAG AATAGGATTA AACGATGGCA TGGTTGGGTT AGGAAGAGAT TCTTTTATAG  7680
7681  TAGATCAAAA TAATGCTTTA ACTACGATAA ACAGTAACTC TCGCATTAAT GCCAACTTTA  7740
7741  GAATGCAATT GGGGCAGTCG GCATACATTG ATGCAGAATG TACTGATGCT GTTCGCCCGG  7800
7801  CGGGTGCAGG TTCATTTGCT TCCCAGAATA ATGAAGACGT CCGTGCGCCG TTCTATATGA  7860
7861  ATATTGATAG AACTGATGCT AGTGCATATG TTCCTATTTT GAAACAACGT TATGTTCAAG  7920
7921  GCAATGGCTG CTATTCATTA GGGACTTTAA TTAATAATGG TAATTTCCGA GTTCATTACC  7980
7981  ATGGCGGCGG AGATAACGGT TCTACAGGTC CACAGACTGC TGATTTTGGA TGGGAATTTA  8040
8041  TTAAAAACGG TGATTTTATT TCACCTCGCG ATTTAATAGC AGGCAAAGTC AGATTTGATA  8100
8101  GAACTGGTAA TATCACTGGT GGTTCTGGTA ATTTTGCTAA CTTAAACAGT ACAATTGAAT  8160
8161  CACTTAAAAC TGATATCATG TCGAGTTACC CAATTGGTGC TCCGATTCCT TGGCCGAGTG  8220
8221  ATTCAGTTCC TGCTGGATTT GCTTTGATGG AAGGTCAGAC CTTTGATAAG TCCGCATATC  8280
8281  CAAAGTTAGC TGTTGCATAT CCTAGCGGTG TTATTCCAGA TATGCGCGGG CAAACTATCA  8340
8341  AGGGTAAACC AAGTGGTCGT GCTGTTTTGA GCGCTGAGGC AGATGGTGTT AAGGCTCATA  8400
8401  GCCATAGTGC ATCGGCTTCA AGTACTGACT TAGGTACTAA AACCACATCA AGCTTTGACT  8460
8461  ATGGTACGAA GGGAACTAAC AGTACGGGTG GACACACTCA CTCTGGTAGT GGTTCTACTA  8520
8521  GCACAAATGG TGAGCACAGC CACTACATCG AGGCATGGAA TGGTACTGGT GTAGGTGGTA  8580
8581  ATAAGATGTC ATCATATGCC ATATCATACA GGGCGGGTGG GAGTAACACT AATGCAGCAG  8640
8641  GGAACCACAG TCACACTTTC TCTTTTGGGA CTAGCAGTGC TGGCGACCAT TCCCACTCTG  8700
8701  TAGGTATTGG TGCTCATACC CACACGGTAG CAATTGGATC ACATGGTCAT ACTATCACTG  8760
8761  TAAATAGTAC AGGTAATACA GAAAACACGG TTAAAAACAT TGCTTTTAAC TATATCGTTC  8820
8821  GTTTAGCATA AGGAGAGGGG CTTCGGCCCT TCTAA                               8855
           |   10     |   20     |   30      |   40     |   50     |   60
```

FIG.6D

|   |   |   |   |   |   |   |   |   |   |   |   |   |
|---|---|---|---|---|---|---|---|---|---|---|---|---|
| 1 | TAGGAGCCCGGGAGA | ATG | GCC | GAG | ATT | AAA | AGA | GAA | TTC | AGA | GCA | GAA | GAT | GGT | CTG | GAC | GCA | 63 |
| 1 |  | M | A | E | I | K | R | E | F | R | A | E | D | G | L | D | A | 16 |
| 64 | GGT | GGT | GAT | AAA | ATA | ATC | AAC | GTA | GCT | TTA | GCT | GAT | CGT | ACC | GTA | GGA | ACT | GAC | GGT | GTT | 123 |
| 17 | G | G | D | K | I | I | N | V | A | L | A | D | R | T | V | G | T | D | G | V | 36 |
| 124 | AAC | GTT | GAT | TAC | TTA | ATT | CAA | GAA | AAC | ACA | GTT | CAA | CAG | TAT | GAT | CCA | ACT | CGT | GGA | TAT | 183 |
| 37 | N | V | D | Y | L | I | Q | E | N | T | V | Q | Q | Y | D | P | T | R | G | Y | 56 |
| 184 | TTA | AAA | GAT | TTT | GTA | ATC | ATT | TAT | GAT | AAC | CGC | TTT | TGG | GCT | GCT | ATA | AAT | GAT | ATT | CCA | 243 |
| 57 | L | K | D | F | V | I | I | Y | D | N | R | F | W | A | A | I | N | D | I | P | 76 |
| 244 | AAA | CCA | GCA | GGA | GCT | TTT | AAT | AGC | GGA | CGC | TGG | AGA | GCA | TTA | AAA | TCT | GGT | GAA | GCA | ATT | CCG | GTT | ACC | GAT | GCT | AAC | TGG | 303 |
| 77 | K | P | A | G | A | F | N | S | G | R | W | R | A | L | K | S | G | E | A | I | P | V | T | D | A | N | W | 96 |
| 304 | ATT | ACG | GTT | TCA | TCT | GGT | TCA | TAT | CAA | TTA | AAA | TCT | GGT | GAA | GCA | ATT | TCG | GTT | AAC | ACC | 363 |
| 97 | I | T | V | S | S | G | S | Y | Q | L | K | S | G | E | A | I | S | V | N | T | 116 |
| 364 | GCA | GCT | GGA | AAT | GAC | ATC | ACC | TTT | ACT | TTA | CCA | TCT | TCT | CCA | ATT | GAT | GGT | GAT | ACT | ATC | 423 |
| 117 | A | A | G | N | D | I | T | F | T | L | P | S | S | P | I | D | G | D | T | I | 136 |
| 424 | GTT | CTC | CAA | GAT | ATT | GGA | GGA | AAA | CCT | GGA | GTT | AAC | CAA | GTT | TTA | ATT | GTA | GCT | CCA | GTA | 483 |
| 137 | V | L | Q | D | I | G | G | K | P | G | V | N | Q | V | L | I | V | A | P | V | 156 |
| 484 | CAA | AGT | ATT | GTA | AAC | TTT | AGA | GGT | GAA | CAG | CGT | TCA | GTA | CTA | ATG | ACT | CAT | CCA | AAG | 543 |
| 157 | Q | S | I | V | N | F | R | G | E | Q | R | S | V | L | M | T | H | P | K | 176 |

FIG.7A

| | | | | | | | | | | | | | | | | | | | | |
|---|---|---|---|---|---|---|---|---|---|---|---|---|---|---|---|---|---|---|---|---|
| 544 | TCA | CAC | CTA | GTT | TTA | ATT | TTT | AGT | AAT | CGT | CTC | TGG | CAA | ATG | TAT | GTT | GCT | GAT | TAT | AGT | 603 |
| 177 | S | Q | L | V | L | I | F | S | N | R | L | W | Q | M | Y | V | A | D | Y | S | 196 |
| 604 | AGA | GAA | GCT | ATA | GTT | GTA | ACA | CCA | AAT | ACT | TAT | CAA | GCG | CAA | TCC | AAC | GAT | TTT | ATC | | 663 |
| 197 | R | E | A | I | V | V | T | P | N | T | Y | Q | A | Q | S | N | D | F | I | | 216 |
| 664 | GTA | CGT | AGA | TTT | ACT | TCT | GCT | GCA | CCA | ATT | AAT | GTC | AAA | CTT | CCA | AGA | TTT | GCT | AAT | CAT | 723 |
| 217 | V | R | R | F | T | S | A | A | P | I | N | V | K | L | P | R | F | A | N | H | 236 |
| 724 | GGC | GAT | ATT | ATT | AAT | TTC | GTC | GAT | TTA | GAT | AAA | CTA | AAT | CCG | CTT | TAT | CAT | ACA | ATT | GTT | 783 |
| 237 | G | D | I | I | N | F | V | D | L | D | K | L | N | P | L | Y | H | T | I | V | 256 |
| 784 | ACT | ACA | TAC | GAT | GAA | ACG | ACT | TCA | GTA | CAA | GAA | GTT | GGA | ACT | CAT | TCC | ATT | GAA | GGC | CGT | 843 |
| 257 | T | T | Y | D | E | T | T | S | V | Q | E | V | G | T | H | S | I | E | G | R | 276 |
| 844 | ACA | TCG | ATT | GAC | GGT | TTC | TTG | ATG | TTT | GAT | GAT | AAT | GAG | AAA | TTA | TGG | AGA | CTG | TTT | GAC | 903 |
| 277 | T | S | I | D | G | F | L | M | F | D | D | N | E | K | L | W | R | L | F | D | 296 |
| 904 | GGG | GAT | AGT | AAA | GCG | CGT | TTA | CGT | ATC | ATA | ACG | ACT | AAT | TCA | AAC | ATT | CGT | CCA | AAT | GAA | 963 |
| 297 | G | D | S | K | A | R | L | R | I | I | T | T | N | S | N | I | R | P | N | E | 316 |
| 964 | GAA | GTT | ATG | GTA | TTT | GGT | GCC | AAT | AAC | GGA | ACA | ACT | CAA | ACT | CAA | ACA | ATT | GAG | CTT | AAG | CTT | CCA | 1023 |
| 317 | E | V | M | V | F | G | A | N | N | G | T | T | Q | T | Q | T | I | E | L | K | L | P | 336 |
| 1024 | ACT | AAT | ATT | TCT | GTT | GAT | ACT | GTT | AAA | ATT | TCC | ATG | AAT | TAC | ATG | AGA | AAA | GGA | CAA | 1083 |
| 337 | T | N | I | S | V | D | T | V | K | I | S | M | N | Y | M | R | K | G | Q | 356 |

FIG.7B

```
1084  ACA GTT AAA ATC AAA GCT GCT GAT GAA GAT AAA ATT GCT TCT TCA GTT CAA TTG CTG CAA  1143
 357   T   V   K   I   K   A   A   D   E   D   K   I   A   S   S   V   Q   L   L   Q   376

1144  TTC CCA AAA CGC TCA GAA TAT CCA CCT GAA GCT GAA TGG GTT ACA GTT CAA GAA TTA GTT  1203
 377   F   P   K   R   S   E   Y   P   P   E   A   E   W   V   T   V   Q   E   L   V   396

1204  TTT AAC GAT GAA ACT AAT TAT GTT CCA GTT TTG GAG CTT GCT TAC ATA GAA GAT TCT GAT  1263
 397   F   N   D   E   T   N   Y   V   P   V   L   E   L   A   Y   I   E   D   S   D   416

1264  GTA CAG CAA AAC GTT CCA ACT GTA GAA AGA GTA GAT TCT TTA AAT  1323
 417   G   K   Y   W   V   V   Q   Q   N   V   P   T   V   E   R   V   D   S   L   N   436

1324  GAT TCT ACT AGA GCA AGA TTA GGC GTA ATT GCT TTA GCA ATT ACT CAA CAA GCT CAA AAT GTC  1383
 437   D   S   T   R   A   R   L   G   V   I   A   L   A   T   Q   Q   A   Q   N   V   456

1384  GAT TTA GAA AAT TCT CCA CAA AAA GAA TTA GCA ATT ACT CCA GAA ACC TTA GCT AAT CCT  1443
 457   D   L   E   N   S   P   Q   K   E   L   A   I   T   P   E   T   L   A   N   R   476

1444  ACT GCT ACA GAA ACT CGC AGA GGT ATT GCA AGA ATA ACT ATC ACT CCT AAA AAC CTG AAT GAA CAG  1503
 477   T   A   T   E   T   R   R   G   I   A   R   I   T   I   T   P   K   K   L   N   Q   496

1504  AAC ACC ACA TTC TCT TTT GCT GAT GAT ATT ATC ATC ACT CCT AAA AAC CTG AAT GAA AGA  1563
 497   N   T   T   F   S   F   A   D   D   I   I   I   T   P   K   K   L   N   E   R   516

1564  ACT GCT ACA GAA ACT CGT AGA GGT GTC GCA GAA ATT GCT ACG CAG CAA GAA ACT AAT GCA  1623
 517   T   A   T   E   T   R   R   G   V   A   E   I   A   T   Q   Q   E   T   N   A   536
```

FIG.7C

```
1624 GGA ACC GAT GAT ACT ACA ATC ATC ACT CCT AAA AAG CTT CAA GCT CGT CAA GGT TCT GAA 1683
 537  G   T   D   D   T   T   I   I   T   P   K   K   L   Q   A   R   Q   G   S   E   556

1684 TCA TTA TCT GGT ATT GTA ACC TTT GTA TCT ACT GCA GGT GCT ACT CCA GCT TCT AGC CGT 1743
 557  S   L   S   G   I   V   T   F   V   S   T   A   G   A   T   P   A   S   S   R   576

1744 GAA TTA AAT GGT ACG AAT GTT TAT AAT AAA AAC ACT GAT AAT TTA GTT GTT TCA CCT AAA 1803
 577  E   L   N   G   T   N   V   Y   N   K   N   T   D   N   L   V   V   S   P   K   596

1804 GCT TTG GAT CAG TAT AAA GCT ACT CCA ACA CAG CAA CCT ACT CAA CAG GCA GTA ATT TTA GCA GTT GAA 1863
 597  A   L   D   Q   Y   K   A   T   P   T   Q   Q   P   T   Q   Q   G   A   V   I   L   A   V   E   616

1864 AGT GAA GTT ATT GCT GGA CAA AGT CAG CAA GGA TGG GCA AAT GCT GTT GTA ACG CCA GAA 1923
 617  S   E   V   I   A   G   Q   S   Q   Q   G   W   A   N   A   V   V   T   P   E   636

1924 ACG TTA CAT AAA AAC ACA GGA CGT GAT GGT CGT ATA GGT CTC ATT GAA ATT GCT ACG CAA 1983
 637  T   L   H   K   K   T   S   T   D   G   R   I   G   L   I   E   I   A   T   Q   656

1984 AGT GAA GTT AAT ACA GGA ACT GAA AGT TTA AGT GGT ATA GCT GAA ATT GCT ACA CAA GTT GAA TTC GAC 2043
 657  S   E   V   N   T   G   T   D   Y   T   R   A   V   T   P   K   T   L   N   D   676

2044 CGT AGA GCA ACT GAA TCA CTT TCT GGT ATA GCT GAA ATT GCT ACA CAA GTT GAA TTC GAC 2103
 677  R   R   A   T   E   S   L   S   G   I   A   E   I   A   T   Q   V   E   F   D   696

2104 GCA GGC GTC GAC GAT ACT CGT ATC TCT ACA CCA TTA AAA ATT AAA ACC AGA TTT AAT AGT 2163
 697  A   G   V   D   D   T   R   I   S   T   P   L   K   I   K   T   R   F   N   S   716
```

FIG.7D

```
2164 ACT GAT CGT ACT TCT GTT GTT GCT CTA TCT GGA TTA GTT GAA TCA GGA ACT CTC TGG GAC 2223
717   T   D   R   T   S   V   V   A   L   S   G   L   V   E   S   G   T   L   W   D   736

2224 CAT TAT ACA CTT AAT ATT CTT GAA GCA AAT GAG ACA CAA CCT GGT ACA CTT CGT GTA GCT 2283
737   H   Y   T   L   N   I   L   E   A   N   E   T   Q   R   G   T   L   R   V   A   756

2284 ACG CAG GTC GAA GCT GCT GCG GGA ACA TTA GAT AAT GTT TTA ATA ACT CCT AAA AAG CTT 2343
757   T   Q   V   E   A   A   A   G   T   L   D   N   V   L   I   T   P   K   K   L   776

2344 TTA GGT ACT AAA TCT ACT GAA GCG CAA GAG GGT GTT ATT AAA GTT GCA ACT CAG TCT GAA 2403
777   L   G   T   K   S   T   E   A   Q   E   G   V   I   K   V   A   T   Q   S   E   796

2404 ACT GTG ACT GGA ACG TCA GCA AAT ACT GCT ACT GTA TCT CCA AAA AAT TTA AAA TGG ATT GCC 2463
797   T   V   T   G   T   S   A   N   T   A   T   V   S   P   K   N   L   K   W   I   A   816

2464 CAG AGT GAA CCT ACT TGG GCA GCT ACA ATA AGA GGT TTT GTT AAA ACT TCA TCT 2523
817   Q   S   E   P   T   W   A   A   T   I   R   G   F   V   K   T   S   S   836

2524 GGT TCA ATT ACA TTC GTT GGT AAT GAT ACA GTC GGT TCT ACC CAA GAT TTA GAA CTG TAT 2583
837   G   S   I   T   F   V   G   N   D   T   V   G   S   T   Q   D   L   E   L   Y   856

2584 GAG AAA AAT AGC TAT GCG GTA TCA CCA TAT GAA TTA AAC CGT GTA TTA GCA AAT TAT TTG 2643
857   E   K   N   S   Y   A   V   S   P   Y   E   L   N   R   V   L   A   N   Y   L   876

2644 CCA CTA AAA GCA AAA GCT GCT GAT ACA AAT TTA TTG GAT GGT CTA GAT TCA TCT CAG TTC 2703
877   P   L   K   A   K   A   A   D   T   N   L   L   D   G   L   D   S   S   Q   F   896
```

FIG.7E

| | | | | | | | | | | | | | | | | | | | | | |
|---|---|---|---|---|---|---|---|---|---|---|---|---|---|---|---|---|---|---|---|---|---|
| 2704 | ATT | CGT | AGG | GAT | ATT | GCA | CAG | ACG | GTT | AAT | GGT | TCA | CTA | ACC | TTA | ACC | CAA | CAA | ACG | AAT | 2763 |
| 897 | I | R | R | D | I | A | Q | T | V | N | G | S | L | T | L | T | Q | Q | T | N | 916 |
| 2764 | CTG | AGT | GCC | CCT | CTT | GTA | TCA | TCT | AGT | ACT | GGT | GAA | TTT | GGT | GGT | TCA | TTG | GCC | GCT | AAT | 2823 |
| 917 | L | S | A | P | L | V | S | S | S | T | G | E | F | G | G | S | L | A | A | N | 936 |
| 2824 | AGA | ACA | TTT | ACC | ATC | CGT | AAT | ACA | GGA | GCC | CCG | ACT | AGT | ATC | GTT | TTC | GAA | AAA | GGT | CCT | 2883 |
| 937 | R | T | F | T | I | R | N | T | G | A | P | T | S | I | V | F | E | K | G | P | 956 |
| 2884 | GCA | TCC | GGG | GCA | AAT | CCT | GCA | CAG | TCA | ATG | AGT | ATT | CGT | GTA | TGG | GGT | AAC | CAA | TTT | GGC | 2943 |
| 957 | A | S | G | A | N | P | A | Q | S | M | S | I | R | V | W | G | N | Q | F | G | 976 |
| 2944 | GGC | AGT | GAT | ACG | ACC | CGT | TCG | ACA | GTG | TTT | GAA | GTT | GGC | GAT | GAC | ACA | TCT | CAT | CAC | 3003 |
| 977 | G | G | S | D | T | T | R | S | T | V | F | E | V | G | D | D | T | S | H | H | 996 |
| 3004 | TTT | TAT | TCT | CAA | CGT | AAT | AAA | GAC | GGT | AAT | ATA | GCC | TTT | AAC | ATT | AAT | GGT | ACT | GTA | ATG | 3063 |
| 997 | F | Y | S | Q | R | N | K | D | G | N | I | A | F | N | I | N | G | T | V | M | 1016 |
| 3064 | CCA | ATA | AAC | ATT | AAT | GCT | TCC | GGT | TTG | ATG | AAT | GTG | AAT | GGC | ACT | GCA | ACA | TTC | GGT | CGT | 3123 |
| 1017 | P | I | N | I | N | A | S | G | L | M | N | V | N | G | T | A | T | F | G | R | 1036 |
| 3124 | TCA | GTT | ACA | GCC | AAT | GGT | GAA | TTC | ATC | AGC | AAG | TCT | GCA | AAT | GCT | TTT | AGA | GCA | ATA | AAC | 3183 |
| 1037 | S | V | T | A | N | G | E | F | I | S | K | S | A | N | A | F | R | A | I | N | 1056 |
| 3184 | GGT | GAT | TAC | GGA | TTC | TTT | ATT | CGT | AAT | GAT | GCC | TCT | AAT | ACC | TAT | TTT | TTG | CTC | ACT | GCA | 3243 |
| 1057 | G | D | Y | G | F | F | I | R | N | D | A | S | N | T | Y | F | L | L | T | A | 1076 |

FIG. 7F

```
3244 GCC GGT GAT CAG ACT GGT GGT TTT AAT GGA TTA CGC CCA TTA TTA ATT AAT AAT CAA TCC 3303
1077  A   G   D   Q   T   G   G   F   N   G   L   R   P   L   L   I   N   N   Q   S  1096

3304 GGT CAG ATT ACA GAA GGC TTA ATC ATT GCC AAA GGT GTT ACT ATA AAT TCA GGC 3363
1097  G   Q   I   T   E   G   L   I   I   A   K   G   V   T   I   N   S   G  1116

3364 GGT TTA ACT GTT AAC TCG AGA ATT CGT TCT CAG GGT ACT AAA ACA TCT GAT TTA TAT ACC 3423
1117  G   L   T   V   N   S   R   I   R   S   Q   G   T   K   T   S   D   L   Y   T  1136

3424 CGT GCG CCA ACA TCT GAT ACT GTA GGA TTC TGG TCA ATC GAT ATT AAT GAT TCA GCC ACT 3483
1137  R   A   P   T   S   D   T   V   G   F   W   S   I   D   I   N   D   S   A   T  1156

3484 TAT AAC CAG TTC CCG GGT TAT TTT AAA ATG GTT GAA AAA ACT AAT GAA GTG ACT GGG CTT 3543
1157  Y   N   Q   F   P   G   Y   F   K   M   V   E   K   T   N   E   V   T   G   L  1176

3544 CCA TAC TTA GAA CGT GGC GAA GTT AAA TCT CCT GGT ACA CTG ACT CAG TTT GGT AAC 3603
1177  P   Y   L   E   R   G   E   E   V   K   S   P   G   T   L   T   Q   F   G   N  1196

3604 ACA CTT GAT TCG CTT TAC CAA GAT TGG ATT ACT TAT CCA AAA AAC TCT TGG TCA AGT CGT ACC 3663
1197  T   L   D   S   L   Y   Q   D   W   I   T   Y   P   K   N   S   W   S   S   R   T  1216

3664 ACT CGC TGG ACA CGT ACA TGG CAG ACC AAA ACC TCT TGG TCA AGT TTT GTT CAG GTA 3723
1217  T   R   W   T   R   T   W   Q   K   T   N   S   W   S   S   F   V   Q   V  1236

3724 TTT GAC GGA AAC CCT CCT CAA CCG CAG CCA TCT GAT ATC GGT GCT TTA CCA TCT GAT AAT GCT 3783
1237  F   D   G   N   P   P   Q   P   Q   P   S   D   I   G   A   L   P   S   D   N   A  1256
```

FIG. 7G

```
3784 ACA ATG GGG AAT CTT ACT ATT CGT GAT TTC TTG CGA ATT GGT AAT GTT CGC ATT GTT CCT  3843
1257  T   M   G   N   L   T   I   R   D   F   L   R   I   G   N   V   R   I   V   P   1276

3844 GAC CCA GTG AAT AAA ACG GTT AAA TTT GAA TGG GTT GAA TAA GAGGTATT ATG GAA AAA TTT  3905
1277  D   P   V   N   K   T   V   K   F   E   W   V   E   *            M   E   K   F    4

3906 ATG GCC GAG ATT TGG ACA AGG ATA TGT CCA AAC GCC ATT TTA TCG GAA AGT AAT TCA GTA  3965
  5   M   A   E   I   W   T   R   I   C   P   N   A   I   L   S   E   S   N   S   V    24

3966 AGA TAT AAA ATA AGT ATA GCC GGT TCT TGC CCC CTT TCT ACA GCA GGA CCA TCA TAT GTT  4025
 25   R   Y   K   I   S   I   A   G   S   C   P   L   S   T   A   G   P   S   Y   V    44

4026 AAA TTT CAG GAT AAT CCT GTA GGA AGT CAA ACA TTT AGG CGC AGG CCT TCA TTT AAG AGT  4085
 45   K   F   Q   D   N   P   V   G   S   Q   T   F   R   R   R   P   S   F   K   S    64

4086 TTT TGA CCCTTCCACCGGAGCATTAGTTGATAGTAAGTCAT ATG CTT TTT CGA CTT CAA ATG ATA CTA  4153
 65   F   *                                      M   L   F   R   L   Q   M   I   L     9

4154 CAT CAG CTG CTT TTG TTA GTT TTC ATG AAT TCT TTG ACG AAT AAT CGA ATT GTT GCT ATA  4213
 10   H   Q   L   L   L   L   V   F   M   N   S   L   T   N   N   R   I   V   A   I    29

4214 TTA ACT AGT GGA AAG GTT AAT TTT CCT CCT GAA GTA GTA TCT TGG TTA AGA ACC GCC GGA  4273
 30   L   T   S   G   K   V   N   F   P   P   E   V   V   S   W   L   R   T   A   G    49

4274 ACG TCT GCC TTT CCA TCT GAT TCT ATA TTG TCA AGA TTT GAC GTA TCA TAT GCT GCT TTT  4333
 50   T   S   A   F   P   S   D   S   I   L   S   R   F   D   V   S   Y   A   A   F    69
```

FIG. 7H

```
4334  TAT ACT TCT TCT AAA AGA GCT ATC GCA TTA GAG CAT GTT AAA CTG AGT AAT AGA AAA AGC  4393
 70    Y   T   S   S   K   R   A   I   A   L   E   H   V   K   L   S   N   R   K   S    89

4394  ACA GAT GAT TAT CAA ACT ATT TTA GAT GTT GTA TTT GAC AGT TTA GAA GAT GTA GGA GCT  4453
 90    T   D   D   Y   Q   T   I   L   D   V   V   F   D   S   L   E   D   V   G   A   109

4454  ACC GGG TTT CCA AGA AGA ACC TAT GAA AGT GTT GAG CAA TTC ATG TCG GCA GTT GGT GGA  4513
110    T   G   F   P   R   R   T   Y   E   S   V   E   Q   F   M   S   A   V   G   G   129

4514  ACT AAT AAC GAA ATT GCC AGA TTG CCA ACT TCA GCT GCT ATA AGT AAA TTA TCT GAT TAT  4573
130    T   N   N   E   I   A   R   L   P   T   S   A   A   I   S   K   L   S   D   Y   149

4574  AAT TTA ATT CCT GGA GAT GTT CTT TAT CTT AAA GCT CAG TTA TAT GCT GAT GCT GAT TTA  4633
150    N   L   I   P   G   D   V   L   Y   L   K   A   Q   L   Y   A   D   A   D   L   169

4634  CTT GCT CTT GGA ACT ACA AAT ATA TCT CGT TTT TAT AAT GCA TCT AAC GGA TAT ATT  4693
170    L   A   L   G   T   T   N   I   S   I   R   F   Y   N   A   S   N   G   Y   I   189

4694  TCT TCA ACA CAA GCT GAA TTT ACT GGG CAA GCT GGT TCA TGG GAA TTA AAG GAA GAT TAT  4753
190    S   S   T   Q   A   E   F   T   G   Q   A   G   S   W   E   L   K   E   D   Y   209

4754  GTA GTT GTT CCA GAA AAC GCA GTA GGA TTT ACG ATA TAC GCA CAG AGA ACT GCA CAA GCT  4813
210    V   V   V   P   E   N   A   V   G   F   T   I   Y   A   Q   R   T   A   Q   A   229

4814  GGC CAA GGT GGC ATG AGA AAT TTA AGC TTT TCT GAA GTA TCA AGA AAT GGC GGC ATT TCG  4873
230    G   Q   G   G   M   R   N   L   S   F   S   E   V   S   R   N   G   G   I   S   249
```

FIG. 71

```
4874 AAA CCT GCT GAA TTT GGC GTC AAT GGT ATT CGT GTT AAT TAT ATC TGC GAA TCC GCT TCA   4933
 250  K   P   A   E   F   G   V   N   G   I   R   V   N   Y   I   C   E   S   A   S    269

4934 CCT CCG GAT ATA ATG CTA CCT ACG CAA GCA TCG TCT AAA ACT GGT AAA GTG TTT GGG        4993
 270  P   P   D   I   M   V   L   P   T   Q   A   S   S   K   T   G   K   V   F   G    289

4994 CAA GAA TTT AGA GAA GTT TAA ATTGAGGGACCCTCGGGTTCCCTTTTCTTCTTTATAATACTATTCAAATAAA   5066
 290  Q   E   F   R   E   V   *                                                         296

5067 GGGCATACA ATG GCT GAT TTA AAA GTA GGT TCA ACA ACT GGA GGC TCT GTC ATT TGG CAT      5127
   1           M   A   D   L   K   V   G   S   T   T   G   G   S   V   I   W   H       17

5128 CAA GGA AAT TTT CCA TTG AAT CCA GCC GGT GAC GAT GTA CTC TAT AAA TCA TTT AAA ATA    5187
  18  Q   G   N   F   P   L   N   P   A   G   D   D   V   L   Y   K   S   F   K   I     37

5188 TAT TCA GAA TAT AAC AAA CCA CAA GCT GCT GAT AAC GAT TTC GTT TCT AAA GCT AAT GGT    5247
  38  Y   S   E   Y   N   K   P   Q   A   A   D   N   D   F   V   S   K   A   N   G     57

5248 GGT ACT TAT GCA TCA AAG GTA ACA TTT AAC GCT GGC ATT CAA GTC CCA TAT GCT CCA AAC    5307
  58  G   T   Y   A   S   K   V   T   F   N   A   G   I   Q   V   P   Y   A   P   N     77

5308 ATC ATG AGC CCA TGC TGC GGG ATT TAT GGG GGT AAC GGT GAT GGT GCA ACT TTT GAT AAA GCA 5367
  78  I   M   S   P   C   C   G   I   Y   G   G   N   G   D   G   A   T   F   D   K   A   97

5368 AAT ATC GAT ATT GTT TCA TGG TAT GGC GTA GGA TTT AAA TCG TCA TTT GGT TCA ACA GGC    5427
  98  N   I   D   I   V   S   W   Y   G   V   G   F   K   S   S   F   G   S   T   G    117
```

FIG.7J

```
5428  CGA ACT GTT GTA ATT AAT ACA CGC AAT GGT GAT ATT AAC ACA AAA GGT GTT GTG TCG GCA  5487
118    R   T   V   V   I   N   T   R   N   G   D   I   N   T   K   G   V   V   S   A   137

5488  GCT GGT CAA GTA AGA AGT GGT GCC GCT CCT ATA GCA GCG AAT GAC CTT ACT AGA AAC      5547
138    A   G   Q   V   R   S   G   A   A   P   I   A   A   N   D   L   T   R   K       157

5548  GAC TAT GTT GAT GGA GCA ATA AAT ACT GTT ACT GCA AAT TCT AGG GTG CTA CGG          5607
158    D   Y   V   D   G   A   I   N   T   V   T   A   N   S   R   V   L   R           177

5608  TCT GGT GAC ACC ATG ACA GGT AAT TTA ACA GCG CCA AAC TTT TTC TCG CAG AAT CCT GCA  5667
178    S   G   D   T   M   T   G   N   L   T   A   P   N   F   F   S   Q   N   P   A   197

5668  TCT CAA CCC TCA CAC GTT CCA CGA TTT GAC CAA ATC GTA ATT AAG GAT TCT GTT CAA GAT  5727
198    S   Q   P   S   H   V   P   R   F   D   Q   I   V   I   K   D   S   V   Q   D   217

5728  TTC GGC TAT TAT TAA GAGGACTT ATG GCT ACT TTA AAA CAA ATA CAA TTT AAA AGA AGC AAA  5789
218    F   G   Y   Y   *                M   A   T   L   K   Q   I   Q   F   K   R   S   K   13

5790  ATC GCA GGA ACA CCT GCT GCT TCA GTA TTA GCC GAA GGT GAA TTG GCT ATA AAC TTA      5849
14     I   A   G   T   P   A   A   S   V   L   A   E   G   E   L   A   I   N   L       33

5850  AAA GAT AGA ACA ATT TTT ACT AAA GAT GAT TCA GGA AAT ATC ATC GAT CTA GGT TTT GCT  5909
34     K   D   R   T   I   F   T   K   D   D   S   G   N   I   I   D   L   G   F   A   81

5910  AAA GCC GGG CAA GTT GAT GGC AAC GTT ACT ATT AAC GGA CTT TTG AGA TTA AAT GGC GAT  5969
54     K   G   G   Q   V   D   G   N   V   T   I   N   G   L   L   R   L   N   G   D   73
```

FIG.7K

```
5970  TAT GTA CAA ACA GGT GGA ATG ACT GTA AAC GGA CCC ATT GGT TCT ACT GAT GGC GTC ACT  6029
 74    Y   V   Q   T   G   G   M   T   V   N   G   P   I   G   S   T   D   G   V   T    93

6030  GGA AAA ATT TTC AGA TCT ACA CAG GGT TCA TTT TAT GCA AGA GCA ACA AAC GAT ACT TCA  6089
 94    G   K   I   F   R   S   T   Q   G   S   F   Y   A   R   A   T   N   D   T   S   113

6090  AAT GCC CAT TTA TGG TTT GAA AAT GCC GAT GGC ACT GAA CGT GGC GTT ATA TAT GCT CGC  6149
114    N   A   H   L   W   F   E   N   A   D   G   T   E   R   G   V   I   Y   A   R   133

6150  CCT CAA ACT ACA ACT GAC GGT GAA ATA CCC CTT AGG GTT AGA CAA ACA GGA AGC ACT     6209
134    P   Q   T   T   T   D   G   E   I   R   L   R   V   R   Q   T   G   S   T     153

6210  GCC AAC AGT GAA TTC TAT TTC CGC TCT ATA AAT GGA GGC GAA TTT CAG GCT AAC CGT ATT  6269
154    A   N   S   E   F   Y   F   R   S   I   N   G   G   E   F   Q   A   N   R   I   173

6270  TTA GCA TCA GAT TCG TTA GTA ACA AAA CGC ATT GCG GTT GAT ACC GTT ATT CAT GAT GCC  6329
174    L   A   S   D   S   L   V   T   K   R   I   A   V   D   T   V   I   H   D   A   193

6330  AAA GCA TTT GGA CAA TAT GAT TCT CTT CGT AAA GTT CGC GCT AAG TCC GGT ACA ATT TAT  6389
194    K   A   F   G   Q   Y   D   S   L   R   K   V   R   A   K   S   G   T   I   Y   213

6390  GAA ACA AAT GGT GTA AAC TAT CTT CGT AAG GCT GAT GAA GTT TCT TGG TCT GGT GAT     6449
214    E   T   N   G   V   N   Y   L   R   K   A   D   E   V   S   W   S   G   D     911

6450  CAT GAA ATT GTT ACT GCA CAA ACA GGC CTG GCT GAT GAA GTT TCT TGG TCT GGT GAT     6509
234    H   E   I   V   T   A   Q   T   G   L   A   D   E   V   S   W   S   G   D     253
```

FIG.7L

| | | | | | | | | | | |
|---|---|---|---|---|---|---|---|---|---|---|
| 6510 | ACA | CCA | GTA | TTT | AAA | CTA | TAC | GGT | ATT | CCT | GAC | GAT | GGC | AGA | ATG | ATT | ATC | CCT | AAT | AGC | 6569 |
| 254 | T | P | V | F | K | L | Y | G | I | R | D | D | G | R | M | I | I | R | N | S | 273 |

| 6570 | CTT | GCA | TTA | GGT | ACA | TTC | ACT | ACA | AAT | TTC | CCG | TCT | AGT | GAT | TAT | GGC | AAC | GTC | GGT | GTA | 6629 |
|---|---|---|---|---|---|---|---|---|---|---|---|---|---|---|---|---|---|---|---|---|---|
| 274 | L | A | L | G | T | F | T | T | N | F | P | S | S | D | Y | G | N | V | G | V | 293 |

| 6630 | ATG | GGC | GAT | AAG | TAT | CTT | GTT | CTC | GGC | GAC | ACT | GTA | ACT | GGC | TTG | TCA | TAC | AAA | AAA | ACT | 6689 |
|---|---|---|---|---|---|---|---|---|---|---|---|---|---|---|---|---|---|---|---|---|---|
| 294 | M | G | D | K | Y | L | V | L | G | D | T | V | T | G | L | S | Y | K | K | T | 313 |

| 6690 | GGT | GTA | TTT | GAT | CTA | GTT | GGC | GGT | GGA | TAT | TCT | GTT | GCT | TCT | ATT | ACT | CCT | GAC | AGT | TTC | 6749 |
|---|---|---|---|---|---|---|---|---|---|---|---|---|---|---|---|---|---|---|---|---|---|
| 314 | G | V | F | D | L | V | G | G | G | Y | S | V | A | S | I | T | P | D | S | F | 333 |

| 6750 | CGT | AGT | ACT | CGT | AAA | GGT | ATA | TTT | GGT | CGT | TCT | GTT | CAA | GAC | CAA | GGC | GCA | ACT | TGG | ATA | ATG | 6809 |
|---|---|---|---|---|---|---|---|---|---|---|---|---|---|---|---|---|---|---|---|---|---|
| 334 | R | S | T | R | K | G | I | F | G | R | S | E | D | Q | Q | G | A | T | W | I | M | 353 |

| 6810 | CCT | GGT | ACA | AAT | GCT | GCT | CTC | TTG | TCT | GTT | CAA | ACA | CAA | GCT | GAT | AAT | AAC | AAT | GCT | GGA | 6869 |
|---|---|---|---|---|---|---|---|---|---|---|---|---|---|---|---|---|---|---|---|---|---|
| 354 | P | G | T | N | A | A | L | L | S | V | Q | T | Q | A | D | N | N | N | A | G | 373 |

| 6870 | GAC | GGA | CAA | ACC | CAT | ATC | GGG | TAC | AAT | ATC | AAT | ACC | CAA | CAA | GGT | ATG | GAA | ATT | AAC | CAC | TAT | TTC | CGT | GGT | 6929 |
|---|---|---|---|---|---|---|---|---|---|---|---|---|---|---|---|---|---|---|---|---|---|
| 374 | D | G | Q | T | H | I | G | Y | N | I | N | T | Q | Q | G | M | E | I | N | H | Y | F | R | G | 393 |

| 6930 | ACA | GGT | CAG | ATG | AAT | ATC | AAT | ACC | CAA | CAA | GGT | ATG | GAA | ATT | AAC | CCG | GGT | ATT | TTG | AAA | 6989 |
|---|---|---|---|---|---|---|---|---|---|---|---|---|---|---|---|---|---|---|---|---|---|
| 394 | T | G | Q | M | N | I | N | T | Q | Q | G | M | E | I | N | P | G | I | L | K | 413 |

| 6990 | TTG | GTA | ACT | GGC | TCT | AAT | AAT | GTA | CAA | TTT | TAC | GCT | GAC | GGA | ACT | ATT | TCT | TCC | ATT | CAA | 7049 |
|---|---|---|---|---|---|---|---|---|---|---|---|---|---|---|---|---|---|---|---|---|---|
| 414 | L | V | T | G | S | N | N | V | Q | F | Y | A | D | G | T | I | S | S | I | Q | 433 |

FIG.7M

```
7050 CCT ATT AAA TTA GAT AAC GAG ATA TTT TTA ACT AAA TCT AAT AAT ACT GCC GGT CTT AAA  7109
434  P   I   K   L   D   N   E   I   F   L   T   K   S   N   N   T   A   G   L   K    453

7110 TTT GGA GCT CCT AGC CAA GTT GAT GGC ACA AGG ACT ATC CAA TGG AAC GGT GGT ACT CGC  7169
454  F   G   A   P   S   Q   V   D   G   T   R   T   I   Q   W   N   G   G   T   R    473

7170 GAA GGA CAG AAT AAA AAC TAT GTG ATT ATT AAA GCA TGG GGT AAC TCA TTT AAT GCC ACT  7229
474  E   G   Q   N   K   N   Y   V   I   I   K   A   W   G   N   S   F   N   A   T    493

7230 GGT GAT AGA TCT CGC GAA ACG GTT TTC CAA GTA TCA GAT AGT CAA GGA TAT TAT TTT TAT  7289
494  G   D   R   S   R   E   T   V   F   Q   V   S   D   S   Q   G   Y   Y   F   Y    513

7290 GCT CAT CGT AAA GCT CCA ACC GGC GAC GAA ACT ATT GGA CCT ATT GAA GCT CAA TTT GCT  7349
514  A   H   R   K   A   P   T   G   D   E   T   I   G   R   I   E   A   Q   F   A    533

7350 GGG GAT GTT TAT GCT AAA GGT ATT ATT GCC AAC GGA AAT TTT AGA GTT GTT GGG TCA AGC  7409
534  G   D   V   Y   A   K   G   I   I   A   N   G   N   F   R   V   V   G   S   S    553

7410 GCT TTA GCC AAT GTT ACT ATG TCT AAC GGT TTG TTT GTC CAA GGT GGG TCT TCT ATT      7469
554  A   L   A   N   V   T   M   S   N   G   L   F   V   Q   G   G   S   S   I        573

7470 ACT GGA CAA GTT AAA ATT GGC GGA ACA GCA AAC GCA CTG AGA ATT TGG AAC GCT GAA TAT  7529
574  T   G   Q   V   K   I   G   G   T   A   N   A   L   R   I   W   N   A   E   Y    593

7530 GGT GCT ATT TTC CGT CGT TCG GAA AGT AAC TTT TAT ATT CCA ACC AAT CAA AAT GAA      7589
594  G   A   I   F   R   R   S   E   S   N   F   Y   I   P   T   N   Q   N   E        613
```

FIG.7N

```
7590  GGA GAA AGT GGA GAC ATT CAC AGC TCT TTG AGA CCT GTG AGA ATA GGA TTA AAC GAT GGC  7649
 614   G   E   S   G   D   I   H   S   S   L   R   P   V   R   I   G   L   N   D   G    633

7650  ATG GTT GGG TTA GGA AGA GAT TCT TTT ATA GTA GAT CAA AAT GCT TTA ACT TTA ACG ATA  7709
 634   M   V   G   L   G   R   D   S   F   I   V   D   Q   N   A   L   T   L   T   I    653

7710  AAC AGT AAC TCT CGC ATT AAT GCC AAC TTT AGA ATG CAA TTG GGG CAG TCG GCA TAC ATT  7769
 654   N   S   N   S   R   I   N   A   N   F   R   M   Q   L   G   Q   S   A   Y   I    673

7770  GAT GCA GAA TGT ACT GAT GCT GTT CGC CCG GGT GCA CGT TCA TTT GCT TCC CAG AAT      7829
 674   D   A   E   C   T   D   A   V   R   P   G   A   G   S   F   A   S   Q   N        693

7830  AAT GAA GAC GTC CGT GCC CCG TTC TAT ATG AAT ATT GAT AGA ACT GAT GCT AGT GCA TAT  7889
 694   N   E   D   V   R   A   P   F   Y   M   N   I   D   R   T   D   A   S   A   Y    713

7890  GTT CCT ATT TTG AAA CAA CGT TAT TCA GTT CAT TAC CAT TGC TAT TCA TTA GGG ACT TTA  7949
 714   V   P   I   L   K   Q   R   Y   S   V   H   Y   H   C   Y   S   L   G   T   L    733

7950  ATT AAT AAT GGT AAT TTC CGA GTT CAT TGG GAA TTT ATT AAA AAC GGT GAT TTT ATT TCA CCT CGC  8009
 734   I   N   N   G   N   F   R   V   H   W   E   F   I   K   N   G   D   F   I   S   P   R    753

8010  CCA CAG ACT GCT GAT TTT GGA TGG GAA TTT ATT AAA AAC GGT GAT TTT ATT TCA CCT CGC  8069
 754   P   Q   T   A   D   F   G   W   E   F   I   K   N   G   D   F   I   S   P   R    773

8070  GAT TTA ATA GCA GGC AAA GTC AGA TTT GAT AGA ACT GGT AAT ATC ACT GGT TCT GGT      8129
 774   D   L   I   A   G   K   V   R   F   D   R   T   G   N   I   T   G   S   G        793
```

FIG.70

```
8130  AAT TTT GCT AAC TTA AAC AGT ACA ATT GAA TCA CTT AAA ACT GAT ATC ATG TCG AGT TAC  8180
794    N   F   A   N   L   N   S   T   I   E   S   L   K   T   D   I   M   S   S   Y    813

8190  CCA ATT GGT GCT CCG ATT CCT TGG CCG AGT GAT TCA GTT CCT GGA TTT GCT TTG ATG       8249
814    P   I   G   A   P   I   P   W   P   S   D   S   V   P   G   F   A   L   M        833

8250  GAA GGT CAG ACC TTT GAT AAG TCC GCA TAT CCA AAG TTA GCT GTT GCA TAT CCT AGC GGT  8309
834    E   G   Q   T   F   D   K   S   A   Y   P   K   L   A   V   A   Y   P   S   G    853

8310  GTT ATT CCA GAT ATG CGC GGG CAA ACT ATC AAG GGT CAT AGT AGT GGT CGT GCT GTT TTG  8369
854    V   I   P   D   M   R   G   Q   T   I   K   G   H   S   S   G   R   A   V   L    873

8370  AGC GCT GAG GCA GAT GGT GTT AAG GCT CAT AGC TTT GAC TAT GGT ACG AAG GGA ACT GAC  8429
874    S   A   E   A   D   G   V   K   A   H   S   F   D   Y   G   T   K   G   T   D    893

8430  TTA GGT ACT AAA ACC ACA TCA AGC TTT GAC TAT GGT TCT ACT AGC ACA AAT GGT ACC GGT  8489
894    L   G   T   K   T   T   S   S   F   D   Y   G   S   T   S   T   N   G   T   G    913

8490  GGA CAC ACT CAC TCT AGT GGT GTA GGT ACT AGC ATG TCA TAT GAG CAC AGC CAC TAC ATC  8549
914    G   H   T   H   S   S   G   V   G   T   S   M   S   Y   E   H   S   H   Y   I    933

8550  GAG GCA TGG AAT GGT ACT GGT GTA GGT GGT AAT AAG ATG TCA TCA TAT GCC ATA TCA TAC  8609
934    E   A   W   N   G   T   G   V   G   G   N   K   M   S   S   Y   A   I   S   Y    953

8610  AGG GCC GGT GGG AGT AAC ACT AAT GCA GCA GGG AAC CAC AGT CAC ACT TTC TCT TTT GGG  8669
954    R   A   G   G   S   N   T   N   A   A   G   N   H   S   H   T   F   S   F   G    973
```

FIG.7P

```
8670  ACT AGC AGT GCT GGC GAC CAT TCC CAC TCT GTA GGT ATT GGT GCT CAT ACC CAC ACG GTA  8729
 974    T   S   S   A   G   D   H   S   H   S   V   G   I   G   A   H   T   H   T   V    993

8730  GCA ATT GGA TCA CAT GGT CAT ACT ATC ACT GTA AAT AGT ACA GGT AAT ACA GAA AAC ACG  8789
 994    A   I   G   S   H   G   H   T   I   T   V   N   S   T   G   N   T   E   N   T   1013

8790  GTT AAA AAC ATT GCT TTT AAC TAT ATC GTT CGT TTA GCA TAA GGAGAGGGGCTTCGGCCCTTCTAA  8855
1014    V   K   N   I   A   F   N   Y   I   V   R   L   A   *                            1027
```

FIG.7Q

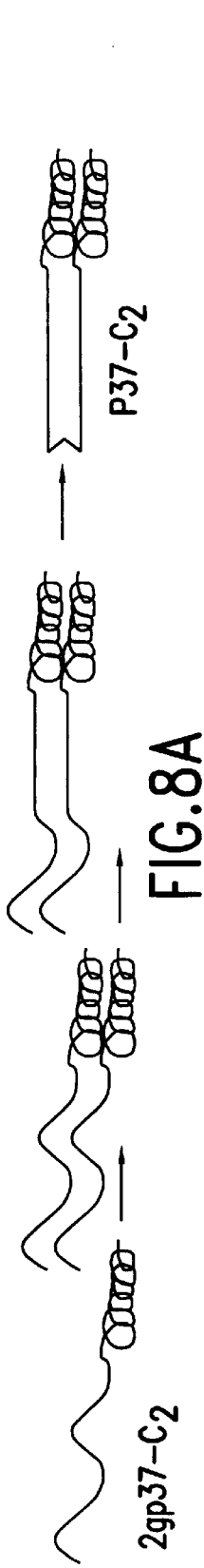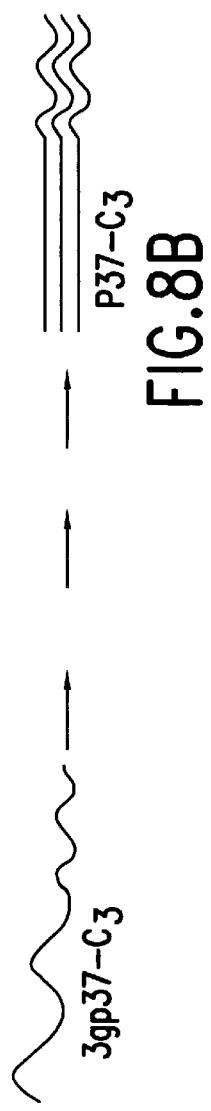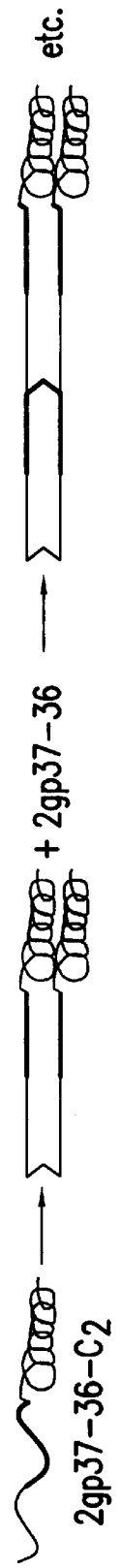

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 8855 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacteriophage T4

( v i i ) IMMEDIATE SOURCE:

(B) CLONE: TAIL FIBER GENES (xi) SEQUENCE DESCRIPTION: SEQ ID NO:1:

| | | | | | | |
|---|---|---|---|---|---|---|
| TAGGAGCCCG | GGAGAATGGC | CGAGATTAAA | AGAGAATTCA | GAGCAGAAGA | TGGTCTGGAC | 60 |
| GCAGGTGGTG | ATAAATAAT | CAACGTAGCT | TTAGCTGATC | GTACCGTAGG | AACTGACGGT | 120 |
| GTTAACGTTG | ATTACTTAAT | TCAAGAAAAC | ACAGTTCAAC | AGTATGATCC | AACTCGTGGA | 180 |
| TATTTAAAAG | ATTTTGTAAT | CATTTATGAT | AACCGCTTTT | GGGCTGCTAT | AAATGATATT | 240 |
| CCAAAACCAG | CAGGAGCTTT | TAATAGCGGA | CGCTGGAGAG | CATTACGTAC | CGATGCTAAC | 300 |
| TGGATTACGG | TTTCATCTGG | TTCATATCAA | TTAAATCTG | GTGAAGCAAT | TTCGGTTAAC | 360 |
| ACCGCAGCTG | GAAATGACAT | CACGTTTACT | TTACCATCTT | CTCCAATTGA | TGGTGATACT | 420 |
| ATCGTTCTCC | AAGATATTGG | AGGAAAACCT | GGAGTTAACC | AAGTTTTAAT | TGTAGCTCCA | 480 |
| GTACAAAGTA | TTGTAAACTT | TAGAGGTGAA | CAGGTACGTT | CAGTACTAAT | GACTCATCCA | 540 |
| AAGTCACAGC | TAGTTTTAAT | TTTTAGTAAT | CGTCTGTGGC | AAATGTATGT | TGCTGATTAT | 600 |
| AGTAGAGAAG | CTATAGTTGT | AACACCAGCG | AATACTTATC | AAGCGCAATC | CAACGATTTT | 660 |
| ATCGTACGTA | GATTTACTTC | TGCTGCACCA | ATTAATGTCA | AACTTCCAAG | ATTTGCTAAT | 720 |
| CATGGCGATA | TTATTAATTT | CGTCGATTTA | GATAAACTAA | ATCCGCTTTA | TCATACAATT | 780 |
| GTTACTACAT | ACGATGAAAC | GACTTCAGTA | CAAGAAGTTG | GAACTCATTC | CATTGAAGGC | 840 |
| CGTACATCGA | TTGACGGTTT | CTTGATGTTT | GATGATAATG | AGAAATTATG | GAGACTGTTT | 900 |
| GACGGGGATA | GTAAAGCGCG | TTTACGTATC | ATAACGACTA | ATTCAAACAT | TCGTCCAAAT | 960 |
| GAAGAAGTTA | TGGTATTTGG | TGCGAATAAC | GGAACAACTC | AAACAATTGA | GCTTAAGCTT | 1020 |
| CCAACTAATA | TTTCTGTTGG | TGATACTGTT | AAAATTTCCA | TGAATTACAT | GAGAAAAGGA | 1080 |
| CAAACAGTTA | AAATCAAAGC | TGCTGATGAA | GATAAAATTG | CTTCTTCAGT | TCAATTGCTG | 1140 |
| CAATTCCCAA | AACGCTCAGA | ATATCCACCT | GAAGCTGAAT | GGGTTACAGT | TCAAGAATTA | 1200 |
| GTTTTTAACG | ATGAAACTAA | TTATGTTCCA | GTTTTGGAGC | TTGCTTACAT | AGAAGATTCT | 1260 |
| GATGGAAAAT | ATTGGGTTGT | ACAGCAAAAC | GTTCCAACTG | TAGAAAGAGT | AGATTCTTTA | 1320 |
| AATGATTCTA | CTAGAGCAAG | ATTAGGCGTA | ATTGCTTTAG | CTACACAAGC | TCAAGCTAAT | 1380 |
| GTCGATTTAG | AAAATTCTCC | ACAAAAGAA | TTAGCAATTA | CTCCAGAAAC | GTTAGCTAAT | 1440 |
| CGTACTGCTA | CAGAAACTCG | CAGAGGTATT | GCAAGAATAG | CAACTACTGC | TCAAGTGAAT | 1500 |
| CAGAACACCA | CATTCTCTTT | TGCTGATGAT | ATTATCATCA | CTCCTAAAAA | GCTGAATGAA | 1560 |
| AGAACTGCTA | CAGAAACTCG | TAGAGGTGTC | GCAGAAATTG | CTACGCAGCA | AGAAACTAAT | 1620 |
| GCAGGAACCG | ATGATACTAC | AATCATCACT | CCTAAAAAGC | TTCAAGCTCG | TCAAGGTTCT | 1680 |
| GAATCATTAT | CTGGTATTGT | AACCTTTGTA | TCTACTGCAG | GTGCTACTCC | AGCTTCTAGC | 1740 |
| CGTGAATTAA | ATGGTACGAA | TGTTTATAAT | AAAAACACTG | ATAATTTAGT | TGTTTCACCT | 1800 |
| AAAGCTTTGG | ATCAGTATAA | AGCTACTCCA | ACACAGCAAG | GTGCAGTAAT | TTTAGCAGTT | 1860 |
| GAAAGTGAAG | TAATTGCTGG | ACAAAGTCAG | CAAGGATGGG | CAAATGCTGT | TGTAACGCCA | 1920 |
| GAAACGTTAC | ATAAAAAGAC | ATCAACTGAT | GGAAGAATTG | GTTTAATTGA | AATTGCTACG | 1980 |
| CAAAGTGAAG | TTAATACAGG | AACTGATTAT | ACTCGTGCAG | TCACTCCTAA | AACTTTAAAT | 2040 |
| GACCGTAGAG | CAACTGAAAG | TTTAAGTGGT | ATAGCTGAAA | TTGCTACACA | AGTTGAATTC | 2100 |
| GACGCAGGCG | TCGACGATAC | TCGTATCTCT | ACACCATTAA | AAATTAAAAC | CAGATTTAAT | 2160 |
| AGTACTGATC | GTACTTCTGT | TGTTGCTCTA | TCTGGATTAG | TTGAATCAGG | AACTCTCTGG | 2220 |
| GACCATTATA | CACTTAATAT | TCTTGAAGCA | AATGAGACAC | AACGTGGTAC | ACTTCGTGTA | 2280 |

| | | | | | | |
|---|---|---|---|---|---|---|
| GCTACGCAGG | TCGAAGCTGC | TGCGGGAACA | TTAGATAATG | TTTTAATAAC | TCCTAAAAAG | 2340 |
| CTTTTAGGTA | CTAAATCTAC | TGAAGCGCAA | GAGGGTGTTA | TTAAAGTTGC | AACTCAGTCT | 2400 |
| GAAACTGTGA | CTGGAACGTC | AGCAAATACT | GCTGTATCTC | CAAAAAATTT | AAAATGGATT | 2460 |
| GCGCAGAGTG | AACCTACTTG | GGCAGCTACT | ACTGCAATAA | GAGGTTTTGT | TAAAACTTCA | 2520 |
| TCTGGTTCAA | TTACATTCGT | TGGTAATGAT | ACAGTCGGTT | CTACCCAAGA | TTTAGAACTG | 2580 |
| TATGAGAAAA | ATAGCTATGC | GGTATCACCA | TATGAATTAA | ACCGTGTATT | AGCAAATTAT | 2640 |
| TTGCCACTAA | AAGCAAAAGC | TGCTGATACA | AATTTATTGG | ATGGTCTAGA | TTCATCTCAG | 2700 |
| TTCATTCGTA | GGGATATTGC | ACAGACGGTT | AATGGTTCAC | TAACCTTAAC | CCAACAAACG | 2760 |
| AATCTGAGTG | CCCCTCTTGT | ATCATCTAGT | ACTGGTGAAT | TGGTGGTTC | ATTGGCCGCT | 2820 |
| AATAGAACAT | TTACCATCCG | TAATACAGGA | GCCCCGACTA | GTATCGTTTT | CGAAAAGGT | 2880 |
| CCTGCATCCG | GGGCAAATCC | TGCACAGTCA | ATGAGTATTC | GTGTATGGGG | TAACCAATTT | 2940 |
| GGCGGCGGTA | GTGATACGAC | CCGTTCGACA | GTGTTTGAAG | TTGGCGATGA | CACATCTCAT | 3000 |
| CACTTTTATT | CTAACGTAA | TAAAGACGGT | AATATAGCGT | TTAACATTAA | TGGTACTGTA | 3060 |
| ATGCCAATAA | ACATTAATGC | TTCCGGTTTG | ATGAATGTGA | ATGGCACTGC | AACATTCGGT | 3120 |
| CGTTCAGTTA | CAGCCAATGG | TGAATTCATC | AGCAAGTCTG | CAAATGCTTT | TAGAGCAATA | 3180 |
| AACGGTGATT | ACGGATTCTT | TATTCGTAAT | GATGCCTCTA | ATACCTATTT | TTTGCTCACT | 3240 |
| GCAGCCGGTG | ATCAGACTGG | TGGTTTTAAT | GGATTACGCC | CATTATTAAT | TAATAATCAA | 3300 |
| TCCGGTCAGA | TTACAATTGG | TGAAGGCTTA | ATCATTGCCA | AAGGTGTTAC | TATAAATTCA | 3360 |
| GGCGGTTTAA | CTGTTAACTC | GAGAATTCGT | TCTCAGGGTA | CTAAAACATC | TGATTTATAT | 3420 |
| ACCCGTGCGC | CAACATCTGA | TACTGTAGGA | TTCTGGTCAA | TCGATATTAA | TGATTCAGCC | 3480 |
| ACTTATAACC | AGTTCCCGGG | TTATTTTAAA | ATGGTTGAAA | AAACTAATGA | AGTGACTGGG | 3540 |
| CTTCCATACT | TAGAACGTGG | CGAAGAAGTT | AAATCTCCTG | GTACACTGAC | TCAGTTTGGT | 3600 |
| AACACACTTG | ATTCGCTTTA | CCAAGATTGG | ATTACTTATC | CAACGACGCC | AGAAGCGCGT | 3660 |
| ACCACTCGCT | GGACACGTAC | ATGGCAGAAA | ACCAAAAACT | CTTGGTCAAG | TTTTGTTCAG | 3720 |
| GTATTTGACG | GAGGTAACCC | TCCTCAACCA | TCTGATATCG | GTGCTTTACC | ATCTGATAAT | 3780 |
| GCTACAATGG | GGAATCTTAC | TATTCGTGAT | TTCTTGCGAA | TTGGTAATGT | TCGCATTGTT | 3840 |
| CCTGACCCAG | TGAATAAAAC | GGTTAAATTT | GAATGGGTTG | AATAAGAGGT | ATTATGGAAA | 3900 |
| AATTTATGGC | CGAGATTTGG | ACAAGGATAT | GTCCAAACGC | CATTTTATCG | GAAAGTAATT | 3960 |
| CAGTAAGATA | TAAAATAAGT | ATAGCGGGTT | CTTGCCCGCT | TTCTACAGCA | GGACCATCAT | 4020 |
| ATGTTAAATT | TCAGGATAAT | CCTGTAGGAA | GTCAAACATT | TAGGCGCAGG | CCTTCATTTA | 4080 |
| AGAGTTTTTG | ACCCTTCCAC | CGGAGCATTA | GTTGATAGTA | AGTCATATGC | TTTTTCGACT | 4140 |
| TCAAATGATA | CTACATCAGC | TGCTTTTGTT | AGTTTTCATG | AATTCTTTGA | CGAATAATCG | 4200 |
| AATTGTTGCT | ATATTAACTA | GTGGAAAGGT | TAATTTTCCT | CCTGAAGTAG | TATCTTGGTT | 4260 |
| AAGAACCGCC | GGAACGTCTG | CCTTTCCATC | TGATTCTATA | TTGTCAAGAT | TGACGTATC | 4320 |
| ATATGCTGCT | TTTTATACTT | CTTCTAAAAG | AGCTATCGCA | TTAGAGCATG | TTAAACTGAG | 4380 |
| TAATAGAAAA | AGCACAGATG | ATTATCAAAC | TATTTTAGAT | GTTGTATTTG | ACAGTTTAGA | 4440 |
| AGATGTAGGA | GCTACCGGGT | TTCCAAGAAG | AACGTATGAA | AGTGTTGAGC | AATTCATGTC | 4500 |
| GGCAGTTGGT | GGAACTAATA | ACGAAATTGC | GAGATTGCCA | ACTTCAGCTG | CTATAAGTAA | 4560 |
| ATTATCTGAT | TATAATTTAA | TTCCTGGAGA | TGTTCTTTAT | CTTAAAGCTC | AGTTATATGC | 4620 |
| TGATGCTGAT | TTACTTGCTC | TTGGAACTAC | AAATATATCT | ATCCGTTTTT | ATAATGCATC | 4680 |

| | | | | | | |
|---|---|---|---|---|---|---|
| TAACGGATAT | ATTTCTTCAA | CACAAGCTGA | ATTACTGGG | CAAGCTGGGT | CATGGGAATT | 4740 |
| AAAGGAAGAT | TATGTAGTTG | TTCCAGAAAA | CGCAGTAGGA | TTTACGATAT | ACGCACAGAG | 4800 |
| AACTGCACAA | GCTGGCCAAG | GTGGCATGAG | AAATTTAAGC | TTTTCTGAAG | TATCAAGAAA | 4860 |
| TGGCGGCATT | TCGAAACCTG | CTGAATTTGG | CGTCAATGGT | ATTCGTGTTA | ATTATATCTG | 4920 |
| CGAATCCGCT | TCACCTCCGG | ATATAATGGT | ACTTCCTACG | CAAGCATCGT | CTAAAACTGG | 4980 |
| TAAAGTGTTT | GGGCAAGAAT | TTAGAGAAGT | TTAAATTGAG | GGACCCTTCG | GGTTCCCTTT | 5040 |
| TTCTTTATAA | ATACTATTCA | AATAAGGGG | CATACAATGG | CTGATTTAAA | AGTAGGTTCA | 5100 |
| ACAACTGGAG | GCTCTGTCAT | TTGGCATCAA | GGAAATTTTC | CATTGAATCC | AGCCGGTGAC | 5160 |
| GATGTACTCT | ATAAATCATT | TAAATATAT | TCAGAATATA | ACAAACCACA | AGCTGCTGAT | 5220 |
| AACGATTTCG | TTTCTAAAGC | TAATGGTGGT | ACTTATGCAT | CAAAGGTAAC | ATTTAACGCT | 5280 |
| GGCATTCAAG | TCCCATATGC | TCCAAACATC | ATGAGCCCAT | GCGGGATTTA | TGGGGTAAC | 5340 |
| GGTGATGGTG | CTACTTTTGA | TAAAGCAAAT | ATCGATATTG | TTTCATGGTA | TGGCGTAGGA | 5400 |
| TTTAAATCGT | CATTTGGTTC | AACAGGCCGA | ACTGTTGTAA | TTAATACACG | CAATGGTGAT | 5460 |
| ATTAACACAA | AAGGTGTTGT | GTCGGCAGCT | GGTCAAGTAA | GAAGTGGTGC | GGCTGCTCCT | 5520 |
| ATAGCAGCGA | ATGACCTTAC | TAGAAAGGAC | TATGTTGATG | GAGCAATAAA | TACTGTTACT | 5580 |
| GCAAATGCAA | ACTCTAGGGT | GCTACGGTCT | GGTGACACCA | TGACAGGTAA | TTTAACAGCG | 5640 |
| CCAAACTTTT | TCTCGCAGAA | TCCTGCATCT | CAACCCTCAC | ACGTTCCACG | ATTTGACCAA | 5700 |
| ATCGTAATTA | AGGATTCTGT | TCAAGATTTC | GGCTATTATT | AAGAGGACTT | ATGGCTACTT | 5760 |
| TAAAACAAAT | ACAATTTAAA | AGAAGCAAAA | TCGCAGGAAC | ACGTCCTGCT | GCTTCAGTAT | 5820 |
| TAGCCGAAGG | TGAATTGGCT | ATAAACTTAA | AAGATAGAAC | AATTTTTACT | AAAGATGATT | 5880 |
| CAGGAAATAT | CATCGATCTA | GGTTTTGCTA | AAGGCGGGCA | AGTTGATGGC | AACGTTACTA | 5940 |
| TTAACGGACT | TTTGAGATTA | AATGGCGATT | ATGTACAAAC | AGGTGGAATG | ACTGTAAACG | 6000 |
| GACCCATTGG | TTCTACTGAT | GGCGTCACTG | GAAAAATTTT | CAGATCTACA | CAGGGTTCAT | 6060 |
| TTTATGCAAG | AGCAACAAAC | GATACTTCAA | ATGCCCATTT | ATGGTTTGAA | AATGCCGATG | 6120 |
| GCACTGAACG | TGGCGTTATA | TATGCTCGCC | CTCAAACTAC | AACTGACGGT | GAAATACGCC | 6180 |
| TTAGGGTTAG | ACAAGGAACA | GGAAGCACTG | CCAACAGTGA | ATTCTATTTC | CGCTCTATAA | 6240 |
| ATGGAGGCGA | ATTTCAGGCT | AACCGTATTT | TAGCATCAGA | TTCGTTAGTA | ACAAAACGCA | 6300 |
| TTGCGGTTGA | TACCGTTATT | CATGATGCCA | AAGCATTTGG | ACAATATGAT | TCTCACTCTT | 6360 |
| TGGTTAATTA | TGTTTATCCT | GGAACCGGTG | AAACAAATGG | TGTAAACTAT | CTTCGTAAAG | 6420 |
| TTCGCGCTAA | GTCCGGTGGT | ACAATTTATC | ATGAAATTGT | TACTGCACAA | ACAGGCCTGG | 6480 |
| CTGATGAAGT | TTCTTGGTGG | TCTGGTGATA | CACCAGTATT | TAAACTATAC | GGTATTCGTG | 6540 |
| ACGATGGCAG | AATGATTATC | CGTAATAGCC | TTGCATTAGG | TACATTCACT | ACAAATTTCC | 6600 |
| CGTCTAGTGA | TTATGGCAAC | GTCGGTGTAA | TGGGCGATAA | GTATCTTGTT | CTCGGCGACA | 6660 |
| CTGTAACTGG | CTTGTCATAC | AAAAAAACTG | GTGTATTTGA | TCTAGTTGGC | GGTGGATATT | 6720 |
| CTGTTGCTTC | TATTACTCCT | GACAGTTTCC | GTAGTACTCG | TAAAGGTATA | TTTGGTCGTT | 6780 |
| CTGAGGACCA | AGGCGCAACT | TGGATAATGC | CTGGTACAAA | TGCTGCTCTC | TTGTCTGTTC | 6840 |
| AAACACAAGC | TGATAATAAC | AATGCTGGAG | ACGGACAAAC | CCATATCGGG | TACAATGCTG | 6900 |
| GCGGTAAAAT | GAACCACTAT | TTCCGTGGTA | CAGGTCAGAT | GAATATCAAT | ACCCAACAAG | 6960 |
| GTATGGAAAT | TAACCCGGGT | ATTTTGAAAT | TGGTAACTGG | CTCTAATAAT | GTACAATTTT | 7020 |
| ACGCTGACGG | AACTATTTCT | TCCATTCAAC | CTATTAAATT | AGATAACGAG | ATATTTTAA | 7080 |

| | | | | | |
|---|---|---|---|---|---|
| CTAAATCTAA | TAATACTGCG | GGTCTTAAAT | TTGGAGCTCC | TAGCCAAGTT | GATGGCACAA 7140 |
| GGACTATCCA | ATGGAACGGT | GGTACTCGCG | AAGGACAGAA | TAAAAACTAT | GTGATTATTA 7200 |
| AAGCATGGGG | TAACTCATTT | AATGCCACTG | GTGATAGATC | TCGCGAAACG | GTTTTCCAAG 7260 |
| TATCAGATAG | TCAAGGATAT | TATTTTTATG | CTCATCGTAA | AGCTCCAACC | GGCGACGAAA 7320 |
| CTATTGGACG | TATTGAAGCT | CAATTGCTG | GGGATGTTTA | TGCTAAAGGT | ATTATTGCCA 7380 |
| ACGGAAATTT | TAGAGTTGTT | GGGTCAAGCG | CTTTAGCCGG | CAATGTTACT | ATGTCTAACG 7440 |
| GTTTGTTTGT | CCAAGGTGGT | TCTTCTATTA | CTGGACAAGT | TAAAATTGGC | GGAACAGCAA 7500 |
| ACGCACTGAG | AATTTGGAAC | GCTGAATATG | GTGCTATTTT | CCGTCGTTCG | GAAAGTAACT 7560 |
| TTTATATTAT | TCCAACCAAT | CAAATGAAG | GAGAAAGTGG | AGACATTCAC | AGCTCTTTGA 7620 |
| GACCTGTGAG | AATAGGATTA | AACGATGGCA | TGGTTGGGTT | AGGAAGAGAT | TCTTTTATAG 7680 |
| TAGATCAAAA | TAATGCTTTA | ACTACGATAA | ACAGTAACTC | TCGCATTAAT | GCCAACTTTA 7740 |
| GAATGCAATT | GGGGCAGTCG | GCATACATTG | ATGCAGAATG | TACTGATGCT | GTTCGCCCGG 7800 |
| CGGGTGCAGG | TTCATTTGCT | TCCCAGAATA | ATGAAGACGT | CCGTGCGCCG | TTCTATATGA 7860 |
| ATATTGATAG | AACTGATGCT | AGTGCATATG | TTCCTATTTT | GAAACAACGT | TATGTTCAAG 7920 |
| GCAATGGCTG | CTATTCATTA | GGGACTTTAA | TTAATAATGG | TAATTTCCGA | GTTCATTACC 7980 |
| ATGGCGGCGG | AGATAACGGT | TCTACAGGTC | CACAGACTGC | TGATTTTGGA | TGGGAATTTA 8040 |
| TTAAAAACGG | TGATTTTATT | TCACCTCGCG | ATTAATAGC | AGGCAAAGTC | AGATTTGATA 8100 |
| GAACTGGTAA | TATCACTGGT | GGTTCTGGTA | ATTTTGCTAA | CTTAAACAGT | ACAATTGAAT 8160 |
| CACTTAAAAC | TGATATCATG | TCGAGTTACC | CAATTGGTGC | TCCGATTCCT | TGGCCGAGTG 8220 |
| ATTCAGTTCC | TGCTGGATTT | GCTTTGATGG | AAGGTCAGAC | CTTTGATAAG | TCCGCATATC 8280 |
| CAAAGTTAGC | TGTTGCATAT | CCTAGCGGTG | TTATTCCAGA | TATGCGCGGG | CAAACTATCA 8340 |
| AGGGTAAACC | AAGTGGTCGT | GCTGTTTTGA | GCGCTGAGGC | AGATGGTGTT | AAGGCTCATA 8400 |
| GCCATAGTGC | ATCGGCTTCA | AGTACTGACT | TAGGTACTAA | AACCACATCA | AGCTTTGACT 8460 |
| ATGGTACGAA | GGGAACTAAC | AGTACGGGTG | GACACACTCA | CTCTGGTAGT | GGTTCTACTA 8520 |
| GCACAAATGG | TGAGCACAGC | CACTACATCG | AGGCATGGAA | TGGTACTGGT | GTAGGTGGTA 8580 |
| ATAAGATGTC | ATCATATGCC | ATATCATACA | GGGCGGGTGG | GAGTAACACT | AATGCAGCAG 8640 |
| GGAACCACAG | TCACACTTTC | TCTTTTGGGA | CTAGCAGTGC | TGGCGACCAT | TCCCACTCTG 8700 |
| TAGGTATTGG | TGCTCATACC | CACACGGTAG | CAATTGGATC | ACATGGTCAT | ACTATCACTG 8760 |
| TAAATAGTAC | AGGTAATACA | GAAAACACGG | TTAAAAACAT | TGCTTTTAAC | TATATCGTTC 8820 |
| GTTTAGCATA | AGGAGAGGGG | CTTCGGCCCT | TCTAA | | 8855 |

( 2 ) INFORMATION FOR SEQ ID NO:2:

( i ) SEQUENCE CHARACTERISTICS:
        ( A ) LENGTH: 1289 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Bacteriophage T4

( v i i ) IMMEDIATE SOURCE:
        ( B ) CLONE: p34 amino acid ( x i ) SEQUENCE DESCRIPTION: SEQ ID NO:2:

Met  Ala  Glu  Ile  Lys  Arg  Glu  Phe  Arg  Ala  Glu  Asp  Gly  Leu  Asp  Ala
    1             5                   10                 15

```
Gly Gly Asp Lys Ile Ile Asn Val Ala Leu Ala Asp Arg Thr Val Gly
            20              25                      30
Thr Asp Gly Val Asn Val Asp Tyr Leu Ile Gln Glu Asn Thr Val Gln
        35              40                  45
Gln Tyr Asp Pro Thr Arg Gly Tyr Leu Lys Asp Phe Val Ile Ile Tyr
    50              55                  60
Asp Asn Arg Phe Trp Ala Ala Ile Asn Asp Ile Pro Lys Pro Ala Gly
65              70                  75                      80
Ala Phe Asn Ser Gly Arg Trp Arg Ala Leu Arg Thr Asp Ala Asn Trp
            85                  90                      95
Ile Thr Val Ser Ser Gly Ser Tyr Gln Leu Lys Ser Gly Glu Ala Ile
            100             105                 110
Ser Val Asn Thr Ala Ala Gly Asn Asp Ile Thr Phe Thr Leu Pro Ser
        115             120                 125
Ser Pro Ile Asp Gly Asp Thr Ile Val Leu Gln Asp Ile Gly Gly Lys
    130             135                 140
Pro Gly Val Asn Gln Val Leu Ile Val Ala Pro Val Gln Ser Ile Val
145             150                 155                     160
Asn Phe Arg Gly Glu Gln Val Arg Ser Val Leu Met Thr His Pro Lys
                165             170                 175
Ser Gln Leu Val Leu Ile Phe Ser Asn Arg Leu Trp Gln Met Tyr Val
            180             185                 190
Ala Asp Tyr Ser Arg Glu Ala Ile Val Val Thr Pro Ala Asn Thr Tyr
        195             200                 205
Gln Ala Gln Ser Asn Asp Phe Ile Val Arg Arg Phe Thr Ser Ala Ala
    210             215                 220
Pro Ile Asn Val Lys Leu Pro Arg Phe Ala Asn His Gly Asp Ile Ile
225             230                 235                     240
Asn Phe Val Asp Leu Asp Lys Leu Asn Pro Leu Tyr His Thr Ile Val
                245             250                 255
Thr Thr Tyr Asp Glu Thr Thr Ser Val Gln Glu Val Gly Thr His Ser
            260             265                 270
Ile Glu Gly Arg Thr Ser Ile Asp Gly Phe Leu Met Phe Asp Asp Asn
        275             280                 285
Glu Lys Leu Trp Arg Leu Phe Asp Gly Asp Ser Lys Ala Arg Leu Arg
    290             295                 300
Ile Ile Thr Thr Asn Ser Asn Ile Arg Pro Asn Glu Glu Val Met Val
305             310                 315                     320
Phe Gly Ala Asn Asn Gly Thr Thr Gln Thr Ile Glu Leu Lys Leu Pro
                325             330                 335
Thr Asn Ile Ser Val Gly Asp Thr Val Lys Ile Ser Met Asn Tyr Met
            340             345                 350
Arg Lys Gly Gln Thr Val Lys Ile Lys Ala Ala Asp Glu Asp Lys Ile
        355             360                 365
Ala Ser Ser Val Gln Leu Leu Gln Phe Pro Lys Arg Ser Glu Tyr Pro
    370             375                 380
Pro Glu Ala Glu Trp Val Thr Val Gln Glu Leu Val Phe Asn Asp Glu
385             390                 395                     400
Thr Asn Tyr Val Pro Val Leu Glu Leu Ala Tyr Ile Glu Asp Ser Asp
                405             410                 415
Gly Lys Tyr Trp Val Val Gln Gln Asn Val Pro Thr Val Glu Arg Val
            420             425                 430
Asp Ser Leu Asn Asp Ser Thr Arg Ala Arg Leu Gly Val Ile Ala Leu
```

|   |   |   | 435 |   |   |   |   | 440 |   |   |   |   | 445 |   |   |
|---|---|---|---|---|---|---|---|---|---|---|---|---|---|---|---|
| Ala | Thr | Gln | Ala | Gln | Ala | Asn | Val | Asp | Leu | Glu | Asn | Ser | Pro | Gln | Lys |
|   | 450 |   |   |   | 455 |   |   |   |   | 460 |   |   |   |   |   |
| Glu | Leu | Ala | Ile | Thr | Pro | Glu | Thr | Leu | Ala | Asn | Arg | Thr | Ala | Thr | Glu |
| 465 |   |   |   |   | 470 |   |   |   |   | 475 |   |   |   |   | 480 |
| Thr | Arg | Arg | Gly | Ile | Ala | Arg | Ile | Ala | Thr | Ala | Gln | Val | Asn | Gln |   |
|   |   |   |   | 485 |   |   |   |   | 490 |   |   |   |   | 495 |   |
| Asn | Thr | Thr | Phe | Ser | Phe | Ala | Asp | Asp | Ile | Ile | Ile | Thr | Pro | Lys | Lys |
|   |   |   |   | 500 |   |   |   | 505 |   |   |   |   |   | 510 |   |
| Leu | Asn | Glu | Arg | Thr | Ala | Thr | Glu | Thr | Arg | Arg | Gly | Val | Ala | Glu | Ile |
|   |   |   | 515 |   |   |   |   | 520 |   |   |   |   | 525 |   |   |
| Ala | Thr | Gln | Gln | Glu | Thr | Asn | Ala | Gly | Thr | Asp | Asp | Thr | Thr | Ile | Ile |
|   | 530 |   |   |   |   | 535 |   |   |   |   | 540 |   |   |   |   |
| Thr | Pro | Lys | Lys | Leu | Gln | Ala | Arg | Gln | Gly | Ser | Glu | Ser | Leu | Ser | Gly |
| 545 |   |   |   |   | 550 |   |   |   |   | 555 |   |   |   |   | 560 |
| Ile | Val | Thr | Phe | Val | Ser | Thr | Ala | Gly | Ala | Thr | Pro | Ala | Ser | Ser | Arg |
|   |   |   |   | 565 |   |   |   |   | 570 |   |   |   |   | 575 |   |
| Glu | Leu | Asn | Gly | Thr | Asn | Val | Tyr | Asn | Lys | Asn | Thr | Asp | Asn | Leu | Val |
|   |   |   | 580 |   |   |   |   | 585 |   |   |   |   | 590 |   |   |
| Val | Ser | Pro | Lys | Ala | Leu | Asp | Gln | Tyr | Lys | Ala | Thr | Pro | Thr | Gln | Gln |
|   |   | 595 |   |   |   |   | 600 |   |   |   |   | 605 |   |   |   |
| Gly | Ala | Val | Ile | Leu | Ala | Val | Glu | Ser | Glu | Val | Ile | Ala | Gly | Gln | Ser |
|   | 610 |   |   |   |   | 615 |   |   |   |   | 620 |   |   |   |   |
| Gln | Gln | Gly | Trp | Ala | Asn | Ala | Val | Val | Thr | Pro | Glu | Thr | Leu | His | Lys |
| 625 |   |   |   |   | 630 |   |   |   |   | 635 |   |   |   |   | 640 |
| Lys | Thr | Ser | Thr | Asp | Gly | Arg | Ile | Gly | Leu | Ile | Glu | Ile | Ala | Thr | Gln |
|   |   |   |   | 645 |   |   |   |   | 650 |   |   |   |   | 655 |   |
| Ser | Glu | Val | Asn | Thr | Gly | Thr | Asp | Tyr | Thr | Arg | Ala | Val | Thr | Pro | Lys |
|   |   |   | 660 |   |   |   |   | 665 |   |   |   |   | 670 |   |   |
| Thr | Leu | Asn | Asp | Arg | Arg | Ala | Thr | Glu | Ser | Leu | Ser | Gly | Ile | Ala | Glu |
|   |   |   | 675 |   |   |   |   | 680 |   |   |   |   | 685 |   |   |
| Ile | Ala | Thr | Gln | Val | Glu | Phe | Asp | Ala | Gly | Val | Asp | Asp | Thr | Arg | Ile |
|   | 690 |   |   |   |   | 695 |   |   |   |   | 700 |   |   |   |   |
| Ser | Thr | Pro | Leu | Lys | Ile | Lys | Thr | Arg | Phe | Asn | Ser | Thr | Asp | Arg | Thr |
| 705 |   |   |   |   | 710 |   |   |   |   | 715 |   |   |   |   | 720 |
| Ser | Val | Val | Ala | Leu | Ser | Gly | Leu | Val | Glu | Ser | Gly | Thr | Leu | Trp | Asp |
|   |   |   |   | 725 |   |   |   |   | 730 |   |   |   |   | 735 |   |
| His | Tyr | Thr | Leu | Asn | Ile | Leu | Glu | Ala | Asn | Glu | Thr | Gln | Arg | Gly | Thr |
|   |   |   | 740 |   |   |   |   | 745 |   |   |   |   | 750 |   |   |
| Leu | Arg | Val | Ala | Thr | Gln | Val | Glu | Ala | Ala | Ala | Gly | Thr | Leu | Asp | Asn |
|   |   | 755 |   |   |   |   | 760 |   |   |   |   | 765 |   |   |   |
| Val | Leu | Ile | Thr | Pro | Lys | Lys | Leu | Leu | Gly | Thr | Lys | Ser | Thr | Glu | Ala |
|   | 770 |   |   |   |   | 775 |   |   |   |   | 780 |   |   |   |   |
| Gln | Glu | Gly | Val | Ile | Lys | Val | Ala | Thr | Gln | Ser | Glu | Thr | Val | Thr | Gly |
| 785 |   |   |   |   | 790 |   |   |   |   | 795 |   |   |   |   | 800 |
| Thr | Ser | Ala | Asn | Thr | Ala | Val | Ser | Pro | Lys | Asn | Leu | Lys | Trp | Ile | Ala |
|   |   |   |   | 805 |   |   |   |   | 810 |   |   |   |   | 815 |   |
| Gln | Ser | Glu | Pro | Thr | Trp | Ala | Ala | Thr | Thr | Ala | Ile | Arg | Gly | Phe | Val |
|   |   |   | 820 |   |   |   |   | 825 |   |   |   |   | 830 |   |   |
| Lys | Thr | Ser | Ser | Gly | Ser | Ile | Thr | Phe | Val | Gly | Asn | Asp | Thr | Val | Gly |
|   |   | 835 |   |   |   |   | 840 |   |   |   |   | 845 |   |   |   |
| Ser | Thr | Gln | Asp | Leu | Glu | Leu | Tyr | Glu | Lys | Asn | Ser | Tyr | Ala | Val | Ser |
|   | 850 |   |   |   |   | 855 |   |   |   |   | 860 |   |   |   |   |

```
Pro  Tyr  Glu  Leu  Asn  Arg  Val  Leu  Ala  Asn  Tyr  Leu  Pro  Leu  Lys  Ala
865                      870                     875                     880

Lys  Ala  Ala  Asp  Thr  Asn  Leu  Leu  Asp  Gly  Leu  Asp  Ser  Ser  Gln  Phe
                    885                     890                     895

Ile  Arg  Arg  Asp  Ile  Ala  Gln  Thr  Val  Asn  Gly  Ser  Leu  Thr  Leu  Thr
               900                     905                     910

Gln  Gln  Thr  Asn  Leu  Ser  Ala  Pro  Leu  Val  Ser  Ser  Thr  Gly  Glu
          915                     920                     925

Phe  Gly  Gly  Ser  Leu  Ala  Ala  Asn  Arg  Thr  Phe  Thr  Ile  Arg  Asn  Thr
          930                     935                     940

Gly  Ala  Pro  Thr  Ser  Ile  Val  Phe  Glu  Lys  Gly  Pro  Ala  Ser  Gly  Ala
945                      950                     955                     960

Asn  Pro  Ala  Gln  Ser  Met  Ser  Ile  Arg  Val  Trp  Gly  Asn  Gln  Phe  Gly
                    965                     970                     975

Gly  Gly  Ser  Asp  Thr  Thr  Arg  Ser  Thr  Val  Phe  Glu  Val  Gly  Asp  Asp
               980                     985                     990

Thr  Ser  His  His  Phe  Tyr  Ser  Gln  Arg  Asn  Lys  Asp  Gly  Asn  Ile  Ala
               995                     1000                    1005

Phe  Asn  Ile  Asn  Gly  Thr  Val  Met  Pro  Ile  Asn  Ile  Asn  Ala  Ser  Gly
          1010                    1015                    1020

Leu  Met  Asn  Val  Asn  Gly  Thr  Ala  Thr  Phe  Gly  Arg  Ser  Val  Thr  Ala
1025                     1030                    1035                    1040

Asn  Gly  Glu  Phe  Ile  Ser  Lys  Ser  Ala  Asn  Ala  Phe  Arg  Ala  Ile  Asn
               1045                    1050                    1055

Gly  Asp  Tyr  Gly  Phe  Phe  Ile  Arg  Asn  Asp  Ala  Ser  Asn  Thr  Tyr  Phe
               1060                    1065                    1070

Leu  Leu  Thr  Ala  Ala  Gly  Asp  Gln  Thr  Gly  Gly  Phe  Asn  Gly  Leu  Arg
               1075                    1080                    1085

Pro  Leu  Leu  Ile  Asn  Asn  Gln  Ser  Gly  Gln  Ile  Thr  Ile  Gly  Glu  Gly
     1090                    1095                    1100

Leu  Ile  Ile  Ala  Lys  Gly  Val  Thr  Ile  Asn  Ser  Gly  Gly  Leu  Thr  Val
1105                     1110                    1115                    1120

Asn  Ser  Arg  Ile  Arg  Ser  Gln  Gly  Thr  Lys  Thr  Ser  Asp  Leu  Tyr  Thr
                    1125                    1130                    1135

Arg  Ala  Pro  Thr  Ser  Asp  Thr  Val  Gly  Phe  Trp  Ser  Ile  Asp  Ile  Asn
                    1140                    1145                    1150

Asp  Ser  Ala  Thr  Tyr  Asn  Gln  Phe  Pro  Gly  Tyr  Phe  Lys  Met  Val  Glu
               1155                    1160                    1165

Lys  Thr  Asn  Glu  Val  Thr  Gly  Leu  Pro  Tyr  Leu  Glu  Arg  Gly  Glu  Glu
          1170                    1175                    1180

Val  Lys  Ser  Pro  Gly  Thr  Leu  Thr  Gln  Phe  Gly  Asn  Thr  Leu  Asp  Ser
1185                     1190                    1195                    1200

Leu  Tyr  Gln  Asp  Trp  Ile  Thr  Tyr  Pro  Thr  Thr  Pro  Glu  Ala  Arg  Thr
                    1205                    1210                    1215

Thr  Arg  Trp  Thr  Arg  Thr  Trp  Gln  Lys  Thr  Lys  Asn  Ser  Trp  Ser  Ser
                    1220                    1225                    1230

Phe  Val  Gln  Val  Phe  Asp  Gly  Gly  Asn  Pro  Pro  Gln  Pro  Ser  Asp  Ile
               1235                    1240                    1245

Gly  Ala  Leu  Pro  Ser  Asp  Asn  Ala  Thr  Met  Gly  Asn  Leu  Thr  Ile  Arg
               1250                    1255                    1260

Asp  Phe  Leu  Arg  Ile  Gly  Asn  Val  Arg  Ile  Val  Pro  Asp  Pro  Val  Asn
1265                     1270                    1275                    1280

Lys  Thr  Val  Lys  Phe  Glu  Trp  Val  Glu
                    1285
```

(2) INFORMATION FOR SEQ ID NO:3:

(i) SEQUENCE CHARACTERISTICS:
        (A) LENGTH: 65 amino acids
        (B) TYPE: amino acid
        (D) TOPOLOGY: linear (ii) MOLECULE TYPE: protein (vi) ORIGINAL SOURCE:
        (A) ORGANISM: Bacteriophage T4

(vii) IMMEDIATE SOURCE:
        (B) CLONE: ORF X amino acid (xi) SEQUENCE DESCRIPTION: SEQ ID NO:3:

```
Met Glu Lys Phe Met Ala Glu Ile Trp Thr Arg Ile Cys Pro Asn Ala
 1               5                  10                  15
Ile Leu Ser Glu Ser Asn Ser Val Arg Tyr Lys Ile Ser Ile Ala Gly
                20                  25                  30
Ser Cys Pro Leu Ser Thr Ala Gly Pro Ser Tyr Val Lys Phe Gln Asp
            35                  40                  45
Asn Pro Val Gly Ser Gln Thr Phe Arg Arg Arg Pro Ser Phe Lys Ser
    50                  55                  60
Phe
65
```

(2) INFORMATION FOR SEQ ID NO:4:

(i) SEQUENCE CHARACTERISTICS:
        (A) LENGTH: 295 amino acids
        (B) TYPE: amino acid
        (D) TOPOLOGY: linear (ii) MOLECULE TYPE: protein (vi) ORIGINAL SOURCE:
        (A) ORGANISM: Bacteriophage T4

(vii) IMMEDIATE SOURCE:
        (B) CLONE: p35 amino acid (xi) SEQUENCE DESCRIPTION: SEQ ID NO:4:

```
Met Leu Phe Arg Leu Gln Met Ile Leu His Gln Leu Leu Leu Leu Val
 1               5                  10                  15
Phe Met Asn Ser Leu Thr Asn Asn Arg Ile Val Ala Ile Leu Thr Ser
                20                  25                  30
Gly Lys Val Asn Phe Pro Pro Glu Val Val Ser Trp Leu Arg Thr Ala
            35                  40                  45
Gly Thr Ser Ala Phe Pro Ser Asp Ser Ile Leu Ser Arg Phe Asp Val
    50                  55                  60
Ser Tyr Ala Ala Phe Tyr Thr Ser Ser Lys Arg Ala Ile Ala Leu Glu
65                  70                  75                  80
His Val Lys Leu Ser Asn Arg Lys Ser Thr Asp Asp Tyr Gln Thr Ile
                85                  90                  95
Leu Asp Val Val Phe Asp Ser Leu Glu Asp Val Gly Ala Thr Gly Phe
            100                 105                 110
Pro Arg Arg Thr Tyr Glu Ser Val Glu Gln Phe Met Ser Ala Val Gly
        115                 120                 125
Gly Thr Asn Asn Glu Ile Ala Arg Leu Pro Thr Ser Ala Ala Ile Ser
    130                 135                 140
Lys Leu Ser Asp Tyr Asn Leu Ile Pro Gly Asp Val Leu Tyr Leu Lys
```

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |

Ala Gln Leu Tyr Ala Asp Ala Asp Leu Leu Ala Leu Gly Thr Thr Asn
                    165                 170                 175

Ile Ser Ile Arg Phe Tyr Asn Ala Ser Asn Gly Tyr Ile Ser Ser Thr
            180                 185                 190

Gln Ala Glu Phe Thr Gly Gln Ala Gly Ser Trp Glu Leu Lys Glu Asp
        195                 200                 205

Tyr Val Val Pro Glu Asn Ala Val Gly Phe Thr Ile Tyr Ala Gln
    210                 215                 220

Arg Thr Ala Gln Ala Gly Gln Gly Gly Met Arg Asn Leu Ser Phe Ser
225                 230                 235                 240

Glu Val Ser Arg Asn Gly Gly Ile Ser Lys Pro Ala Glu Phe Gly Val
            245                 250                 255

Asn Gly Ile Arg Val Asn Tyr Ile Cys Glu Ser Ala Ser Pro Pro Asp
            260                 265                 270

Ile Met Val Leu Pro Thr Gln Ala Ser Ser Lys Thr Gly Lys Val Phe
        275                 280                 285

Gly Gln Glu Phe Arg Glu Val
290                 295

(2) INFORMATION FOR SEQ ID NO:5:

(i) SEQUENCE CHARACTERISTICS:
        (A) LENGTH: 221 amino acids
        (B) TYPE: amino acid
        (D) TOPOLOGY: linear (ii) MOLECULE TYPE: protein (vi) ORIGINAL SOURCE:
        (A) ORGANISM: Bacteriophage T4

(vii) IMMEDIATE SOURCE:
        (B) CLONE: p36 amino acid (xi) SEQUENCE DESCRIPTION: SEQ ID NO:5:

Met Ala Asp Leu Lys Val Gly Ser Thr Thr Gly Gly Ser Val Ile Trp
1               5                   10                  15

His Gln Gly Asn Phe Pro Leu Asn Pro Ala Gly Asp Asp Val Leu Tyr
            20                  25                  30

Lys Ser Phe Lys Ile Tyr Ser Glu Tyr Asn Lys Pro Gln Ala Ala Asp
        35                  40                  45

Asn Asp Phe Val Ser Lys Ala Asn Gly Gly Thr Tyr Ala Ser Lys Val
    50                  55                  60

Thr Phe Asn Ala Gly Ile Gln Val Pro Tyr Ala Pro Asn Ile Met Ser
65                  70                  75                  80

Pro Cys Gly Ile Tyr Gly Gly Asn Gly Asp Gly Ala Thr Phe Asp Lys
                85                  90                  95

Ala Asn Ile Asp Ile Val Ser Trp Tyr Gly Val Gly Phe Lys Ser Ser
            100                 105                 110

Phe Gly Ser Thr Gly Arg Thr Val Val Ile Asn Thr Arg Asn Gly Asp
        115                 120                 125

Ile Asn Thr Lys Gly Val Val Ser Ala Ala Gly Gln Val Arg Ser Gly
    130                 135                 140

Ala Ala Ala Pro Ile Ala Ala Asn Asp Leu Thr Arg Lys Asp Tyr Val
145                 150                 155                 160

Asp Gly Ala Ile Asn Thr Val Thr Ala Asn Ala Asn Ser Arg Val Leu
                165                 170                 175

-continued

```
Arg  Ser  Gly  Asp  Thr  Met  Thr  Gly  Asn  Leu  Thr  Ala  Pro  Asn  Phe  Phe
              180                      185                      190

Ser  Gln  Asn  Pro  Ala  Ser  Gln  Pro  Ser  His  Val  Pro  Arg  Phe  Asp  Gln
          195                      200                      205

Ile  Val  Ile  Lys  Asp  Ser  Val  Gln  Asp  Phe  Gly  Tyr  Tyr
     210                      215                      220
```

(2) INFORMATION FOR SEQ ID NO:6:

(i) SEQUENCE CHARACTERISTICS:
        (A) LENGTH: 1026 amino acids
        (B) TYPE: amino acid
        (D) TOPOLOGY: linear (ii) MOLECULE TYPE: protein (vi) ORIGINAL SOURCE:
        (A) ORGANISM: Bacteriophage T4

(vii) IMMEDIATE SOURCE:
        (B) CLONE: p37 amino acid (xi) SEQUENCE DESCRIPTION: SEQ ID NO:6:

```
Met  Ala  Thr  Leu  Lys  Gln  Ile  Gln  Phe  Lys  Arg  Ser  Lys  Ile  Ala  Gly
1                   5                       10                      15

Thr  Arg  Pro  Ala  Ala  Ser  Val  Leu  Ala  Glu  Gly  Glu  Leu  Ala  Ile  Asn
               20                      25                      30

Leu  Lys  Asp  Arg  Thr  Ile  Phe  Thr  Lys  Asp  Asp  Ser  Gly  Asn  Ile  Ile
          35                      40                      45

Asp  Leu  Gly  Phe  Ala  Lys  Gly  Gln  Val  Asp  Gly  Asn  Val  Thr  Ile
     50                      55                      60

Asn  Gly  Leu  Leu  Arg  Leu  Asn  Gly  Asp  Tyr  Val  Gln  Thr  Gly  Gly  Met
65                       70                      75                       80

Thr  Val  Asn  Gly  Pro  Ile  Gly  Ser  Thr  Asp  Gly  Val  Thr  Gly  Lys  Ile
               85                      90                      95

Phe  Arg  Ser  Thr  Gln  Gly  Ser  Phe  Tyr  Ala  Arg  Ala  Thr  Asn  Asp  Thr
               100                     105                     110

Ser  Asn  Ala  His  Leu  Trp  Phe  Glu  Asn  Ala  Asp  Gly  Thr  Glu  Arg  Gly
          115                     120                     125

Val  Ile  Tyr  Ala  Arg  Pro  Gln  Thr  Thr  Thr  Asp  Gly  Glu  Ile  Arg  Leu
     130                     135                     140

Arg  Val  Arg  Gln  Gly  Thr  Gly  Ser  Thr  Ala  Asn  Ser  Glu  Phe  Tyr  Phe
145                      150                     155                      160

Arg  Ser  Ile  Asn  Gly  Gly  Glu  Phe  Gln  Ala  Asn  Arg  Ile  Leu  Ala  Ser
               165                     170                     175

Asp  Ser  Leu  Val  Thr  Lys  Arg  Ile  Ala  Val  Asp  Thr  Val  Ile  His  Asp
          180                     185                     190

Ala  Lys  Ala  Phe  Gly  Gln  Tyr  Asp  Ser  His  Ser  Leu  Val  Asn  Tyr  Val
          195                     200                     205

Tyr  Pro  Gly  Thr  Gly  Glu  Thr  Asn  Gly  Val  Asn  Tyr  Leu  Arg  Lys  Val
     210                     215                     220

Arg  Ala  Lys  Ser  Gly  Gly  Thr  Ile  Tyr  His  Glu  Ile  Val  Thr  Ala  Gln
225                      230                     235                      240

Thr  Gly  Leu  Ala  Asp  Glu  Val  Ser  Trp  Trp  Ser  Gly  Asp  Thr  Pro  Val
               245                     250                     255

Phe  Lys  Leu  Tyr  Gly  Ile  Arg  Asp  Asp  Gly  Arg  Met  Ile  Ile  Arg  Asn
               260                     265                     270

Ser  Leu  Ala  Leu  Gly  Thr  Phe  Thr  Thr  Asn  Phe  Pro  Ser  Ser  Asp  Tyr
          275                     280                     285
```

-continued

```
Gly  Asn  Val  Gly  Val  Met  Gly  Asp  Lys  Tyr  Leu  Val  Leu  Gly  Asp  Thr
     290                 295                      300
Val  Thr  Gly  Leu  Ser  Tyr  Lys  Lys  Thr  Gly  Val  Phe  Asp  Leu  Val  Gly
305                      310                      315                      320
Gly  Gly  Tyr  Ser  Val  Ala  Ser  Ile  Thr  Pro  Asp  Ser  Phe  Arg  Ser  Thr
                         325                 330                      335
Arg  Lys  Gly  Ile  Phe  Gly  Arg  Ser  Glu  Asp  Gln  Gly  Ala  Thr  Trp  Ile
                    340                 345                      350
Met  Pro  Gly  Thr  Asn  Ala  Ala  Leu  Leu  Ser  Val  Gln  Thr  Gln  Ala  Asp
          355                      360                 365
Asn  Asn  Asn  Ala  Gly  Asp  Gly  Gln  Thr  His  Ile  Gly  Tyr  Asn  Ala  Gly
     370                      375                      380
Gly  Lys  Met  Asn  His  Tyr  Phe  Arg  Gly  Thr  Gly  Gln  Met  Asn  Ile  Asn
385                      390                      395                      400
Thr  Gln  Gln  Gly  Met  Glu  Ile  Asn  Pro  Gly  Ile  Leu  Lys  Leu  Val  Thr
                         405                 410                      415
Gly  Ser  Asn  Asn  Val  Gln  Phe  Tyr  Ala  Asp  Gly  Thr  Ile  Ser  Ser  Ile
                    420                 425                      430
Gln  Pro  Ile  Lys  Leu  Asp  Asn  Glu  Ile  Phe  Leu  Thr  Lys  Ser  Asn  Asn
               435                 440                      445
Thr  Ala  Gly  Leu  Lys  Phe  Gly  Ala  Pro  Ser  Gln  Val  Asp  Gly  Thr  Arg
     450                      455                      460
Thr  Ile  Gln  Trp  Asn  Gly  Gly  Thr  Arg  Glu  Gly  Gln  Asn  Lys  Asn  Tyr
465                      470                      475                      480
Val  Ile  Ile  Lys  Ala  Trp  Gly  Asn  Ser  Phe  Asn  Ala  Thr  Gly  Asp  Arg
                         485                 490                      495
Ser  Arg  Glu  Thr  Val  Phe  Gln  Val  Ser  Asp  Ser  Gln  Gly  Tyr  Tyr  Phe
               500                 505                      510
Tyr  Ala  His  Arg  Lys  Ala  Pro  Thr  Gly  Asp  Glu  Thr  Ile  Gly  Arg  Ile
          515                      520                      525
Glu  Ala  Gln  Phe  Ala  Gly  Asp  Val  Tyr  Ala  Lys  Gly  Ile  Ile  Ala  Asn
     530                      535                      540
Gly  Asn  Phe  Arg  Val  Val  Gly  Ser  Ser  Ala  Leu  Ala  Gly  Asn  Val  Thr
545                      550                      555                      560
Met  Ser  Asn  Gly  Leu  Phe  Val  Gln  Gly  Gly  Ser  Ser  Ile  Thr  Gly  Gln
                    565                 570                      575
Val  Lys  Ile  Gly  Gly  Thr  Ala  Asn  Ala  Leu  Arg  Ile  Trp  Asn  Ala  Glu
               580                 585                      590
Tyr  Gly  Ala  Ile  Phe  Arg  Arg  Ser  Glu  Ser  Asn  Phe  Tyr  Ile  Ile  Pro
          595                      600                      605
Thr  Asn  Gln  Asn  Glu  Gly  Glu  Ser  Gly  Asp  Ile  His  Ser  Ser  Leu  Arg
     610                      615                      620
Pro  Val  Arg  Ile  Gly  Leu  Asn  Asp  Gly  Met  Val  Gly  Leu  Gly  Arg  Asp
625                      630                      635                      640
Ser  Phe  Ile  Val  Asp  Gln  Asn  Asn  Ala  Leu  Thr  Thr  Ile  Asn  Ser  Asn
                         645                 650                      655
Ser  Arg  Ile  Asn  Ala  Asn  Phe  Arg  Met  Gln  Leu  Gly  Gln  Ser  Ala  Tyr
               660                 665                      670
Ile  Asp  Ala  Glu  Cys  Thr  Asp  Ala  Val  Arg  Pro  Ala  Gly  Ala  Gly  Ser
          675                      680                      685
Phe  Ala  Ser  Gln  Asn  Asn  Glu  Asp  Val  Arg  Ala  Pro  Phe  Tyr  Met  Asn
     690                      695                      700
Ile  Asp  Arg  Thr  Asp  Ala  Ser  Ala  Tyr  Val  Pro  Ile  Leu  Lys  Gln  Arg
```

| | 705 | | | | 710 | | | | 715 | | | | 720 | |
|---|---|---|---|---|---|---|---|---|---|---|---|---|---|---|
| Tyr | Val | Gln | Gly | Asn 725 | Gly | Cys | Tyr | Ser | Leu 730 | Gly | Thr | Leu | Ile | Asn 735 | Asn |
| Gly | Asn | Phe | Arg 740 | Val | His | Tyr | His | Gly 745 | Gly | Gly | Asp | Asn | Gly 750 | Ser | Thr |
| Gly | Pro | Gln 755 | Thr | Ala | Asp | Phe | Gly 760 | Trp | Glu | Phe | Ile | Lys 765 | Asn | Gly | Asp |
| Phe | Ile 770 | Ser | Pro | Arg | Asp | Leu 775 | Ile | Ala | Gly | Lys | Val 780 | Arg | Phe | Asp | Arg |
| Thr 785 | Gly | Asn | Ile | Thr | Gly 790 | Gly | Ser | Gly | Asn | Phe 795 | Ala | Asn | Leu | Asn | Ser 800 |
| Thr | Ile | Glu | Ser | Leu 805 | Lys | Thr | Asp | Ile | Met 810 | Ser | Ser | Tyr | Pro | Ile 815 | Gly |
| Ala | Pro | Ile | Pro 820 | Trp | Pro | Ser | Asp | Ser 825 | Val | Pro | Ala | Gly | Phe 830 | Ala | Leu |
| Met | Glu | Gly 835 | Gln | Thr | Phe | Asp | Lys 840 | Ser | Ala | Tyr | Pro | Lys 845 | Leu | Ala | Val |
| Ala | Tyr 850 | Pro | Ser | Gly | Val | Ile 855 | Pro | Asp | Met | Arg | Gly 860 | Gln | Thr | Ile | Lys |
| Gly 865 | Lys | Pro | Ser | Gly | Arg 870 | Ala | Val | Leu | Ser | Ala 875 | Glu | Ala | Asp | Gly | Val 880 |
| Lys | Ala | His | Ser | His 885 | Ser | Ala | Ser | Ala | Ser 890 | Ser | Thr | Asp | Leu | Gly 895 | Thr |
| Lys | Thr | Thr | Ser 900 | Ser | Phe | Asp | Tyr | Gly 905 | Thr | Lys | Gly | Thr | Asn 910 | Ser | Thr |
| Gly | Gly | His 915 | Thr | His | Ser | Gly | Ser 920 | Gly | Ser | Thr | Ser | Thr 925 | Asn | Gly | Glu |
| His | Ser 930 | His | Tyr | Ile | Glu | Ala 935 | Trp | Asn | Gly | Thr | Gly 940 | Val | Gly | Gly | Asn |
| Lys 945 | Met | Ser | Ser | Tyr | Ala 950 | Ile | Ser | Tyr | Arg | Ala 955 | Gly | Gly | Ser | Asn | Thr 960 |
| Asn | Ala | Ala | Gly | Asn 965 | His | Ser | His | Thr | Phe 970 | Ser | Phe | Gly | Thr | Ser 975 | Ser |
| Ala | Gly | Asp | His 980 | Ser | His | Ser | Val | Gly 985 | Ile | Gly | Ala | His | Thr 990 | His | Thr |
| Val | Ala | Ile 995 | Gly | Ser | His | Gly | His 1000 | Thr | Ile | Thr | Val | Asn 1005 | Ser | Thr | Gly |
| Asn | Thr 1010 | Glu | Asn | Thr | Val | Lys 1015 | Asn | Ile | Ala | Phe | Asn 1020 | Tyr | Ile | Val | Arg |
| Leu 1025 | Ala | | | | | | | | | | | | | | |

MATERIALS FOR THE PRODUCTION OF NANOMETER STRUCTURES AND USE THEREOF

This application is a continuation-in-part of copending application Ser. No. 08/322,760 filed Oct. 13, 1994, which is incorporated by reference herein in its entirety.

This invention was made with Government support under Grant No. MCB 9308834 awarded by the National Science Foundation. The Government has certain rights in this invention.

TABLE OF CONTENTS

FIELD OF THE INVENTION
BACKGROUND OF THE INVENTION
SUMMARY OF THE INVENTION
BRIEF DESCRIPTION OF THE DRAWINGS
DETAILED DESCRIPTION OF THE INVENTION
DEFINITIONS
STRUCTURAL UNITS
DESIGN AND PRODUCTION OF THE ROD PROTEINS
ASSEMBLY OF INDIVIDUAL ROD COMPONENTS INTO NANOSTRUCTURES
APPLICATIONS
KITS
EXAMPLE 1: DESIGN, CONSTRUCTION AND EXPRESSION OF INTERNALLY DELETED P37
EXAMPLE 2: DESIGN, CONSTRUCTION AND EXPRESSION OF A gp37-36 CHIMER
EXAMPLE 3: MUTATION OF THE GP37-36 CHIMER TO PRODUCE COMPLEMENTARY SUPPRESSORS
EXAMPLE 4: DESIGN, CONSTRUCTION AND EXPRESSION OF A gp36-34 CHIMER
EXAMPLE 5: ISOLATION OF THERMOLABILE PROTEINS FOR SELF-ASSEMBLY
EXAMPLE 6: ASSEMBLY OF ONE-DIMENSIONAL RODS
EXAMPLE 7: STAGED ASSEMBLY OF POLYGONS

FIELD OF THE INVENTION

The present invention pertains to nanostructures, i.e., nanometer sized structures useful in the construction of microscopic and macroscopic structures. In particular, the present invention pertains to nanostructures based on bacteriophage T4 tail fiber proteins and variants thereof.

BACKGROUND TO THE INVENTION

While the strength of most metallic and ceramic based materials derives from the theoretical bonding strengths between their component molecules and crystallite surfaces, it is significantly limited by flaws in their crystal or glass-like structures. These flaws are usually inherent in the raw materials themselves or developed during fabrication and are often expanded due to exposure to environmental stresses.

The emerging field of nanotechnology has made the limitations of traditional materials more critical. The ability to design and produce very small structures (i.e., of nanometer dimensions) that can serve complex functions depends upon the use of appropriate materials that can be manipulated in predictable and reproducible ways, and that have the properties required for each novel application.

Biological systems serve as a paradigm for sophisticated nanostructures. Living cells fabricate proteins and combine them into structures that are perfectly formed and can resist damage in their normal environment. In some cases, intricate structures are created by a process of self-assembly, the instructions for which are built into the component polypeptides. Finally, proteins are subject to proofreading processes that insure a high degree of quality control.

Therefore, there is a need in the art for methods and compositions that exploit these unique features of proteins to form constituents of synthetic nanostructures. The need is to design materials whose properties can be tailored to suit the particular requirements of nanometer-scale technology. Moreover, since the subunits of most macrostructural materials, ceramics, metals, fibers, etc., are based on the bonding of nanostructural subunits, the fabrication of appropriate subunits without flaws and of exact dimensions and uniformity should improve the strength and consistency of the macrostructures because the surfaces are more regular and can interact more closely over an extended area than larger, more heterogeneous material.

SUMMARY OF THE INVENTION

In one aspect, the present invention provides isolated protein building blocks for nanostructures, comprising modified tail fiber proteins of bacteriophage T4. The gp34, 36, and 37 proteins are modified in various ways to form novel rod structures with different properties. Specific internal peptide sequences may be deleted without affecting their ability to form dimers and associate with their natural tail fiber partners. Alternatively, they may be modified so that they: interact only with other modified, and not native, tail fiber partners; exhibit thermolabile interactions with their partners; or contain additional functional groups that enable them to interact with heterologous binding moieties.

The present invention also encompasses fusion proteins that contain sequences from two or more different tail fiber proteins. The gp35 protein, which forms an angle joint, is modified so as to form average angles different from the natural average angle of 137° (±7°) or 156° (±12°), and to exhibit thermolabile interactions with its partners.

In another aspect, the present invention provides nanostructures comprising native and modified tail fiber proteins of bacteriophage T4. The nanostructures may be one-dimensional rods, two-dimensional polygons or open or closed sheets, or three-dimensional open cages or closed solids.

BRIEF DESCRIPTION OF THE DRAWINGS

FIG. 2 shows a schematic representation of a unit rod.

FIGS. 3A–3D show schematic representations of: a one-dimensional multi-unit rod joined along the x axis (FIG. 3A); closed simple sheets (FIG. 3B); closed brickwork sheets (FIG. 3C); and open brickwork sheets (FIG. 3D).

FIG. 4 shows a schematic representation of two units used to construct porous and solid sheets (top and bottom), which, when alternatively layered, produce a multi-tiered set of cages as shown.

FIG. 5 shows a schematic representation of an angled structure having an angle of 120°.

FIG. 6 shows the DNA sequence (SEQ ID NO:1) of genes 34, 35, 36, and 37 of bacteriophage T4.

FIG. 7 shows the amino acid sequences (shown in single-letter codes) of the gene products of genes 34 (SEQ ID NO:2, ORFX SEQ ID NO:3), 35 (SEQ ID NO:4), 36 (SEQ ID NO:5), and 37 (SEQ ID NO:6) of bacteriophage T4. The amino acid sequences (bottom line of each pair) are aligned with the nucleotide sequences (top line of each pair.) It is noted that the deduced protein sequence of gene 35 (from NCBI database) is not believed to be accurate.

FIGS. 8A–8B show a schematic representation of: the formation of a P37 dimer initiator from a molecule that self-assembles into a dimer (FIG. 8A); and the formation of a P37 trimer initiator from a molecule that self-assembles into a trimer (FIG. 8B).

FIG. 9 shows a schematic representation of the formation of the polymer (P37-36)n with an initiator that is a self-assembling dimer.

DETAILED DESCRIPTION OF THE INVENTION

Figure 1A:
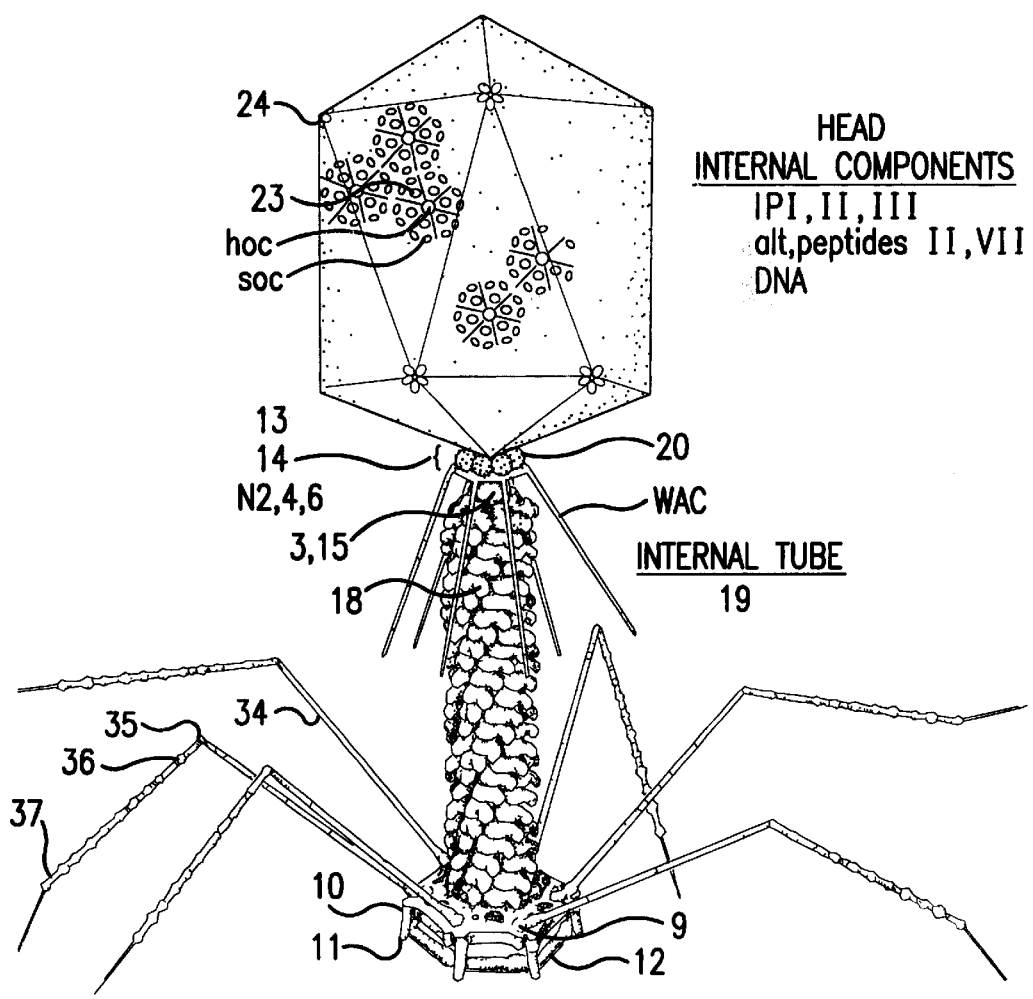
FIGS. 1A and 1B show a schematic representation of the T4 bacteriophage particle (FIG. 1A), and a schematic representation of the T4 bacteriophage tail fiber (FIG. 1B).

All patents, patent applications and literature references cited in the specification are hereby incorporated by reference in their entirety. In the case of inconsistencies, the present disclosure, including, definitions, will prevail.

Although the invention is described in terms of bacteriophage T4 tail fiber proteins, it will be understood that the invention is also applicable to tail fiber proteins of other T-even-like phage, e.g., of the T4 family (e.g., T4, TuIa, TuIb), and T2 family (T2, T6, K3, Ox2, M1, etc.)

DEFINITIONS

"Nanostructures" are defined herein as structures of different sizes and shapes that are assembled from nanometer-sized protein components.

"Chimers" are defined herein as chimeric proteins in which at least the amino- and carboxy-terminal regions are derived from different original polypeptides, whether the original polypeptides are naturally occurring or have been modified by mutagenesis.

"Homodimers" are defined herein as assemblies of two substantially identical protein subunits that form a defined three-dimensional structure.

The designation "gp" denotes a monomeric polypeptide, while the designation "P" denotes homooligomers. P34, P36, and P37 are presumably homodimers or homotrimers.

An isolated polypeptide that "consists essentially of" a specified amino acid sequence is defined herein as a polypeptide having the specified sequence or a polypeptide that contains conservative substitutions within that sequence. Conservative substitutions, as those of ordinary skill in the art would understand, are ones in which an acidic residue is replaced by an acidic residue, a basic residue by a basic residue, or a hydrophobic residue by a hydrophobic residue. Also encompassed is a polypeptide that lacks one or more amino acids at either the amino terminus or carboxy terminus, up to a total of five at either terminus, when the absence of the particular residues has no discernable effect on the structure or the function of the polypeptide in practicing the present invention.

The present invention pertains to a new class of protein building blocks whose dimensions are measured in nanometers, which are useful in the construction of microscopic and macroscopic structures. Without wishing to be bound by theory, it is believed that the basic unit is a homodimer composed of two identical protein subunits having a cross-β configuration, although a trimeric structure is also possible. Thus, as will be apparent, references to a "homodimer" or "dimerization" as used herein will in many instances be construed as also referring to a homotrimer or trimerization. These long, stiff, and stable rod-shaped units can assemble with other rods using coupling devices that can be attached genetically or in vitro. The ends of one rod may attach to different ends of other rods or similar rods. Variations in the length of the rods, in the angles of attachment, and in their flexibility characteristics permit differently-shaped structures to self-assemble in situ. In this manner the units can self-assemble into predetermined larger structures of one, two or three dimensions. The self-assembly can be staged to form structures of precise dimensions and uniform strength due to the flawless biological manufacture of the components. The rods can also be modified by genetic and chemical modifications to form predetermined specific attachment sites for other chemical entities, allowing the formation of complex structures.

An important aspect of the present invention is that the protein units can be designed so that they comprise rods of different lengths, and can be further modified to include features that alter their surface properties in predetermined ways and/or influence their ability to join with other identical or different units. Furthermore, the self-assembly capabilities can be expanded by producing chimeric proteins that combine the properties of two different members of this class. This design feature is achieved by manipulating the structure of the genes encoding these proteins.

As detailed below, the compositions and methods of the present invention take advantage of the properties of the natural proteins, i.e., the resulting structures are stiff, strong, stable in aqueous media, heat resistant, protease resistant, and can be rendered biodegradable. A large quantity of units can be fabricated easily in microorganisms. Furthermore, for ease of automation, large quantities of parts and subassemblies can be stored and used as needed.

The sequences of the protein subunits are based on the components of the tail fiber of the T4 bacteriophage of *E. coli*. It will be understood that the principles and techniques can be applied to the tail fibers of other T-even phages, or other related bacteriophages that have similar tail and/or fiber structures.

Figure 1B:
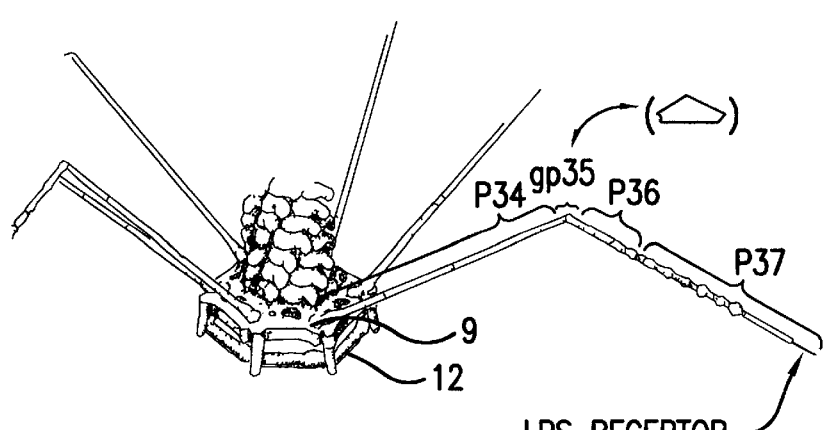

The structure of the T4 bacteriophage tail fiber (illustrated in FIG. 1) can be represented schematically as follows (N=amino terminus, C=carboxy terminus): N[P34]C-N [gp35]C-N[P36]C-N[P37]C. P34, P36, and P37 are all stiff, rod-shaped protein homodimers in which two identical β sheets, oriented in the same direction, are fused face-to-face by hydrophobic interactions between the sheets juxtaposed with a 180° rotational axis of symmetry through the long axis of the rod. (The structure will vary if P34, P36, and P37 are homotrimers.) Gp35, by contrast, is a monomeric polypeptide that attaches specifically to the N-terminus of P36 and then to the C-terminus of P34 and forms an angle joint between two rods. During T4 infection of *E. coli*, two gp37 monomers dimerize to form a P37 homodimer; the process of dimerization is believed to initiate near the C-terminus of P37 and to require two *E. coli* chaperon proteins. (A variant gp37 with a temperature sensitive mutation near the C-terminus used in the present invention requires only one chaperon, gp57, for dimerization.) Once dimerized, the N-terminus of P37 initiates the dimerization of two gp36 monomers to a P36 rod. The joint between the C-terminus of P36 and the N-terminus of P37 is tight and stiff but noncovalent. The N-terminus of P36 then attaches to a gp35 monomer; this interaction stabilizes P36 and forms the elbow of the tail fiber. Finally, gp35 attaches to the C-terminus of P34 (which uses gp57 for dimerization). Thus, self assembly of the tail fiber is regulated by a predetermined order of interaction of specific subunits whereby structural maturation caused by formation of the first subassembly permits interaction with new (previously disallowed) subunits. This results in the production of a structure of exact specifications from a random mixture of the components.

In accordance with the present invention, the genes encoding these proteins may be modified so as to make rods of different lengths with different combinations of ends. The properties of the native proteins are particularly advantageous in this regard. First, the β-sheet is composed of antiparallel β-strands with β-bends at the left (L) and right (R) edges. Second, the amino acid side chains alternate up and down out of the plane of the sheet. The first property allows bends to be extended to form symmetric and specific attachment sites between the L and R surfaces, as well as to form attachment sites for other structures. In addition, the core sections of the β-sheet can be shortened or lengthened by genetic manipulations e.g., by splicing DNA regions encoding β-bends, on the same edge of the sheet, to form new bends that exclude intervening peptides, or by inserting segments of peptide in an analogous manner by splicing at bend angles. The second property allows amino acid side chains extending above and below the surface of the β-sheet to be modified by genetic substitution or chemical coupling. Importantly, all of the above modifications are achieved without compromising the structural integrity of the rod. It will be understood by one skilled in the art that these properties allow a great deal of flexibility in designing units that can assemble into a broad variety of structures, some of which are detailed below.

STRUCTURAL UNITS

The rods of the present invention function like wooden 2×4 studs or steel beams for construction. In this case, the surfaces are exactly reproducible at the molecular level and thereby fitted for specific attachments to similar or different units rods at fixed joining sites. The surfaces are also modified to be more or less hydrophilic, including positively or negatively charged groups, and have protrusions built in for specific binding to other units or to an intermediate joint with two receptor sites. The surfaces of the rod and a schematic of the unit rod are illustrated in FIG. 2. The three dimensions of the rod are defined as: x, for the back (B) to front (F) dimension; y, for the down (D) to up (U) dimension; and z, for the left (L) to right (R) dimension.

One dimensional multi-unit rods can be most readily assembled from single unit rods joined along the x axis (FIG. 3A) but regular joining of subunits in either of the other two dimensions will also form a long structure, but with different cross sections than in the x dimension.

Figure 3C:
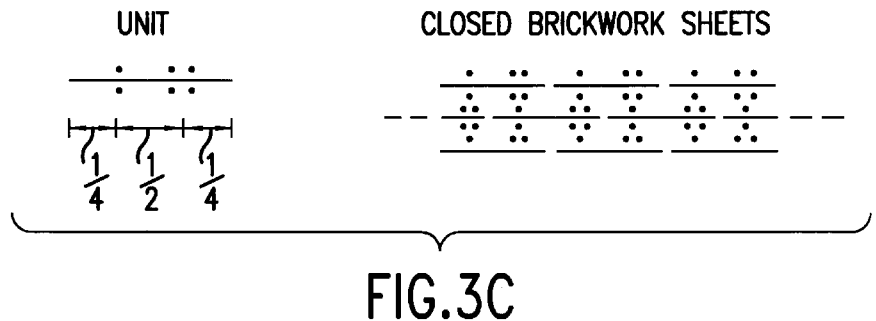
Figure 3D:
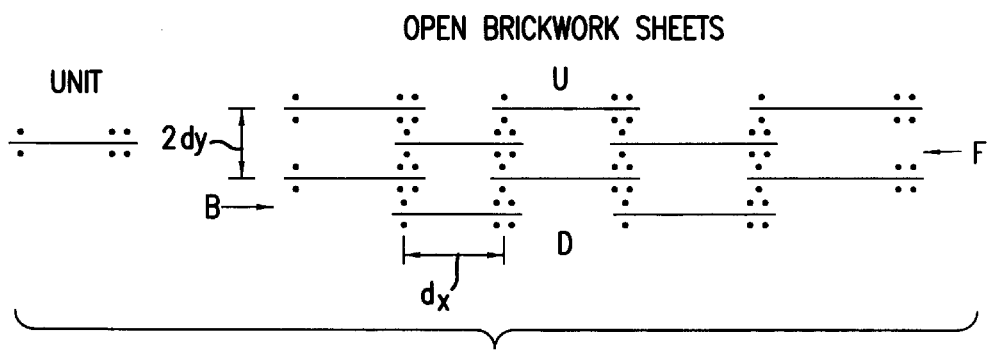

Two dimensional constructs are sheets formed by interaction of rods along any two axes. 1) Closed simple sheets are formed from surfaces which overlap exactly, along any two axes (FIG. 3B). 2) Closed brickwork sheets are formed from interaction between units that have exactly overlapping surfaces in one dimension and a special type of overlap in the other (FIG. 3C). In this case there must be two different sets of complementary joints spaced with exactly ½ unit distance between them. If they are centered (i.e., each set ¼ from the end) then each joint will be in the center of the units above and below. If they are offset, then the joint will be offset as well. In this construction, the complementary interacting sites are schematized by • and ••. If the interacting sites are each symmetric, the alternating rows can interact with the rods in either direction. If they are not symmetric, and can only interact with interacting rows facing in the same or opposite direction, the sheet will made of unidirectional rods or layers of rods in alternating directions. 3) Open brickwork sheets (or nets) result when the units are separated by more than one-half unit (FIG. 3D). The dimensions of the openings (or pores) depend upon the distance (dx) separating the interacting sites and the distance (dy) by which these sites separate the surfaces.

Three dimensional constructs require sterically compatible interactions between all three surfaces to form solids. 1) Closed solids can assemble from units that overlap exactly in all three dimensions (e.g., the exact overlapping of closed simple sheets). In an analogous manner, closed brickwork sheets can form closed solids by overlapping sheets exactly or displaced to bring the brickwork into the third dimension. This requires an appropriate set of joints on all three pairs of parallel faces of the unit. 2) Porous solids are made by joining open brickwork sheets in various ways. For example, if the units overlap exactly in the third dimension, a solid is formed with the array of holes of exact dimensions running perpendicular to the plane of the paper. If instead, a material is needed with closed spaces, with layers of width dz (i.e., in the U→>D dimension), a simple closed sheet is layered on the open brickwork sheet to close the openings. If the overlap of the open brickwork sheet is e.g., ¼ unit, then a rod of length ¾ units is used to make the sheet. Joints are then needed in the z dimension. The two units used to polymerize these alternate layers, and the layers themselves, are schematized in FIG. 4.

All of the above structures are composed of simple linear rods. A second unit, the angle unit, expands the type and dimensionality of possible structures. The angle unit connects two rods at angles different from 180°, akin to an angle iron. The average angle and its degree of rigidity are built into this connector structure. For example, the structure shown in FIG. 5 has an angle of 120° and different specific joining sites at a and at b. The following are examples of structures that are formed utilizing angle joints:

1) Open brickwork sheets are expanded and strengthened in the direction normal to the rod direction by adding angles perpendicular to the sheet. In this case, a three dimensional network forms. Attachment of 90° angles to the ends of the rods makes an angle almost in the plane of the sheet, allowing new rods added to those angles (which must have some play out of the plane of the original sheet to attach in the first place) to form a new sheet, almost parallel, with an orientation normal to its upper or lower neighbor.

2) Hexagons are made from a mixture of rods and angle joints that form 120° angles. In this case, there are two exclusive sets of joints. Each set is made up of one of the two ends of the rod and one of the two complementary sites on the angle. This is a linear structure in the sense that the hexagon has a direction (either clockwise or counterclockwise). It can be made into a two dimensional open net (i.e., a two dimensional honeycomb) by joining the sides of the hexagons. It can form hexagonal tubes by joining the top of the hexagon below to the bottom face of the hexagon above. If the tubes also join by their sides, they will form an open three dimensional multiple hexagonal tube.

3) Helical hexagonal tubes are made analogously to hexagons but the sixth unit is not joined to the first to close the hexagon. Instead, the end is displaced from the plane of the hexagon and the seventh and further units are added to form a hexagonal tube which can be a spring if there is little or no adhesive force between the units of the helix, or a stiff rod if there is such a force to maintain the close proximity of apposing units.

It will be apparent to one skilled in the art that the compositions and methods of the present invention also encompass other polygonal structures such as octagons, as well as open solids such as tetrahedrons and icosahedrons formed from triangles and boxes formed from squares and rectangles. The range of structures is limited only by the types of angle units and the substituents that can be engineered on the different axes of the rod units. For example, other naturally occurring angles are found in the fibers of bacteriophage T7, which has a 90° angle (Steven et al., *J. Mol. Biol.* 200: 352–365, 1988).

DESIGN AND PRODUCTION OF THE ROD PROTEINS

The protein subunits that are used to construct the nanostructures of the present invention are based on the four polypeptides that comprise the tail fibers of bacteriophage T4, i.e., gp34, gp35, gp36 and gp37. The genes encoding these proteins have been cloned, and their DNA and protein sequences have been determined (for gene 36 and 37 see Oliver et al. *J. Mol. Biol.* 153: 545–568, 1981). The DNA and amino acid sequences of genes 34, 35, 36 and 37 are set forth in FIGS. 6 and 7 below.

Gp34, gp35, gp36, and gp37 are produced naturally following infection of *E. coli* cells by intact T4 phage particles. Following synthesis in the cytoplasm of the bacterial cell, the gp34, 36, and 37 monomers form homodimers, which are competent for assembly into maturing phage particles. Thus, *E. coil* serves as an efficient and convenient factory for synthesis and dimerization of the protein subunits described herein below.

In practicing the present invention, the genes encoding the proteins of interest (native, modified, or recombined) are incorporated into DNA expression vectors that are well known in the art. These circular plasmids typically contain selectable marker genes (usually conferring antibiotic resistance to transformed bacteria), sequences that allow replication of the plasmid to high copy number in *E. coli*, and a multiple cloning site immediately downstream of an inducible promoter and ribosome binding site. Examples of commercially available vectors suitable for use in the present invention include the pET system (Novagen, Inc., Madison, Wis.) and Superlinker vectors pSE280 and pSE380 (Invitrogen, San Diego, Calif.).

The strategy is to 1) construct the gene of interest and clone it into the multiple cloning site; 2) transform *E. coli* cells with the recombinant plasmid; 3) induce the expression of the cloned gene; 4) test for synthesis of the protein product; and, finally, 5) test for the formation of functional homodimers. In some cases, additional genes are also cloned into the same plasmid, when their function is required for dimerization of the protein of interest. For example, when wild-type or modified versions of gp37 are expressed, the bacterial chaperon gene 57 is also included; when wild-type or modified gp36 is expressed, the wild-type version or a modified version of the gp37 gene is included. The modified gp37 should have the capacity to dimerize and contain an N-terminus that can chaperon the dimerization of gp36. This method allows the formation of monomeric gene products and, in some cases, maturation of monomers to homodimeric rods in the absence of other phage-induced proteins normally present in a T4-infected cell.

Steps 1–4 of the above-defined strategy are achieved by methods that are well known in the art of recombinant DNA technology and protein expression in bacteria. For example, in step 1, restriction enzyme cleavage at multiple sites, followed by ligation of fragments, is used to construct deletions in the internal rod segment of gp34, 36, and 35 (see Example 1 below). Alternatively, a single or multiple restriction enzyme cleavage, followed by exonuclease digestion (EXO-SIZE, New England Biolabs, Beverly, Mass.), is used to delete DNA sequences in one or both directions from the initial cleavage site; when combined with a subsequent ligation step, this procedure produces a nested set of deletions of increasing sizes. Similarly, standard methods are used to recombine DNA segments from two different tail fiber genes, to produce chimeric genes encoding fusion proteins (called "chimers" in this description). In general, this last method is used to provide alternate N- or C-termini and thus create novel combinations of ends that enable new patterns of joining of different rod segments. A representative of this type of chimer, the fusion of gp37-36, is described in Example 2. The preferred hosts for production of these proteins (Step 2) is *E. coli* strain BL21(DE3) and BL21(DE3/pLysS) (available commercially from Novagen, Madison, Wis.), although other compatible recA strains, such as HMS174(DE3) and HMS174(DE3/pLysS) can be used. Transformation with the recombinant plasmid (Step 2) is accomplished by standard methods (Sambrook, J., *Molecular Cloning*, Cold Spring Harbor Laboratories, Cold Spring Harbor, N.Y.; this is also the source for standard recombinant DNA methods used in this invention.) Transformed bacteria are selected by virtue of their resistance to antibiotics e.g., ampicillin or kanamycin. The method by which expression of the cloned tail fiber genes is induced (Step 3) depends upon the particular promoter used. A preferred promoter is plac (with a laci$^q$ on the vector to reduce background expression), which can be regulated by the addition of isopropylthiogalactoside (IPTG). A second preferred promoter is pT7ϕ10, which is specific to T7 RNA polymerase and is not recognized by *E. coli* RNA polymerase. T7 RNA polymerase, which is resistant to rifamycin, is encoded on the defective lambda DE lysogen in the *E. coli* BL21 chromosome. T7 polymerase in BL21 (DE3) is super-repressed by the laci$^q$ gene in the plasmid and is induced and regulated by IPTG.

Typically, a culture of transformed bacteria is incubated with the inducer for a period of hours, during which the synthesis of the protein of interest is monitored. In the present instance, extracts of the bacterial cells are prepared, and the T4 tail fiber proteins are detected, for example, by SDS-polyacrylamide gel electrophoresis.

Once the modified protein is detected in bacterial extracts, it is necessary to ascertain whether or not it forms appropriate homodimers (Step 4). This is accomplished initially by testing whether the protein is recognized by an antiserum specific to the mature dimerized form of the protein.

Tail fiber-specific antisera are prepared as described (Edgar, R. S. and Lielausis, I., *Genetics* 52: 1187, 1965; Ward et al, *J. Mol. Biol.* 54:15, 1970). Briefly, whole T4 phage are used as an immunogen; optionally, the resulting antiserum is then adsorbed with tail-less phage particles, thus removing all antibodies except those directed against the tail fiber proteins. In a subsequent step, different aliquots of the antiserum are adsorbed individually with extracts that each lack a particular tail fiber protein. For example, if an extract containing only tail fiber components P34, gp35, and gp36 (derived from a cell infected with a mutant T4 lacking a functional gp37 gene) is used for absorption, the resulting antiserum will recognize only mature P37 and dimerized P36-P37. A similar approach may be used to prepare individual antisera that recognize only mature (i.e., homodimerized) P34 and P36 by adsorbing with extracts containing distal half tail fibers or P34, gp35 and P37, respectively. An alternative is to raise antibody against purified tail fiber halves, e.g., P34 and gp35-P36-P37. Anti gp35-P36-P37 can then be adsorbed with P36-P37 to produce anti-gp35, and anti-P36 can be produced by adsorption with P37 and gp35. Anti-P37, anti-gp35, and anti-P34 P4 can also be produced directly by using purified P37, gp35, and P34 as immunogens. Another approach is to raise specific monoclonal antibodies against the different tail fiber components or segments thereof.

Specific antibodies to subunits or tail parts are used in any of the following ways to detect appropriately homodimerized tail fiber proteins: 1) Bacterial colonies are screened for those expressing mature tail fiber proteins by directly transferring the colonies, or, alternatively, samples of lysed or unlysed cultures, to nitrocellulose filters, lysing the bacterial cells on the filter if necessary, and incubating with specific antibodies. Formation of immune complexes is then detected by methods widely used in the art (e.g., secondary antibody conjugated to a chromogenic enzyme or radiolabelled Staphylococcal Protein A.). This method is particularly useful to screen large numbers of colonies e.g., those produced by EXO-SIZE deletion as described above. 2) Bacterial cells expressing the protein of interest are first metabolically labelled with $^{35}$S-methionine, followed by preparation of extracts and incubation with the antiserum. The immune complexes are then recovered by incubation with immobilized Protein A followed by centrifugation, after which they may be resolved by SDS-polyacrylamide gel electrophoresis.

An alternative competitive assay for testing whether internally deleted tail fiber proteins that do not permit phage infection nonetheless retain the ability to dimerize and associate with their appropriate partners utilizes an in vitro, complementation system. 1) A bacterial extract containing the modified protein of interest, as described above, is mixed with a second extract prepared from cells infected with a T4 phage that is mutant in the gene of interest. 2) After several hours of incubation, a third extract is added that contains the wild-type version of the protein being tested, and incubation is continued for several additional hours. 3) Finally, the extract is titered for infectious phage particles by infecting E. coli and quantifying the phage plaques that result. A modified tail fiber protein that is correctly dimerized and able to join with its partners is incorporated into tail fibers in a non-functional manner in Step 1, thereby preventing the incorporation of the wild-type version of the protein in Step 2; the result is a reduction in the titer of the resulting phage sample. By contrast, if the modified protein is unable to dimerize and thus form proper N- and/or C-termini, it will not be incorporated into phage particles in Step 1, and thus will not compete with assembly of intact phage particles in Step 2; the phage titer should thus be equivalent to that observed when no modified protein is added in Step 1 (a negative control.)

Another way in which to test whether chimers and internally deleted tail fiber proteins retain the ability to dimerize and associate with their appropriate partners is done in vivo. The assay detects the ability of such chimers and deleted proteins to compete with normal phage parts for assembly, thus reducing the burst size of a wild-type phage infecting the same host cell in which the chimers or deleted proteins are recombinantly expressed. Thus, expression from an expression vector encoding the chimer or deleted protein is induced inside a cell, which cell is then infected by a wild-type phage. Inhibition of wild-type phage production demonstrates the ability of the recombinant chimer or protein to associate with the appropriate tail fiber proteins of the phage.

The above-described methods are used, alone and in combination, in the design and production of different types of modified tail fiber proteins. For example, a preliminary screen of a large number of bacterial colonies for those expressing a properly dimerized protein will identify positive colonies, which can then be individually tested by in vitro complementation.

Non-limiting examples of novel proteins that are encompassed by the present invention include:

1) Internally deleted gp34, 36, and 37 polypeptides (See Example 1 below);
2) A C-terminally truncated gp36 fused to the N-terminus of N-terminally truncated gp37;
3) A fusion between gp36 and gp37 in which gp37 is N-terminal to gp36 (i.e., in reverse of the natural order), termed herein "gp37-36 chimer" (See Example 2 below);
4) A fusion between gp34 and gp36 in which gp36 is N-terminal to gp34 (i.e., in reverse of the natural order), termed herein "gp36-34 chimer";
5) A variant of gp36 in which the C-terminus is mutated such that it lacks the capability to interact with (and dimerize in response to) the N-terminus of wild-type P37, termed herein "gp36*";
6) A variant of gp37 in which the N-terminus is mutated such that it forms a P37 that lacks the capability to interact with the C-terminus of wild-type gp36, termed herein "*P37";
7) Variants of gp36* and *P37 that can interact with each other, but not with gp36 or P37.
8) A variant "P37-36 chimer" in which the gp36 moiety is derived from the variant as in 5), i.e., "P37-36*". (For 5–8, See Example 3 below.)
9) A variant "P37-36 chimer" in which the gp37 moiety is derived from the variant as in 6) above, i.e., "*P37-36".
10) A variant P37-36 chimer, *P37-P36*, in which the gp36 and gp37 moieties are derived from the variants in 7).
11) A fusion between gp36 and gp34 in which gp36 sequences are placed N-terminal to gp34, the dimer of which is termed herein "P36-34 chimer";
12) Variants of gp35 that form average angles different from 137° or 158° (the native angle) e.g., less than about 125° or more than about 145° under conditions wherein the wild-type gp35 protein forms an angle of 137° when combined with the P34 and P36-P37 dimers, and/or exhibit more or less flexibility than the native polypeptide;
13) Variants of gp34, 35, 36 and 37 that exhibit thermolabile interactions or other variant specific interactions with their cognate partners; and
14) Variants of gp37 in which the C-terminal domain of the polypeptide is modified to include sequences that confer specific binding properties on the entire molecule, e.g., sequences derived from avidin that recognize biotin, sequences derived from immunoglobulin heavy chain that recognize Staphylococcal A protein, sequences derived from the Fab portion of the heavy chain of monoclonal antibodies to which their respective Fab light chain counterparts could attach and form an antigen-binding site, immunoactive sequences that recognize specific antibodies, or sequences that bind specific metal ions. These ligands may be immobilized to facilitate purification and/or assembly.

In specific embodiments, the chimers of the invention comprise a portion consisting of at least the first 10 (N-terminal) amino acids of a first tail fiber protein fused via a peptide bond to a portion consisting of at least the last 10 (C-terminal) amino acids of a second tail fiber protein. The first and second tail fiber proteins can be the same or different proteins. In another embodiment, the chimers comprise an amino acid portion in the range of the first 10–60 amino acids from a tail fiber protein fused to an amino acid portion in the range of the last 10–60 amino acids from a second tail fiber protein. In another embodiment, each amino acid portion is at least 20 amino acids of the tail fiber protein. The chimers comprise portions, i.e., not full-length tail fiber proteins, fused to one another. In a preferred aspect, the first tail fiber protein portion of the chimer is from gp37, and the second tail fiber protein portion is from gp36. Such a chimer (gp37-36 chimer), after oligomerization to form P37-36, can polymerize to other identical oligomers. A gp36-34 chimer, after oligomerization to form P36-34, can bind to gp35, and this unit can then polymerize. In another embodiment, the first portion is from gp37, and the second portion is from gp34. In a preferred aspect, the chimers of the invention are made by insertions or deletions within a β turn of the β structure of the tail fiber proteins. Most preferably, insertions into a tail fiber sequence, or fusing to another tail fiber protein sequence, (preferably via manipulation at the recombinant DNA level to produce the desired encoded protein) is done so that sequences in β turns on the same edge of the β-sheet are joined.

In addition to the above-described chimers, nanostructures of the invention can also comprise tail fiber protein deletion constructs that are truncated at one end, e.g., are lacking an amino- or carboxy- end (of at least 5 or 10 amino acids) of the molecule. Such molecules truncated at the amino-terminus, e.g., of truncated gp37, gp34, or gp36, can be used to "cap" a nanostructure, since, once incorporated, they will terminate polymerization. Such molecules preferably comprise a fragment of a tail fiber protein lacking at least the first 10, 20, or 60 amino terminal amino acids.

In order to change the length of the rod component proteins as desired, portions of the same or different tail fiber proteins can be inserted into a tail fiber chimer to lengthen the rod, or be deleted from a chimer, to shorten the rod.

ASSEMBLY OF INDIVIDUAL ROD COMPONENTS INTO NANOSTRUCTURES

Expression of the proteins of the present invention in *E. coli* as described above results in the synthesis of large quantities of protein, and allows the simultaneous expression and assembly of different components in the same cells. The methods for scale-up of recombinant protein production are straightforward and widely known in the art, and many standard protocols can be used to recover native and modified tail fiber proteins from a bacterial culture.

In a preferred embodiment, native (nonrecombinant) gp35 is isolated for use by growing up a bacteriophage T4 having an amber mutation in gene 36, in a su° bacterial strain (not an amber suppressor), and isolating gp35 from the resulting culture by standard methods.

P34, P36-P37, P37, and chimers derived from them are purified from *E. coli* cultures as mature dimers. Gp35 and variants thereof are purified as monomers. Purification is achieved by the following procedures or combinations thereof, using standard methods: 1) chromatography on molecular sieve, ion-exchange, and/or hydrophobic matrices; 2) preparative ultracentrifugation; and 3) affinity chromatography, using as the immobilized ligand specific antibodies or other specific binding moieties. For example, the C-terminal domain of P37 binds to the lipopolysaccharide of *E. coli* B. Other T4-like phages have P37 analogues that bind other cell surface components such as OmpF or TSX protein. Alternatively, if the proteins have been engineered to include heterologous domains that act as ligands or binding sites, the cognate partner is immobilized on a solid matrix and used in affinity purification. For example, such a heterologous domain can be biotin, which binds to a streptavidin-coated solid phase.

Alternatively, several components are co-expressed in the same bacterial cells, and sub-assemblies of larger nanostructures are purified subsequent to limited in vivo assembly, using the methods enumerated above.

The purified components are then combined in vitro under conditions where assembly of the desired nanostructure occurs at temperatures between about 4° C. and about 37° C., and at pHs between about 5 and about 9. For a given nanostructure, optimal conditions for assembly (i.e., type and concentration of salts and metal ions) are easily determined by routine experimentation, such as by changing each variable individually and monitoring formation of the appropriate products.

Alternatively, one or more crude bacterial extracts may be prepared, mixed, and assembly reactions allowed to proceed prior to purification.

In some cases, one or more purified components assemble spontaneously into the desired structure, without the necessity for initiators. In other cases, an initiator is required to nucleate the polymerization of rods or sheets. This offers the advantage of localizing the assembly process (i.e., if the initiator is immobilized or otherwise localized) and of regulating the dimensions of the final structure. For example, rod components that contain a functional P36 C-terminus require a functional P37 N-terminus to initiate rod formation stoichiometrically; thus, altering the relative amount of initiator and rod component will influence the average length of rod polymer. If the ratio is n, the average rod will be approximately (P37-36)n-N-terminus P37-P37 C-terminus.

In still other cases, the final nanostructure is composed of two or more components that cannot self-assemble individually but only in combination with each other. In this situation, alternating cycles of assembly can be staged to produce final products of precisely defined structure (see Example 6B below.)

When an immobilized initiator is used, it may be desirable to remove the polymerized unit from the matrix after staged assembly. For this purpose specialized initiators are engineered so that the interaction with the first rod component is rendered reversibly thermolabile (see Example 5 below). In this way, the polymer can be easily separated from the matrix-bound initiator, thereby permitting: 1) easy preparation of stock solutions of uniform parts or subassemblies, and 2) re-use of the matrix-bound initiator for multiple cycles of polymer initiation, growth, and release.

In an embodiment in which a nanostructure is assembled that is attached to a solid matrix via gp34 (or P34), one way in which to detach the nanostructure to bring it into solution is to use a mutant (thermolabile) gp34 that can be made to detach upon exposure to a higher temperature (e.g., 40° C.). Such a mutant gp34, termed T4 tsB45, having a mutation at its C-terminal end such that P34 attaches to the distal tail fiber half at 30° C. but can be separated from it in vitro by incubation at 40° C. in the presence of 1% SDS (unlike wild-type T4 which are stable under these conditions), has been reported (Seed, 1980, Studies of the Bacteriophage T4 Proximal Half Tail Fiber, Ph.D. Thesis, California Institute of Technology), and can be used.

Proteins which catalyze the formation of correct (lowest energy) stable secondary (2°) structure of proteins are called chaperone proteins. (Often, especially in globular proteins, this stabilization is aided by tertiary structure, e.g., stabilization of β-sheets by their interaction in β-barrels or by interaction with a-helices). Normally chaperonins prevent intrachain or interchain interactions which would produce untoward metastable folding intermediates and prevent or delay proper folding. There are two known accessory proteins, gp57 and gp38, in the morphogenesis of T4 phage tail fibers which are sometimes called chaperonins because they are essential for proper maturation of the protein oligomers but are not present in the final structures.

The usual chaperonin system (e.g., groEL/ES) interact with certain oligopeptide moieties of the gene product to prevent unwanted interactions with oligopeptide moieties elsewhere on the same polypeptide or another peptide. These would form metastable folding intermediates which retard or prevent proper folding of the polypeptide to its native (lower energy) state.

Gp57, probably in conjunction with some membrane protein(s), has the role of juxtaposing (and aligning) and/or initiating the folding of 2 or 3 identical gp37 molecules. The aligned peptides then zip up (while mutually stabilizing their nascent β-structures) to form a beam, without further interaction with gp57. Gp57 acts in T4 assembly not only for oligomerization of gp37 but also for gp34 and gp12.

STRUCTURAL COMPONENTS FOR SELF ASSEMBLY OF BEANS IN VITRO

Alternatively to starting the polymerization of chimers with the use of a preformed chimeric or natural oligomeric unit called an initiator produced in vivo, molecules (preferably peptides) that can self-assemble can be produced as fusion proteins, fused to the N- or C-terminus of tail fiber variants of the invention (chimers, deletion/insertion constructs) to align their ends and thus to facilitate their subsequent unaided folding into oligomeric, stable β-folded rod-like (beam) units in vitro, in the absence of the normally required chaperonin proteins (e.g., gp57) and host cell membrane proteins.

As an illustration, consider the P37 unit as an initiator of gp37-36 oligomerization and polymerization. Normally, proper folding of gp37 to a P37 initiator requires a phage infected cell membrane, and two chaperone proteins, gp38 and gp57. In a preferred embodiment, the need for gp38 can be obviated by use of a mutation, ts3813 (a duplication of 7 residues just downstream of the transition zone of gp37) which suppresses gene 38 (Wood, W. B., F. A. Eiserling and R. A. Crowther, 1994, "Long Tail Fibers: Genes, Proteins, Structure, and Assembly," in *Molecular Biology of Bacteriophage* T4, (Jim D. Karam, Editor) American Society for Microbiology, Washington, D.C., pp 282–290). If a moiety that self-assembles into a dimer or trimer or other oligomer ("self-assembling moiety") is fused to a C-terminal deletion of gp37 downstream or upstream of the transition region (the transition region is a conserved 17 amino acid residue region in T4-like tail fiber proteins where the structure of the protein narrows to a thin fiber; see Henning et al., 1994, "Receptor recognition by T-even-type coliphages," in *Molecular Biology of Bacteriophage* T4, Karam (ed.), American Society for Microbiology, Washington, D.C., pp. 291–298; Wood et al., 1994, "Long tail fibers: Genes, proteins, structure, and assembly," in *Molecular Biology of Bacteriophage* T4, Karam (ed.), American Society for Microbiology, Washington, D.C., pp. 282–290), when it is expressed, the self-assembling moiety will oligomerize in parallel and thus align the fused gp37 peptides, permitting them to fold in vitro, in the absence of other chaperonin proteins.

If P37 is a dimer (FIG. 8A), the self-assembling moiety can be a self dimerizing peptide such as the leucine zipper, made from residues 250–281 from the yeast transcription factor, GCN4 (E. K. O'Shea, R. Rutkowski and P. S. Kim, *Science* 243:538, 1989) or the self dimerizing mutant leucine zipper peptide, pIL in which the a positions are substituted with isoleucine and the d positions with leucine (Harbury P. B., T. Zhang, P. S. Kim and T. Alper. 1993. A Switch Between Two-, Three-, and Four-Stranded Coiled Coils in GCN4 Leucine Zipper Mutants. *Science*, 262:1401–1407). If P37 is a trimer (FIG. 8B), the self-assembling moiety can be a self trimerizing mutant leucine zipper peptide, pII in which both the a and d positions are substituted with isoleucine (Harbury P. B., et al. ibid). Alternatively, a collagen peptide can be used as the self-assembling moiety, such as that described by Bella et al. (J. Bella, M. Eaton, B. Brodsky and H. M. Berman. 1994. Crystal and Molecular Structure of a Collagen-Like Peptide at 1.9Å Resolution. *Science*, 226:75–81), which self aligns by an inserted specific non repeating alanine residue near the center.

Self-assembling moieties can be used to make initiators for polymerizations in the absence of the normal initiators. For example, to create an initiator for oligomerization and polymerization of the chimeric monomer, gp37-36, gp37-36-$C_2$ can be used as illustrated in FIG. 9. ($C_2$ means that a dimer forming peptide is fused to the C-terminus of the gp36 moiety. This is used if the beam is a dimeric structure. Otherwise $C_3$—a trimer forming peptide fused to the C-terminus—would be used.) Furthermore, use of the *E. coli* lac repressor N-terminus, e.g., which associates as a tetramer, with two coils facing in each direction could join two diners (or polymers of dimers) end to end, either at their N- or C-termini depending upon which end the self-assembling peptides were placed. They could also join N- to C- termini. In any case, alone, they could only form a dimer, each end of which would be extensible by adding an appropriate chimer monomer (as shown for the simpler case in FIG. 9).

In an alternative embodiment, the self-assembling moiety can be fused to the N-termini of the chimer. In a specific embodiment, the self-assembling moiety is fused to at least a 10 amino acid portion of a T-even-like tail fiber protein.

A self assembling moiety that assembles into a heteroligomer can also be used. For example, if polymerization between beams is directed by the surface of a dimeric cross-β surface, addition of a heterodimeric unit with one surface which does not promote further polymerization would be very useful to cap the penultimate unit and thus terminate polymerization. If the two types of coiled regions of the self-assembling moiety are much more attractive to each other that to themselves, then all of the dimers will be heterodimers. Such is the case for the N-terminal Jun and Fos leucine zipper regions.

A further advantage to such heterodimeric units is the ability to stage polymerization and thus build one unit (or one surface in a 2D array) at a time. For example, suppose surface A attaches to B but neither attaches to itself ([A<->B] is used to symbolize this type of interaction). Mix A/A and B/$B_o$ ($B_o$ is attached to a matrix for easy purification). This will form $B_o$/B-A/A. Now wash out A/A and add B/B. The construct is now $B_o$/B-A/A-B/B. Now add A/$A_o$. The construct is now $B_o$/B-A/A-B/B-A/$A_o$ and no more beams can be added. There are of course many other possibilities.

APPLICATIONS

The uses of the nanostructures of the present invention are manifold and include applications that require highly regular, well-defined arrays of fibers, cages, or solids, which may include specific attachment sites that allow them to associate with other materials.

In one embodiment, a three-dimensional hexagonal array of tubes is used as a molecular sieve or filter, providing regular vertical pores of precise diameter for selective separation of particles by size. Such filters can be used for sterilization of solutions (i.e., to remove microorganisms or viruses), or as a series of molecular-weight cut-off filters. In this case, the protein components of the pores may be modified so as to provide specific surface properties (i.e., hydrophilicity or hydrophobicity, ability to bind specific ligands, etc.). Among the advantages of this type of filtration device is the uniformity and linearity of pores and the high pore to matrix ratio.

In another embodiment, long one-dimensional fibers are incorporated, for example, into paper or cement or plastic during manufacture to provide added wet and dry tensile strength.

In still another embodiment, different nanostructure arrays are impregnated into paper and fabric as anti-counterfeiting markers. In this case, a simple color-linked antibody reaction (such as those commercially available in kits) is used to verify the origin of the material. Alternatively, such nanostructure arrays could bind dyes or other substances, either before or after incorporation to color the paper or fabrics or modify their appearance or properties in other ways.

KITS

The invention also provides kits for making nanostructures, comprising in one or more containers the chimers and deletion constructs of the invention. For example, one such kit comprises in one or more containers purified gp35 and purified gp36-34 chimer. Another such kit comprises purified gp37-36 chimer.

The following examples are intended to illustrate the present invention without limiting its scope.

In the examples below, all restriction enzymes, nucleases, ligases, etc. are commercially available from numerous commercial sources, such as New England Biolabs (NEB), Beverly, Mass.; Life Technologies (GIBCO-BRL), Gaithersburg, Md.; and Boehringer Mannheim Corp. (BMC), Indianapolis, Ind.

EXAMPLE 1

DESIGN, CONSTRUCTION AND EXPRESSION OF INTERNALLY DELETED P37

The gene encoding gp37 contains two sites for the restriction enzyme Bgl II, the first cleavage occurring after nucleotide 293 and the second after nucleotide 1486 (the nucleotides are numbered from the initiator methionine codon ATG.) Thus, digestion of a DNA fragment encoding gp37 with BglII, excision of the intervening fragment (nucleotides 294–1485) and re-ligation of the 5' and 3' fragments results in the formation of an internally deleted gp37, designated Δ37, in which arginine-98 is joined with serine-497.

| | |
|---|---|
| gp37 plasmid DNA (1 µg/µl) | 2 µl |
| NEB buffer #2 (10X) | 1 µl |
| H₂O | 6 µl |
| Bgl II (10 U/µl) | 1 µl |

The gp37 plasmid signifies a pT7-5 plasmid into which gene 37 has been inserted in the multiple cloning site, downstream of a good ribosome binding site and of gene 57 to chaperon the dimerization. The reaction is incubated for 1 h at 37° C. Then, 89 µl of T4 DNA ligase buffer and 1 µl of T4 DNA ligase are added, and the reaction is continued at 16° C. for 4 hours. 2 µl of the Stu I restriction enzyme are then added, and incubation continued at 37° C. for 1 h. (The Stu I restriction enzyme digests residual plasmids that were not cut by Bgl II in the first step, reducing their transformability by about 100-fold.)

The reaction mixture is then transformed into $E.\ coli$ strain BL21, obtained from Novagen, using standard procedures. The transformation mixture is plated onto nutrient agar containing 100 µg/ml ampicillin, and the plates are incubated overnight at 37° C.

Colonies that appear after overnight incubation are picked, and plasmid DNA is extracted and digested with Bgl II as above. The restriction digests are resolved on 1% agarose gels. A successful deletion is evidenced by the appearance after gel electrophoresis of a new DNA fragment of 4.2 kbp, representing the undeleted part of gene 37 which is still attached to the plasmid and which re-formed a BglII site by ligation. The 1.2 kbp DNA fragment bounded by BglII sites in the original gene is no longer in the plasmid and so is missing from the gel.

Plasmids selected for the predicted deletion as above are transformed into $E.\ coli$ strain BL21(DE3). Transformants are grown at 30° C. until the density ($A_{600}$) of the culture reaches 0.6. IPTG is then added to a final concentration of 0.4 mM and incubation is continued at 30° C. for 2 h, after which the cultures are chilled on ice. 20 µl of the culture is then removed and added to 20 µl of a two-fold concentrated "cracking buffer" containing 1% sodium dodecyl sulfate, glycerol, and tracking dye. 15 µl of this solution are loaded onto a 10% polyacrylamide gel; a second aliquot of 15 µl is first incubated in a boiling water bath for 3 min and then loaded on the same gel. After electrophoresis, the gel is fixed and stained. Expression of the deleted gp37 is evidenced by the appearance of a protein species migrating at an apparent molecular mass of 65–70,000 daltons in the boiled sample. The extent of dimerization is suggested by the intensity of higher-molecular mass species in the unboiled sample and/or by the disappearance of the 65–70,000 dalton protein band.

The ability of the deleted polypeptide to dimerize appropriately is directly evaluated by testing its ability to be recognized by an anti-P37 antiserum that reacts only with mature P37 dimers, using a standard protein immunoblotting procedure.

An alternative assay for functional dimerization of the deleted P37 polypeptide (also referred to as ΔP37) is its ability to complement in vivo a T4 37⁻ phage, by first inducing expression of the ΔP37 and then infecting with the T4 mutant, and detecting progeny phage.

A ΔP37 was prepared as described above, and found capable of complementing a T4 37⁻ phage in vivo.

EXAMPLE 2

DESIGN, CONSTRUCTION AND EXPRESSION OF A gp37-36 CHIMER

The starting plasmid for this construction is one in which the gene encoding gp37 is cloned immediately upstream (i.e., 5') of the gene encoding gp36. The plasmid is digested with HaeIII, which deletes the entire 3' region of gp37 DNA downstream of nucleotide 724 to the 3' terminus, and also removes the 5' end of gp36 DNA from the 5' terminus to nucleotide 349. The reaction mixture is identical to that described in Example 1, except that a different plasmid DNA is used, and the enzyme is HaeIII. Ligation using T4 DNA ligase, bacterial transformation, and restriction analysis are also performed as in Example 1. In this case, excision of the central portion of the gene 37–36 insert and religation reveals a novel insert of 346 in-frame codons, which is cut only once by HaeIII (after nucleotide 725). The resulting construct is then expressed in E. coli BL21(DE3) as described in Example 1.

Successful expression of the gp37-36 chimer is evidenced by the appearance of a protein product of about 35,000 daltons. This protein will have the first 242 N-terminal amino acids of gp37 fused to the final 104 C-terminal amino acids of gp36 (numbered 118–221.) The utility of this chimer depends upon its ability to dimerize and attach end-to-end. That is, carboxy termini of said polypeptide will have the capability of interacting with the amino terminus of the P37 protein dimer of bacteriophage T4 and to form an attached dimer, and the amino terminus of the dimer of said polypeptide will have the capability of interacting with other said chimer polypeptides. This property can be tested by assaying whether introduction of ΔP37 initiates dimerization and polymerization. Alternatively, polyclonal antibodies specific to P36 dimer may be used to detect P36 subsequent to initiation of dimerization by ΔP37.

A gp37-36 chimer was prepared similarly to the procedures described above, except that the restriction enzyme TaqI was used instead of HaeIII. Briefly, the 5' fragment resulting from TaqI digestion of gene 37 was ligated to the 3' fragment resulting from TaqI digestion of gene 36. This produced a construct encoding a gp37-36 chimer in which amino acids 1–48 of gp37 were fused to amino acids 100–221 of gp36. This construct was expressed in E. coli BL21(DE3), and the chimer was detected as an 18 kD protein. This gp37-36 chimer was found to inhibit the growth of wild type T4 when expression of the gp37-36 chimer was induced prior to infection (in an in vitro phage inhibition assay).

EXAMPLE 3

MUTATION OF THE GP37-36 CHIMER TO PRODUCE COMPLEMENTARY SUPPRESSORS

The goal of this construction is to produce two variants of a dimerizable P37-36 chimer: One in which the N-terminus of the polypeptide is mutated (A, designated *P37-36) and one in which the C-terminus of the polypeptide is mutated (B, designated P37-36*). The requirement is that the mutated *P37 N-terminus cannot form a joint with the wild-type P36 C-terminus, but only with the mutated *P36 N-terminus. The rationale is that A and B each cannot polymerize independently (as the parent P37-36 protein can), but can only associate with each other sequentially (i.e., P37-36*+*P37-36→P37-36*-*P37-36).

A second construct, *p37-P36*, is formed by recombining *P37-36 and P37-36* in vitro. When the monomers *gp37-36* and gp37-36 are mixed in the presence of P37 initiator, gp37-36 would dimerize and polymerize to (P37-36)n; similarly, *P37 would only catalyze the polymerization of *gp37-36* to (*P37-36*)n. In this case, the two chimers could be of different size and different primary sequence with different potential side-group interactions, and could initiate attachment at different surfaces depending on the attachment specificity of P37.

The starting bacterial strain is a su° strain of E. coli (which lacks the ability to suppress amber mutations). When this strain is infected with a mutant T4 bacteriophage containing amber mutations in genes 35, 36, and 37, phage replication is incomplete, since the tail fiber proteins cannot be synthesized. When this strain is first transformed with a plasmid that directs the expression of the wild type gp35, gp36 and gp37 genes and induced with IPTG, and subsequently infected with mutant phage, infectious phage particles are produced; this is evidenced by the appearance of "nibbled" colonies. Nibbled colonies do not appear round, with smooth edges, but rather have sectors missing. This is caused by attack of a microcolony by a single phage, which replicates and prevents the growth of the bacteria in the missing sector.

For the purposes of this construction, the 3'-terminal region of gene 36 (corresponding to the C-terminal region of gp36) is mutagenized with randomly doped oligonucleotides. Randomly doped oligonucleotides are prepared during chemical synthesis of oligonucleotides, by adding a trace amount (up to a few percent) of the other three nucleotides at a given position, so that the resulting oligonucleotide mix has a small percentage of incorrect nucleotides at that position. Incorporation of such oligonucleotides into the plasmid will result in random mutations (Hutchison et al., Methods.Enzymol. 202:356, 1991).

The mutagenized population of plasmids (containing, however, unmodified genes 36 and 37), is then transformed into the su° bacteria, followed by infection with the mutant T4 phage as above. In this case, the appearance of non-"nibbled" colonies indicates that the mutated gp36 C-termini can no longer interact with wild type P37 to form functional tail fibers. The putative gp36* phenotypes found in such non-nibbled colonies are checked for lack of dimeric N-termini by appropriate immunospecificity as outlined above, and positive colonies are used as source of plasmid for the next step.

Several of these mutated plasmids are recovered and subjected to a second round of mutagenesis, this time using doped oligonucleotides that introduce random mutations into the N-terminal region of gp37 present on the same plasmid. Again, the (now doubly) mutagenized plasmids are transformed into the supo strain of E. coli and transformants are infected with the mutant T4 phage. At this stage, bacterial plates are screened for the re-appearance of "nibbled" colonies. A nibbled colony at this stage indicates that the phage has replicated by virtue of suppression of the non-functional gp36* mutation(s) by the *P37 mutation. In other words, such colonies must contain novel *P37 polypeptides that have now acquired the ability to interact with the P36* proteins encoded on the same plasmid.

The *P37-36 and P37-36* paired suppressor chimers (A and B as above) are then constructed in the same manner as described in Example 2. In this case, however, *P37 is used in place of wild type P37 and P36* is used in place of wild type P36. A *P37-36* chimer can now be made by restriction of *P37-36 and P37-36* and religation in the recombined order. The *P37-36* can be mixed with the P37-36 chimer, and the polymerization of each can be accomplished independently in the presence of the other. This is useful when the rod-like central portion of these chimers have been modified in different ways.

EXAMPLE 4

DESIGN, CONSTRUCTION AND EXPRESSION OF A gp36-34 CHIMER

The starting plasmid for this construction is one in which the vector containing gene 57 and the gene encoding gp36 is cloned immediately upstream (i.e., 5') of the gene encoding gp34. The plasmid is digested with NdeI, which cuts after bp 219 of gene 36 and after bp 2594 of gene 34, thereby deleting the final 148 C-terminal codons from the pg36 moiety and the first 865 N-terminal codons from the gp34 moiety. The reaction mixture is identical to that described in Example 1, except that a different plasmid DNA is used, and the enzyme used is NdeI (NEB). Ligation using T4 DNA ligase, bacterial transformation, and restriction analysis are also performed as in Example 1. This results in a new hybrid gene encoding a protein of 497 amino acids (73 N-terminal amino acids of gp36 and 424 C-terminal amino acids of gp34, numbered 866–1289.)

As an alternative, the starting plasmid is cut with SphI at bp 648 in gene 34, and the Exo-Size Deletion Kit (NEB) is used to create deletions as described above.

The resulting construct is then expressed in *E. coli* BL21 (DE3) as described in Example 1. Successful expression of the gp36-34 chimer is evidenced by the appearance of a protein product of about 55,000 daltons. Preferably, the amino termini of the polypeptide homodimer have the capability of interacting with the gp35 protein, and then the carboxy termini have the capability of interacting with other attached gp35 molecules. Successful formation of the dimer can be detected by reaction with anti-P36 antibodies or by attachment of gp35 or by the in vitro phage inhibition assay described in Example 2.

EXAMPLE 5

ISOLATION OF THERMOLABILE PROTEINS FOR SELF-ASSEMBLY

Thermolabile structures can be utilized in nanostructures for: a) initiation of chimer polymerization (e.g., gp37-36) at low temperature and subsequent inactivation of and separation from the initiator at high temperature; b) initiation of angle formation between P36 and gp35 (e.g., variants of gp35 that have thermolabile attachment sites for P36 N-termini or P34 C-termini, a variant P36 that forms a thermolabile attachment to gp35, and a variant P34 with a thermolabile C-terminal attachment site.) Thermolability may be reversible, permitting reattachment of the appropriate termini when the lower temperature is restored, or it may be irreversible.

To create a variant gp37 that permits heat induced separation of the P36-P37 junction, the 5' end of gp37 DNA is randomly mutagenized using doped oligonucleotides as described above. The mutagenized DNA fragment is then recombined into T4 phage by infection of the cell containing the mutagenized DNA by a T4 phage containing two amber mutations flanking the mutagenized region. Following a low-multiplicity infection, non-amber phage are selected at low temperature on *E. coli* Su° at 30° C. The progeny of these plaques are resuspended in buffered and challenged by heating at 60° C. At this temperature, wild-type tail fibers remain intact and functional, whereas the thermolabile versions release the terminal P37 units and thus render those phage non-infectious.

At this stage, wild type phage are removed by: 1) adsorbing the wild type phage to sensitive bacteria and sedimenting (or filtering out) the bacteria with the adsorbed wild type phage; or 2) reacting the lysate with anti-P37 antibody, followed by immobilized Protein A and removal of adsorbed wild type phage. Either method leaves the noninfectious mutant phage particles in the supernatant fluid or filtrate, from which they can be recovered. The non-infectious phage lacking terminal P37 moieties (and probably the rest of the tail fibers as well) are then urea treated with 6M urea, and mixed with bacterial spheroplasts to permit infection at low multiplicity whereupon they replicate at low temperature and release progeny. Alternatively, infectious phage are reconstituted by in vitro incubation of the mutant phage with wild type P37 at 30° C.; this is followed by infection of intact bacterial cells using the standard protocol. The latter method of infection specifically selects mutant phage in which the thermolability of the P36-P37 junction is reversible.

Using either method, the phage populations are subjected to multiple rounds of selection as above, after which individual phage particles are isolated by plaque purification at 30° C. Finally, the putative mutants are evaluated individually for the following characteristics: 1) loss of infectivity after incubation at high temperatures (40°–60° C.), as measured by a decrease in titer; 2) loss of P37 after incubation at high temperature, as measured by decrease in binding of P37-specific antibody to phage particles; and 3) morphological changes in the tail fibers after incubation at high temperatures, as assessed by electron microscopy.

After mutants are isolated and their phenotypes confirmed, the P37 gene is sequenced. If the mutations localize to particular regions or residues, those sequences are targeted for site-directed mutagenesis to optimize the desired characteristics.

Finally, the mutant gene 37 is cloned into expression plasmids and expressed individually in *E. coli* as in Example 1. The mutant P37 dimers are then purified from bacterial extracts and used in in vitro assembly reactions.

In a similar fashion, mutant gp35 polypeptides can be isolated that exhibit a thermolabile interaction with the N-terminus of P36 or the C-terminus of P34. For thermolabile interaction with P34, phage are incubated at high temperature, resulting in the loss of the entire distal half of the tail fiber (i.e., gp35-P36-P37). The only difference in the experimental protocol is that, in this case, 1) random mutagenesis is performed over the entire gp35 gene; 2) wild-type phage (and distal half-fibers from thermolabile mutants) are separated from thermolabile mutant phage that have been inactivated at high temperature (but still have proximal half tail fibers attached) by precipitating both the distal half-fibers and the phage particles containing intact tail fibers with any of the anti-distal half tail-fiber antibodies followed by Staphylococcal A-protein beads; 3) the mutant phage remaining in the supernatant are reactivated by incubation at low temperature with bacterial extracts containing wild type intact distal half fibers; and 4) stocks of thermolabile gene, 35 mutants grown at 30° C. can be tested for reversible thermolability by inactivation at 60° C. and reincubation at 30° C. Inactivation is performed on a concentrated suspension of phage, and reincubation at 30° C. is performed either before or after dilution. If phage are successfully reactivated before, but not after, dilution, this indicates that their gp35 is reversibly thermolabile.

To create a gene 36 mutation with a thermolabile gp35-P36 linkage, the C-terminus of gene 36 is mutagenized as described above, and the mutant selected for reversibility. An alternative is to mutagenize gp35 to create a gene 35 mutant in which the gp35-P36 linkage will dissociate at 60° C. In this case, incubation with anti-gp35 antibodies can be used to precipitate the phage without P36-P37 and thus to separate them from the wild-type phage and distal half-tail fibers (P36-P37), since the variant gp35 will remain attached to P34.

EXAMPLE 6

ASSEMBLY OF ONE-DIMENSIONAL RODS

A. Simple Assembly:
The P37-36 chimer described in Example 2 is capable of self-assembly, but requires a P37 initiator to bind the first unit of the rod. Therefore, a P37 or a ΔP37 dimer is either attached to a solid matrix or is free in solution to serve as an initiator. If the initiator is, attached to a solid matrix, a thermolabile P37 dimer is preferably used. Addition of an extract containing gp37-36, or the purified gp37-36 chimer, results in the assembly of linear multimers of increasing length. In the matrix-bound case, the final rods are released by a brief incubation at high temperature (40°–60° C., depending on the characteristics of the particular thermolabile P37 variant.)

The ratio of initiator to gp37-36 can be varied, and the size distribution of the rods is measured by any of the following methods: 1) Size exclusion chromatography; 2) Increase in the viscosity of the solution; and 3) Direct measurement by electron microscopy.

B. Staged assembly:

The P37-36 variants *P37-36 and P37-36* described in Example 3 cannot self-polymerize. This allows the staged assembly of rods of defined length, according to the following protocol:

1. Attach initiator P37 (preferably thermolabile) to a matrix.
2. Add excess *gp37-36 to attach and oligomerize as P37-36 homooligomers to the N-terminus of P37.
3. Wash out unreacted *gp37-36 and flood with gp37-36*.
4. Wash out unreacted gp37-36* and flood with excess *gp37-36.
5. Repeat steps 2–4, n-1 times.
6. Release assembly from matrix by brief incubation at high temperature as above.

The linear dimensions of the protein rods in the batch will depend upon the lengths of the unit heterochimers and the number of cycles (n) of addition. This method has the advantage of insuring absolute reproducibility of rod length and a homogenous, monodisperse size distribution from one preparation to another.

EXAMPLE 7

STAGED ASSEMBLY OF POLYGONS

The following assembly strategy utilizes gp35 as an angle joint to allow the formation of polygons. For the purpose of this example, the angle formed by gp35 is assumed to be 137°. The rod unit comprises the P36-34 chimer described in Example 4, which is incapable of self-polymerization. The P36-34 homodimer is made from a bacterial clone in which both gp36-34 and gp57 are expressed. The gp57 can chaperone the homodimerization of gp36-34 to P36-34.

1. Initiator: The incomplete distal half fiber P36-37 is attached to a solid matrix by the P37 C-terminus. Thermolabile gp35 as described in Example 5 is then added to form the intact initiator.
2. Excess P36-34 chimer is added to attach a single P36-34. Following binding to the matrix via gp35, the unbound chimer is washed out.
3. Wild-type (i.e., non-thermolabile) gp35 is then added in excess. After incubation, the unbound material is washed out.
4. Steps 2 and 3 are repeated 7–8 times.
5. The assembly is released from the matrix by brief incubation at high temperature.

The released polymeric rod, 8 units long, will form a regular 8-sided polygon, whose sides comprise the P36-34 dimer and whose joints comprise the wild-type gp35 monomer. However, there will be some multimers of these 8 units bound as helices. When a unit does not close, but instead adds another to its terminus, the unit cannot close further and the helix can build in either direction. The direction of the first overlap also determines the handedness of the helix. Ten (or seven)-unit rods may form helices more frequently than polygons since their natural angles are 144°0 (or 128.6°). The likelihood of closure of a regular polygon depends not only on the average angle of gp35 but also on its flexibility, which can be further manipulated by genetic or environmental modification.

The type of polygon that is formed using this protocol depends upon the length of rod units and the angle formed by the angle joint. For example, alternating rod units of different sizes can be used in step 2. In addition, variant gp35 polypeptides that form angles different than the natural angle of 137° can be used, allowing the formation of different regular polygons. Furthermore, for a given polygon with an even number of sides and equal angles, the sides in either half can be of any size provided the two halves are symmetric.

What is claimed is:

1. An isolated polypeptide consisting essentially of a fusion protein between the gp36 and gp37 proteins of bacteriophage T4, wherein amino acid residues 1–242 of gp37 (SEQ ID NO:6) are fused in proper reading frame amino-terminal to amino acid residues 118–221 of gp36 (SEQ ID NO:5).

2. The polypeptide of claim 1 wherein a plurality of carboxy termini of a plurality of said polypeptide have the capability of interacting with the amino termini of the P37 protein oligomer of bacteriophage T4 and to form an attached oligomer, and the amino termini of the attached oligomer have the capability of interacting with the carboxy termini of gp36 polypeptides of bacteriophage T4.

3. An isolated polypeptide consisting essentially of a variant of the gp36 protein of bacteriophage T4, wherein said polypeptide lacks the capability of interacting with the amino terminus of the P37 protein oligomer of bacteriophage T4.

4. An isolated polypeptide consisting essentially of a fusion protein between the gp36 and gp34 proteins of bacteriophage T4, wherein amino acid residues 1–73 of gp36 (SEQ ID NO:5) are fused in proper reading frame amino-terminal to amino acid residues 866–1289 of gp34 (SEQ ID NO:2).

5. An oligomer of the polypeptide of claim 4, wherein the amino termini of said oligomer have the capability of interacting with the gp35 protein of bacteriophage T4.

6. An isolated fusion protein consisting essentially of a first portion of a gp37 protein of a T-even-like bacteriophage consisting of in the range of the first 10–60 N-terminal amino acids of the gp37 protein fused to a second portion of a gp36 protein of a T-even-like bacteriophage consisting of in the range of the last 10–60 C-terminal amino acids of the gp36 protein.

7. An isolated fusion protein consisting essentially of a first portion of a gp37 protein of a T-even-like bacteriophage consisting of at least the first 10 N-terminal amino acids of the gp37 protein fused to a second portion of a gp36 protein of a T-even-like bacteriophage consisting of at least the last 10 C-terminal amino acids of the gp36 protein.

8. An isolated fusion protein consisting essentially of a first portion of a gp37 protein of a T-even-like bacteriophage consisting of at least the first 20 N-terminal amino acids of the gp37 protein fused to a second portion of a gp36 protein of a T-even-like bacteriophage consisting of at least the last 20 C-terminal amino acids of the gp36 protein.

9. An isolated fusion protein consisting essentially of a first portion of a gp36 protein of a T-even-like bacteriophage consisting of at least the first 20 N-terminal amino acids of the gp36 protein fused to a second portion of a gp34 protein of a T-even-like bacteriophage consisting of at least the last 20 C-terminal amino acids of the gp34 protein.

10. An isolated protein comprising at least 20 continguous amino acids of the gp37, gp36, or gp34 protein of a T-even-like bacteriophage, and lacking at least 5 amino acids of the amino- or carboxy-terminus of the protein.

11. A method for making a polygonal nanostructure comprising contacting a fusion protein with purified gp35 proteins of a T-even-like bacteriophage, said fusion protein consisting essentially of a portion of a gp36 protein of a T-even-like bacteriophage consisting of at least the first 20 N-terminal amino acids of the gp36 protein fused to a second portion of a gp34 protein of a T-even-like bacteriophage consisting of at least the last 20 C-terminal amino acids of the gp34 protein.

12. A method for making a nanostructure comprising contacting a plurality of fusion proteins with each other, said fusion proteins consisting essentially of a portion of a gp37 protein of a T-even-like bacteriophage consisting of in the range of the first 10–60 N-terminal amino acids of the gp37 protein fused to a second portion of a gp36 protein of a T-even-like bacteriophage consisting of in the range of the last 10–60 C-terminal amino acids of the gp36 protein.

13. A kit comprising in one or more containers the fusion protein of claim 6.

14. A kit comprising in one or more containers the fusion protein of claim 8.

15. A kit comprising in one or more containers the fusion protein of claim 9.

16. A kit comprising in one or more containers the fusion protein of claim 9, and an isolated gp35 protein of a T-even-like bacteriophage.

17. The protein of claim 6 wherein the T-even-like bacteriophage is T4.

18. The protein of claim 9 wherein the T-even-like bacteriophage is T4.

19. An isolated polypeptide consisting essentially of a variant of the gp36 protein of bacteriophage T4, wherein the interaction of said polypeptide with the P37 protein oligomer of bacteriophage T4 is unstable at temperatures between about 40° C. and about 60° C.

20. An isolated polypeptide consisting essentially of a variant of the gp36 protein of bacteriophage T4, wherein the interaction of said polypeptide with the gp35 protein of bacteriophage T4 is unstable at temperatures between about 40° C. and about 60° C.

21. A homooligomer of the polypeptide of claim 7.

22. A homooligomer of the polypeptide of claim 9.

* * * * *

UNITED STATES PATENT AND TRADEMARK OFFICE
CERTIFICATE OF CORRECTION

PATENT NO. : 5,864,013

DATED : January 26, 1999

INVENTOR(S) : Edward B. Goldberg

It is certified that error appears in the above-identified patent and that said Letters Patent is hereby corrected as shown below:

At the title page, first column, following "[73] Assignee: NanoFrames, LLC, Brookline, Mass.", please insert the following:

-- [*] Notice: The term of this patent shall not extend beyond the expiration date of Pat. No. 5,877,279. -- .

At the title page, second column, following "[45] Date of Patent:", please delete "Jan. 26, 1999" and substitute therefor -- *Jan. 26, 1999 -- .

At column 13, line 24, please delete "BEANS" and substitute therefor -- BEAMS -- .

Signed and Sealed this

Sixth Day of June, 2000

Attest:

Attesting Officer

Q. TODD DICKINSON

*Director of Patents and Trademarks*

UNITED STATES PATENT AND TRADEMARK OFFICE
CERTIFICATE OF CORRECTION

PATENT NO. : 5,864,013
DATED : January 26, 1999
INVENTOR(S) : Edward B. Goldberg It is certified that error appears in the above-identified patent and that said Letters Patent is hereby corrected as shown below:

<u>Title page,</u>
Line 15, please delete "proten" and substitute therefor -- protein --.

<u>Column 8,</u>
Line 66, please delete "anti-P34 P34" and substitute therefor -- anti-P34 --.

<u>Column 47,</u>
Line 26, please delete "continguous" and substitute therefor -- contiguous --.

Signed and Sealed this

Twenty-third Day of April, 2002

Attest:

JAMES E. ROGAN
*Director of the United States Patent and Trademark Office*

*Attesting Officer*